US010537308B2

(12) United States Patent
Zhadkevich

(10) Patent No.: US 10,537,308 B2
(45) Date of Patent: Jan. 21, 2020

(54) CATHETER FOR PREVENTION OF STROKE AND METHOD OF USE

(71) Applicant: Michael Zhadkevich, Inman, SC (US)

(72) Inventor: Michael Zhadkevich, Greenwood, SC (US)

( * ) Notice: Subject to any disclaimer, the term of this patent is extended or adjusted under 35 U.S.C. 154(b) by 255 days.

(21) Appl. No.: 15/333,076

(22) Filed: Oct. 24, 2016

(65) Prior Publication Data

US 2017/0100144 A1 Apr. 13, 2017

Related U.S. Application Data

(63) Continuation-in-part of application No. 13/918,492, filed on Jun. 14, 2013, now Pat. No. 9,498,225.
(Continued)

(51) Int. Cl.
*A61B 17/221* (2006.01)
*A61F 2/01* (2006.01)
(Continued)

(52) U.S. Cl.
CPC .............. *A61B 8/488* (2013.01); *A61B 8/085* (2013.01); *A61B 17/12045* (2013.01);
(Continued)

(58) Field of Classification Search
CPC .......... A61B 17/12027; A61B 17/1204; A61B 17/12131; A61B 17/1214; A61B 17/1215;
(Continued)

(56) References Cited

U.S. PATENT DOCUMENTS 3,587,584 A 6/1971 Bourbon
4,395,806 A 8/1983 Wonder
(Continued)

FOREIGN PATENT DOCUMENTS

EP 0 203 310 A2 3/1986
EP 2 260 776 A1 12/2010
(Continued)

OTHER PUBLICATIONS

Wikipedia; "Pulmonary artery catheter Pulmonary artery catheter", Wikipedia, The Free Encylcopedia., May 12, 2012, XP055235920, Retrieved from the Internet: URLhttps://en.wikipedia.org/w/index.php?title=Pulmonary_artery_catheter&oldid+694424669 [retrieved on Dec. 14, 2015]; 5 pages; (copy enclosed).
(Continued)

*Primary Examiner* — Tuan V Nguyen
(74) *Attorney, Agent, or Firm* — Bennett Mullinax, LLC

(57) ABSTRACT

A catheter for prevention of stroke by diverting and filtering the blood flow to carotid and vertebral arteries is provided. The catheter includes at least one balloon with an outer mesh cover that expands upon the balloon inflation and stays expanded after the balloon is deflated. The inflation of the balloon in the aortic arch or head vessels provides the deflection of embolic particles from the cerebral circulation and expands the outer mesh that provides for filtering and deflection of cerebral emboli after the balloon is deflated. An associated method of prevention of cerebral emboli and embolic stroke is provided.

26 Claims, 36 Drawing Sheets

Related U.S. Application Data

(60) Provisional application No. 61/668,980, filed on Jul. 6, 2012.

(51) Int. Cl.
 *A61B 8/08* (2006.01)
 *A61B 17/12* (2006.01)

(52) U.S. Cl.
 CPC .. *A61B 17/12109* (2013.01); *A61B 17/12136* (2013.01); *A61F 2/01* (2013.01)

(58) Field of Classification Search
 CPC ........ A61B 17/12154; A61B 17/12031; A61B 17/12036; A61B 17/12045; A61B 17/12109; A61B 17/12136; A61B 17/12168; A61B 2017/12127; A61M 25/10; A61M 25/1002; A61M 25/1011
 See application file for complete search history.

(56) References Cited

U.S. PATENT DOCUMENTS

| | | | |
|---|---|---|---|
| 4,676,232 A | 6/1987 | Olsson et al. | |
| 4,745,924 A | 5/1988 | Ruff | |
| 4,984,563 A | 1/1991 | Renaud | |
| 5,059,177 A | 10/1991 | Towne | |
| 5,271,409 A | 12/1993 | Millay | |
| 5,360,403 A | 11/1994 | Mische | |
| 5,441,051 A | 8/1995 | Hileman | |
| 5,514,079 A | 5/1996 | Dillon | |
| 5,741,295 A | 4/1998 | McEwen | |
| 5,908,407 A | 6/1999 | Frazee | |
| 6,156,005 A | 12/2000 | Theron | |
| 6,168,579 B1 * | 1/2001 | Tsugita | A61B 17/12109 604/104 |
| 6,425,916 B1 | 7/2002 | Garrison et al. | |
| 6,595,980 B1 | 7/2003 | Barbut | |
| 7,458,980 B2 | 12/2008 | Barbut | |
| 7,727,254 B2 | 6/2010 | Pah | |
| 7,972,356 B2 | 7/2011 | Boyle et al. | |
| D643,536 S | 8/2011 | Vivenzio | |
| 7,998,104 B2 | 8/2011 | Chang | |
| 8,025,674 B2 | 9/2011 | Barbut et al. | |
| 8,034,043 B1 | 10/2011 | Barbut | |
| 8,062,324 B2 | 11/2011 | Carpenter | |
| 9,795,470 B2 | 10/2017 | Ganesan | |
| 2002/0115982 A1 * | 8/2002 | Barbut | A61B 5/0215 604/509 |
| 2002/0173815 A1 | 11/2002 | Hogendijk | |
| 2003/0036728 A1 * | 2/2003 | Samson | A61B 17/12045 604/103.01 |
| 2003/0176884 A1 * | 9/2003 | Berrada | A61F 2/013 606/200 |
| 2005/0015048 A1 | 1/2005 | Chiu | |
| 2005/0038468 A1 * | 2/2005 | Panetta | A61F 2/013 606/200 |
| 2005/0059931 A1 | 3/2005 | Garrison | |
| 2005/0075531 A1 | 4/2005 | Loeb et al. | |
| 2005/0154344 A1 | 7/2005 | Chang | |
| 2005/0197624 A1 | 9/2005 | Goodson | |
| 2009/0326575 A1 | 12/2009 | Galdonik | |
| 2010/0113939 A1 | 5/2010 | Mashimo | |
| 2010/0179583 A1 | 7/2010 | Carpenter et al. | |
| 2010/0324589 A1 | 12/2010 | Carpenter et al. | |
| 2011/0028934 A1 | 2/2011 | Buckman et al. | |
| 2011/0054322 A1 | 3/2011 | Zanatta | |
| 2011/0295114 A1 | 12/2011 | Agah | |
| 2012/0179195 A1 | 7/2012 | Lashinski | |
| 2012/0203265 A1 | 8/2012 | Heuser | |
| 2013/0023909 A1 | 1/2013 | Duhay | |
| 2014/0336690 A1 | 11/2014 | Zhadkevich | |

FOREIGN PATENT DOCUMENTS

| | | |
|---|---|---|
| EP | 2 682 154 A1 | 1/2014 |
| WO | WO 99/36028 | 7/1999 |
| WO | WO 00/32266 A1 | 6/2000 |
| WO | WO 01/13983 A2 | 3/2001 |
| WO | WO 2010/081025 A1 | 7/2010 |
| WO | WO 2011/017103 A2 | 2/2011 |
| WO | WO 2012/083227 A1 | 6/2012 |

OTHER PUBLICATIONS

Joe Elberry; "Swan Ganz Physiology"; You Tube video from https://www.youtube.com/watch?v=7putxZN7ij4; Jan. 21, 2012; copyright 2012; published by Edwards Lifesciences, Irvine, California, USA; 2 page screen shot; (copy enclosed).

Various Anonymous Authors; "Circle of Willis"; Wikipedia article retrieved from https://en.wikipedia.org/wiki/Circle_of_Willis; retrieved on Nov. 8, 2016; pp. 1-4; copyright 2016 Wikipedia Foundation Inc.; San Francisco; California; USA; 4 pages; (copy enclosed).

United States Patent Office, Office Action; U.S. Appl. No. 15/295,285; United States Patent Office: pp. 1-12, publisher United States Patent Office: Published Alexandria, Virginia, USA; copyright and dated May 3, 2018; copy enclosed (12 pages).

* cited by examiner

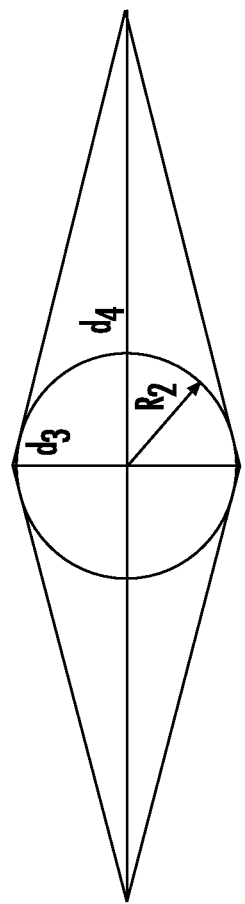
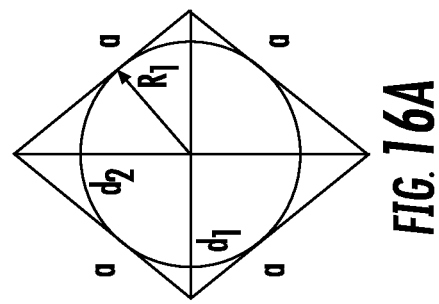
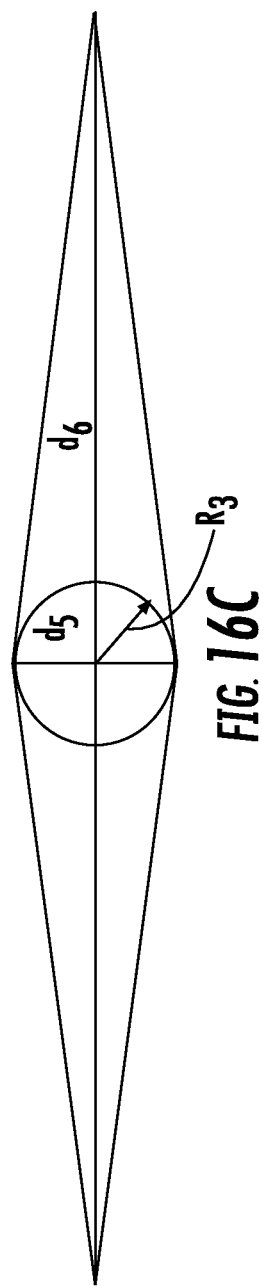
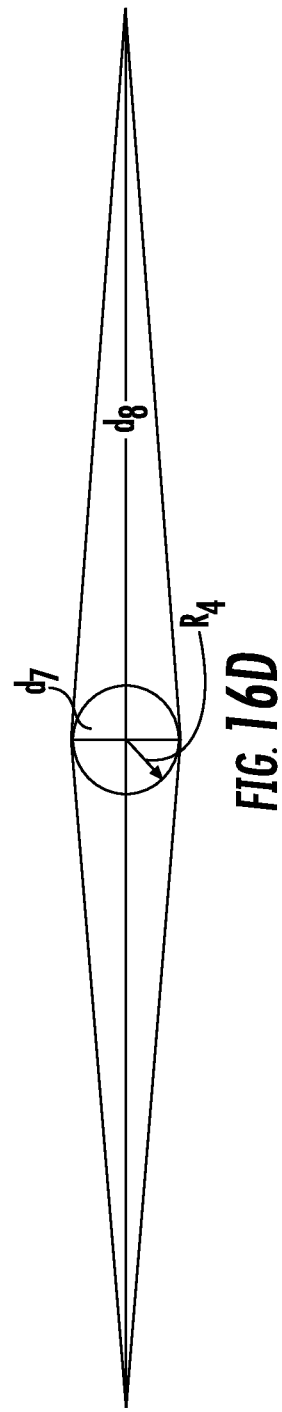
FIG. 16A
FIG. 16B
FIG. 16C
FIG. 16D

CATHETER FOR PREVENTION OF STROKE AND METHOD OF USE

This application is a continuation-in-part and claims the benefit of U.S. patent application Ser. No. 13/918,492 filed on Jun. 14, 2013, that issued as U.S. Pat. No. 9,498,225 on Nov. 22, 2016, and entitled "Occluding Catheter and Method of Prevention of Stroke". U.S. patent application Ser. No. 13/918,492 claims the benefit of U.S. patent application Ser. No. 61/668,980 filed on Jul. 6, 2012 and entitled "Device and Method of Prevention of Embolic Stroke". U.S. application Ser. Nos. 61/668,980, 13/918,492 are incorporated by reference herein in their entireties for all purposes.

FIELD OF THE INVENTION

The present invention relates generally to devices and methods for the prevention of stroke. More particularly, the present application involves an occluding catheter that has at least one balloon and a filtering mesh that is inserted into the circulatory system of the patient to deflect, trap and remove the emboli entering the brain through the carotid arteries and subclavian arteries during performance of an emboligenic procedure to prevent an embolic stroke.

BACKGROUND

Intraoperative embolic stroke is one of the most dreadful complications of cardiac, aortic and vascular procedures, diagnosed in 1-22% of patients undergoing cardiovascular surgery. Even more frequently, in up to 70% of cases, patients undergoing heart, valve, coronary artery bypass and aortic surgery experience subclinical embolic events as recorded by transcranial Doppler and MRI. Recent data showed an astounding incidence of stroke as detected by MRI in practically all groups od cardiac patients: in TAVR v—84%, Aortic Valve Replacement—52%, emergent coronary intervention—49%, Balloon Aortic Valvuloplasty—40%, Cardiac Ablation 38% and Coronary Artery Bypass Surgery—20%. These embolic events lead to cognitive impairment and disability and have a significant impact on patients' recovery.

The main sources of cerebral emboli and stroke in this setting resides in the heart, heart valves, thoracic aorta, and great vessels when these structures are intervened thereon. Even simple cardiac catheterization with an endovascular catheter can induce trauma of the atherosclerotic thoracic aorta leading to formation of embolic particles with subsequent embolic brain injury ranging from latent ischemic foci to a massive or even fatal stroke.

Multiple devices are known that attempt to prevent embolization of the carotid arteries during endovascular and cardiac interventions. These anti-embolic devices, however, have not received wide acceptance in surgery of the heart, heart valves and thoracic aorta due to their complexity and invasive character with the risk of additional trauma to the inner vessel wall resulting in a high risk to benefit ratio. Known devices require insertion of additional hardware into the arterial system or aorta, a procedure that is known by itself to be associated with all classical risks of endovascular intervention, including aortic dissection, bleeding, thrombosis, and carotid cerebral embolization and stroke. One known intra-aortic filter device that is inserted into the ascending portion of the thoracic aorta via an aortic cannula to capture potential embolic material released from the heart and aortic wall during heart surgery was found to be quite difficult to implement and was reported to be associated with major trauma to aortic wall and acute aortic dissection.

Another such device for preventing emboli into the cerebral circulation includes a porous deflector/intra-aortic shield that captures or diverts potential emboli into the distal vascular. A yet additional device has also been proposed for use during aortic valve surgery and is an intra-aortic filter catheter that captures emboli during this procedure. It has been established that intravascular filters are not able to capture emboli smaller than the pore size of the available devices (currently 60-140 μm) resulting in cerebral microembolization. Embolization may also occur due to poor apposition of the filter to the aortic or carotid arterial wall.

Furthermore, the placement of the filter by itself may produce cerebral emboli. For example, the mere passing of a guide wire into a carotid artery generates approximately 40,000 microemboli, with a significant percentage of small, less than 60 μm, particles that are not retained by standard filters. Therefore, in spite of multiple innovations in the field of anti-embolic devices, the problem of cerebral emboli and stroke during cardiovascular surgery is far from being resolved.

It is known to use balloon occlusion catheters for the prevention of embolic stroke. In this regard, the balloon occlusion catheter is placed inside of one of the carotid arteries when a procedure, for example carotid angioplasty and stenting, is conducted on the carotid artery in question. Although capable of preventing stroke when a single carotid artery is operated upon, this device cannot work to prevent stroke during procedures on the heart and aorta, endovascular or open, and cannot provide for bilateral occlusion. This device cannot simultaneously occlude both the left and right carotid arteries to prevent flow simultaneously through both of these arteries, and thus cannot prevent stroke should emboli flow into the non-blocked carotid artery. Moreover, it can not occlude the flow to both carotid arteries for a long period of time and to combine the occlusion with the filtering of cerebral emboli.

Further, known endovascular carotid occluding devices require a guide wire to be inserted into the carotid arterial system. This procedure by itself is known to induce carotid trauma and cause the formation of cerebral emboli and resultant stroke. Still additionally, prior endovascular carotid occluding devices are not capable of reducing arterial flow through both right and left vertebral arteries, either at the same time or individually. This deficiency may allow emboli to enter vertebrobasilar i.e. posterior cerebral circulation and cause stroke. As such, there remains room for variation and improvement within the art and it appears logical to create a device that would allow for both deflection and filtering of cerebral emboli depending on each particular clinical situation.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended Figs. in which:

FIG. 3-B is a front view of the patient of FIG. 2 with the occluding catheter after deflation of the occluding balloons leaving the filtering mesh expanded while the flow to the brain is re-established.

FIG. 4-B is a front view of the patient of FIG. 3 that shows the filtering and capturing the emboli by the expanded mesh, preventing their entry into carotid arteries when the occluding balloons are deflated and the flow to the brain is re-established.

FIG. 5-A is a front view of an occluding catheter of FIG. 5 in an inflated state.

FIG. 5-B is a front view of an occluding catheter FIG. 5 in a deflated state after the filtering mesh has been expanded.

FIG. 5-C is a front view of an occluding catheter in accordance with another exemplary embodiment in an inflated state.

FIG. 5-D is a front view of an occluding catheter of FIG. 5-C in a deflated state and the filtering mesh expanded.

FIG. 5-E is a front view of an occluding catheter in accordance with another exemplary embodiment in an inflated state.

FIG. 5-F is a front view of an occluding catheter of FIG. 5-E in a deflated state and the filtering mesh expanded.

FIG. 5-G is a front view of a deflated occluding catheter with its mesh at the initial stage of its recapturing using an outer sheath.

FIG. 5-H is a front view of a deflated occluding catheter with a further advancement of the outer sheath over the occluding balloon catheter and the filtering mesh.

FIG. 5-I is a front view of a deflated occluding catheter with a final stage of advancement of the outer sheath over the occluding balloon catheter and the filtering mesh.

FIG. 9-B is a perspective view of the occluding catheter of FIG. 5-C in an inflated state and with a section cut away to view interior portions.

FIG. 9-C is a perspective view of the occluding catheter of FIG. 5-C in an inflated state and with showing different areas of the mesh, containing pores of a different size.

FIG. 10-C is a cross view taken along line 10-10 of FIG. 5-C showing areas of the mesh containing pores of a different size.

FIG. 10-D is a cross-sectional view taken along line 10-10 of FIG. 10-C with areas showing different sizes of the mesh pores corresponding to the opposite side of the occluding catheter.

FIG. 11-B is a front view of the patient with a deflated occluding catheter of FIG. 11-A after the filtering mesh has been expanded.

FIG. 12-B is a front view of the patient with a deflated occluding catheter and expanded filtering mesh of FIG. 11-B and an alarm system in accordance with a further exemplary embodiment.

FIG. 13-B is a front view of the patient with an inflated occluding catheter of FIG. 13-A with the filtering mesh expanded.

FIG. 13-C is a front view of the patient with an inflated occluding catheter of FIG. 13-B showing the areas of the mesh containing filtering pores of a different size.

FIG. 14-B is a front view of the patient with the occluding catheter of FIGS. 13-B, 13-C and 14-A in a fully deflated state with the filtering mesh being retracted into the outer sheath.

FIG. 14-C is a front view of another embodiment with a filtering mesh between proximal and distal occluding balloons that are inflated in subclavian arteries without blocking the flow to carotid arteries with arrows showing the flow of a filtered blood passing through the mesh to both carotid arteries.

FIG. 16-A is a front view of a pore of a filtering mesh in accordance with one of the exemplary embodiments in a neutral position or after applying an axial compression along the diagonal $d_1$.

FIG. 16-B is a front view of a pore of a filtering mesh of FIG. 16-A after applying an axial traction along the diagonal $d_2$.

FIG. 16-C is a front view of a pore of a filtering mesh of FIG. 16-B after applying an additional axial traction along the diagonal $d_2$.

FIG. 16-D is a front view of a pore of a filtering mesh of FIG. 16-C after applying yet additional axial traction along the diagonal $d_2$.

FIG. 17-B is a perspective view of another exemplary embodiment of a filtering mesh in a neutral position and after applying a combination of a torqueing (T), stretching (S), extending (E) and bending (B) forces with the schematic view of a lumen of a filtering pore before ($L_1$) and after ($L_2$) applying such forces.

Figure 1:
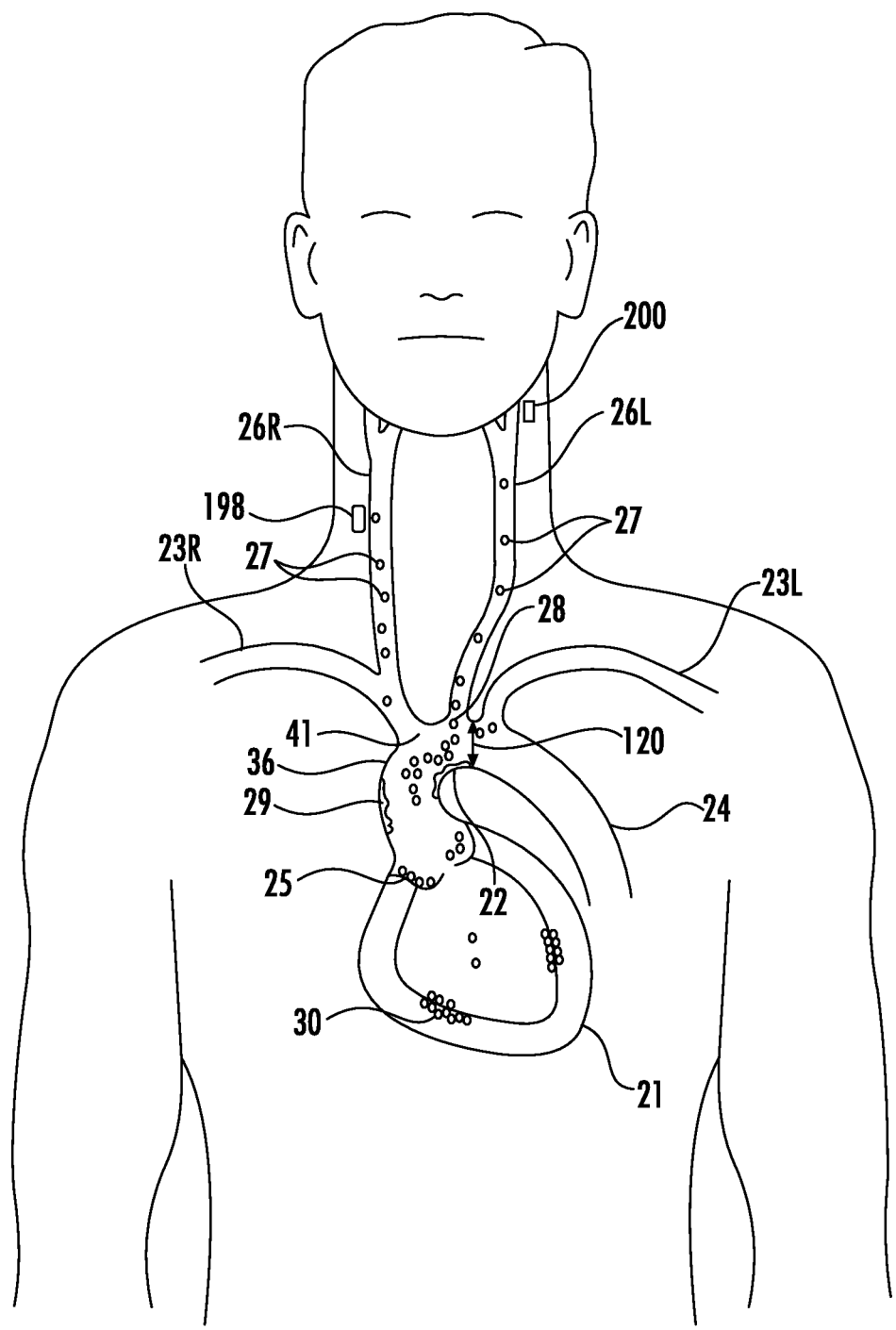
FIG. 1 is a front view of a patient with emboli in the heart and ascending thoracic aorta with subsequent propagation of emboli into both carotid arteries with the source of emboli being diseased aorta, aortic valve and the heart.

Repeat use of reference characters in the present specification and drawings is intended to represent the same or analogous features or elements of the invention.

DETAILED DESCRIPTION OF REPRESENTATIVE EMBODIMENTS

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5.

The present invention provides for an occluding catheter 37 carrying a filtering mesh 130, 140 or 150 that may be introduced into the circulatory system of a patient in order to prevent emboli 28 from entering the carotid arteries 26R, 26L and causing stroke. The occluding catheter 37 may be arranged so that it has one occluding balloon 38, or a pair of occluding balloons 38 and 42, or three or more occluding balloons in accordance with different exemplary embodiments. The occluding catheter 37 can be positioned within the circulatory system in a deflated state. When needed, the occluding catheter 37 can be inflated in order to block and/or filter blood flow through the carotid arteries 26R, 26L and hence prevent emboli 28 from flowing through the carotid arteries 26R, 26L and into cerebral circulation. The occluding catheter 37 can be equipped with the capability of employing a guide wire 100 and with the ability to measure, pressure downstream in one or more arteries of the patient to ensure proper blockage and/or aspirate the emboli trapped inside the filtering mesh, covering the occluding balloons. If needed or desired, flow may be blocked through both vertebral arteries. An associated method for preventing emboli 28 from entering cerebral circulation is also provided.

With reference to FIG. 1, a front view of a patient is shown in which emboli 28 are transferred from the aortic arch 22 into the carotid arteries 26R, 26L. The emboli 27 that are present in the carotid arteries 26R, 26L can then be transferred into the cerebral circulation causing stroke of the patient. The emboli 27 may be fragments of atherosclerotic plaque 29 of the ascending aorta 36 that become dislodged during manipulation of the ascending thoracic aorta 36. Also shown in FIG. 1 is calcification of the aortic valve 25 and intracardiac emboli 30 of the heart 21 that can also be the origin of emboli 27 eventually present in the carotid arteries 26R, 26L. The intracardiac emboli 30 may include air, gas, thrombi and atherosclerotic materials. Although all of the various emboli in the heart 21, aortic arch 22, ascending aorta 36, and aortic valve 25 need not be present in all instances, they are all shown in FIG. 1 for sake of example. Trauma to the heart 21, aortic valve 25 and aortic structures during placement and removal of items such as aortic clamps, catheters, guidewires, intravascular devices and electrophysiological instruments, along with manipulations such as coronary artery bypass grafting, aortic and mitral valve replacement, catheter ablation, endovascular grafting of the aorta 22, balloon aortic valvuloplasty, percutaneous implantation of the aortic or mitral valves, endovascular manipulations on the aorta 22, aortic branches and the heart 21 may give rise to the presence of emboli 27 in the carotid arteries 26R, 26L. Critical moments of the aforementioned procedures (for example during the aortic cross clamp manipulation, percutaneous aortic and mitral valvuloplasty or valve implantation, coronary interventions, endovascular grafting of the aorta 22 and its branches, and endovascular procedures on the aorta 22) may cause emboli 27 to form and cause stroke and are referred to as "emboligenic" events.

Figure 2:
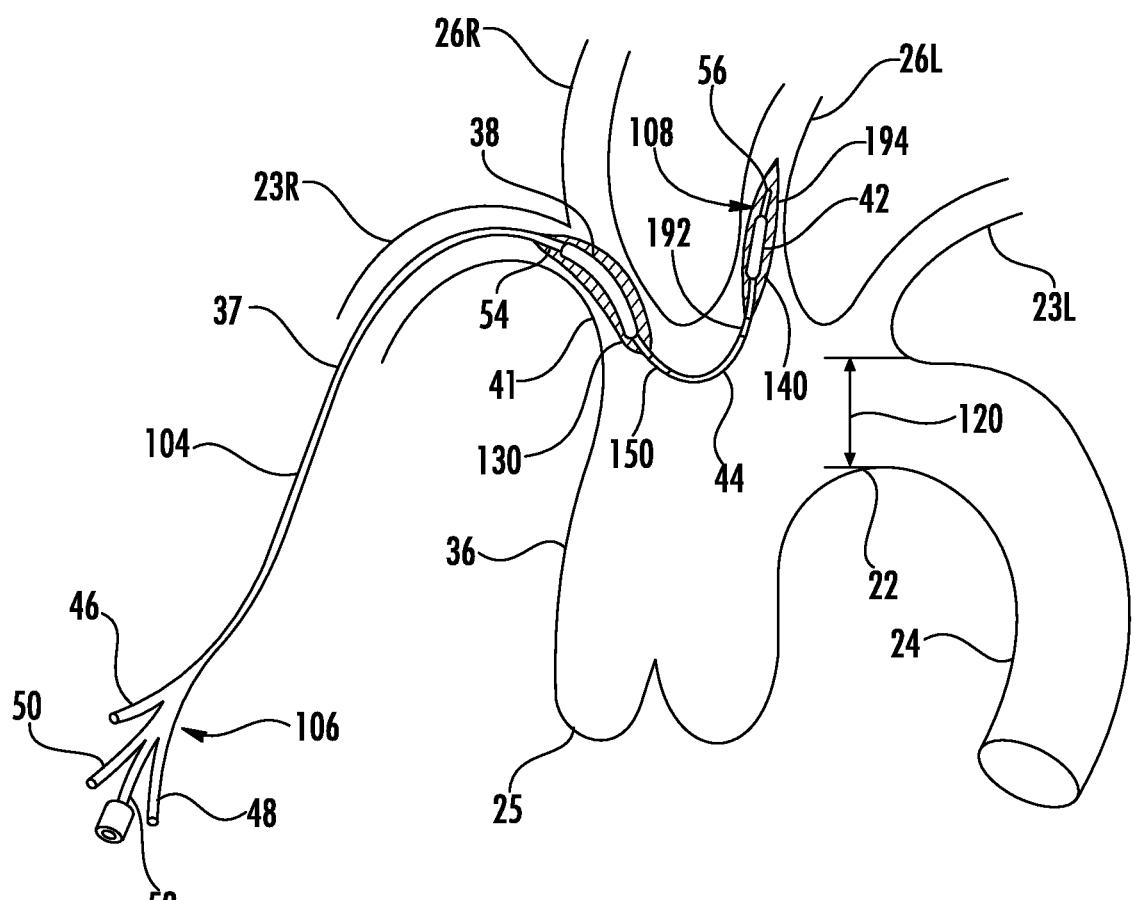
FIG. 2 is a front view of the patient with an occluding catheter in a deflated state positioned within the circulatory system of the patient.

FIG. 2 discloses an occluding catheter 37 positioned within the circulatory system of the patient. The occluding catheter 37 is introduced through the right subclavian artery 23R and has a shaft 104 with a proximal end 106 located outside of the patient, and a distal end 108 positioned within the left carotid artery 26L. The occluding catheter 37 has a proximal occluding balloon 38 carrying an expandable filtering mesh 130 located closer to the health care provider and thus closer to the proximal end 106 than a distal occluding balloon 42, carrying an expandable filtering, mesh 140 which is farther away from the health care provider and thus closer to the distal end 108. The proximal occluding balloon 38, covered by mesh 130, may be located within an innominate artery 41 of the patient. The occluding catheter 37 carrying mesh 130 proximally and mesh 140 distally can be arranged as shown in FIG. 2 so that no portion of it is located within the right carotid artery 26R. In other exemplary embodiments, some portion of the occluding catheter 37 and corresponding part of mesh may be located within the right carotid artery 26R. A segment 44 of the shaft 104 that is located between the proximal and distal occluding balloons 38, 42 may be of a variable length, proportional to the distance between the orifices of the innominate 41 carotid 26 and subclavian 23 arteries and may be located in the aortic arch 22.

The occluding catheter 37 may be inserted into the right subclavian artery 23R via right radial, brachial, axillary or subclavian artery approach and can be advanced under fluoroscopic and arterial blood pressure guidance into the innominate artery 41, aortic arch 22 and left carotid artery 26L. The ideal position of the proximal tip of the distal occluding balloon 42 and its corresponding expanding mesh power 140 may be in the proximal segment of the left carotid artery 26L, whereas the proximal occluding balloon 38 with its mesh 130 may reach the level of the innominate artery 41.

The insertion of the occluding catheter 37 may be performed when both the proximal 38 and distal 42 occluding balloons are deflated and their corresponding mesh covers 130 and 140. However, once the distal occluding balloon 42 reaches the level of the aortic arch 22 it can be inflated to facilitate its advancement into the left carotid artery 26L. The inflated distal occluding balloon 42 is thus naturally propelled forward into the left carotid artery 26L by arterial blood flow. The adequacy of the position of the distal occluding balloon 42 is confirmed with fluoroscopy and, if desired, by appearance of the dampened arterial pressure recorded from the end pressure measurement channel 70 through the end pressure measurement port 50 with its distal tip opening 56 located distal from the tip of the distal occluding balloon 42 and inside the area covered by the mesh cover 140 downstream from the area of occlusion of the left carotid artery 26L.

Figure 5:
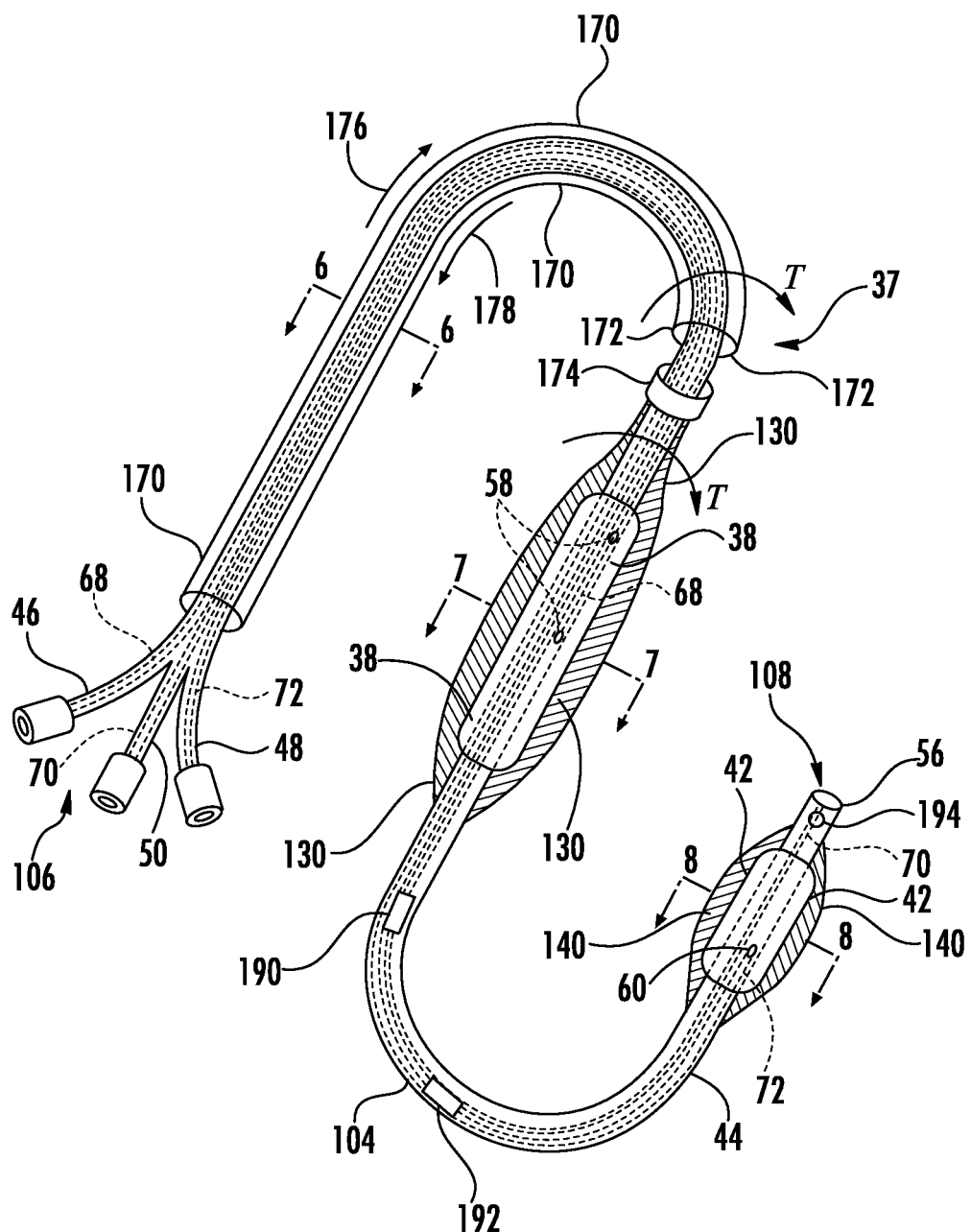
FIG. 5 is a front view of an occluding catheter in accordance with an alternative exemplary embodiment in a deflated state.
Figure 5A:
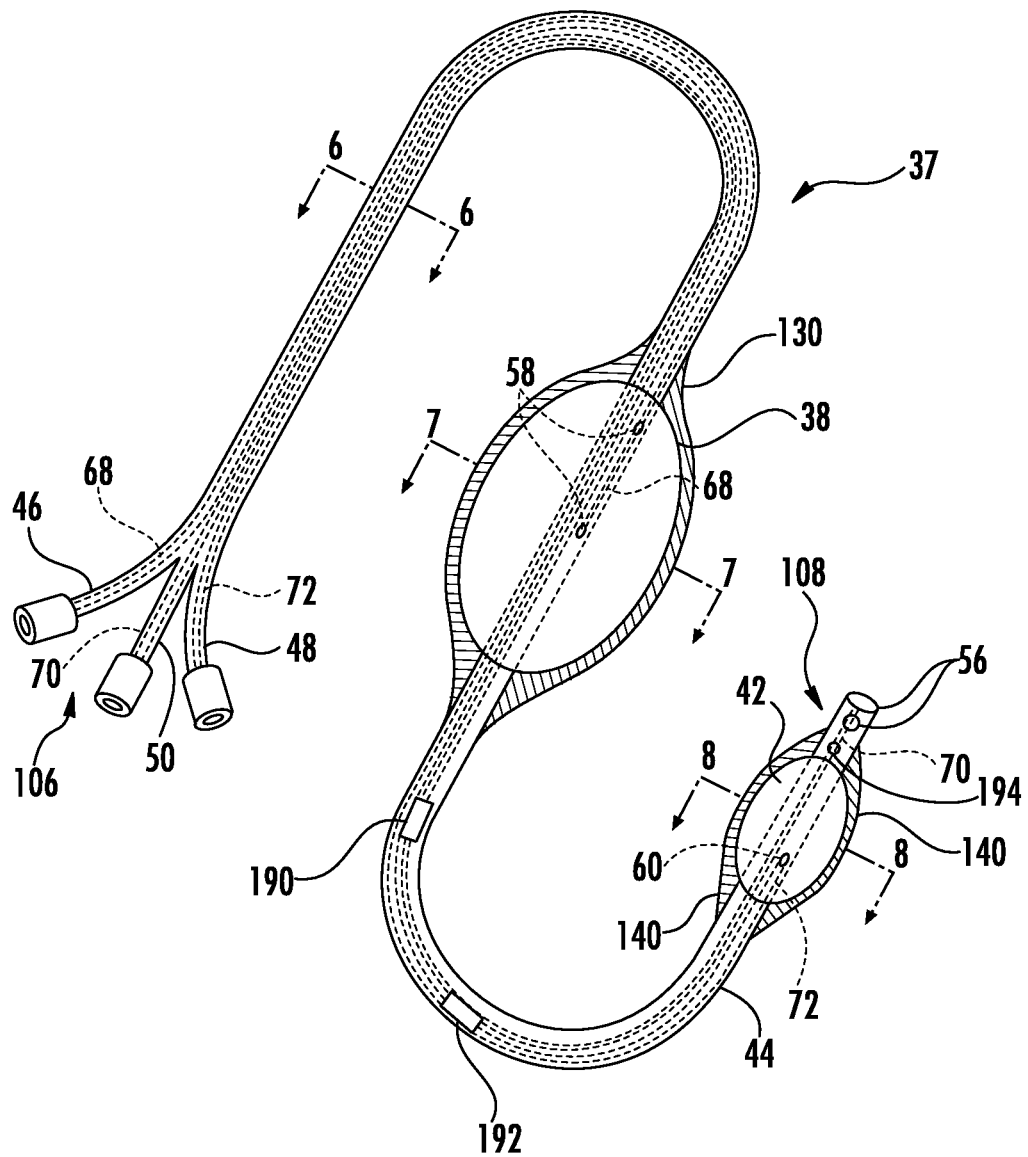
Figure 5B:
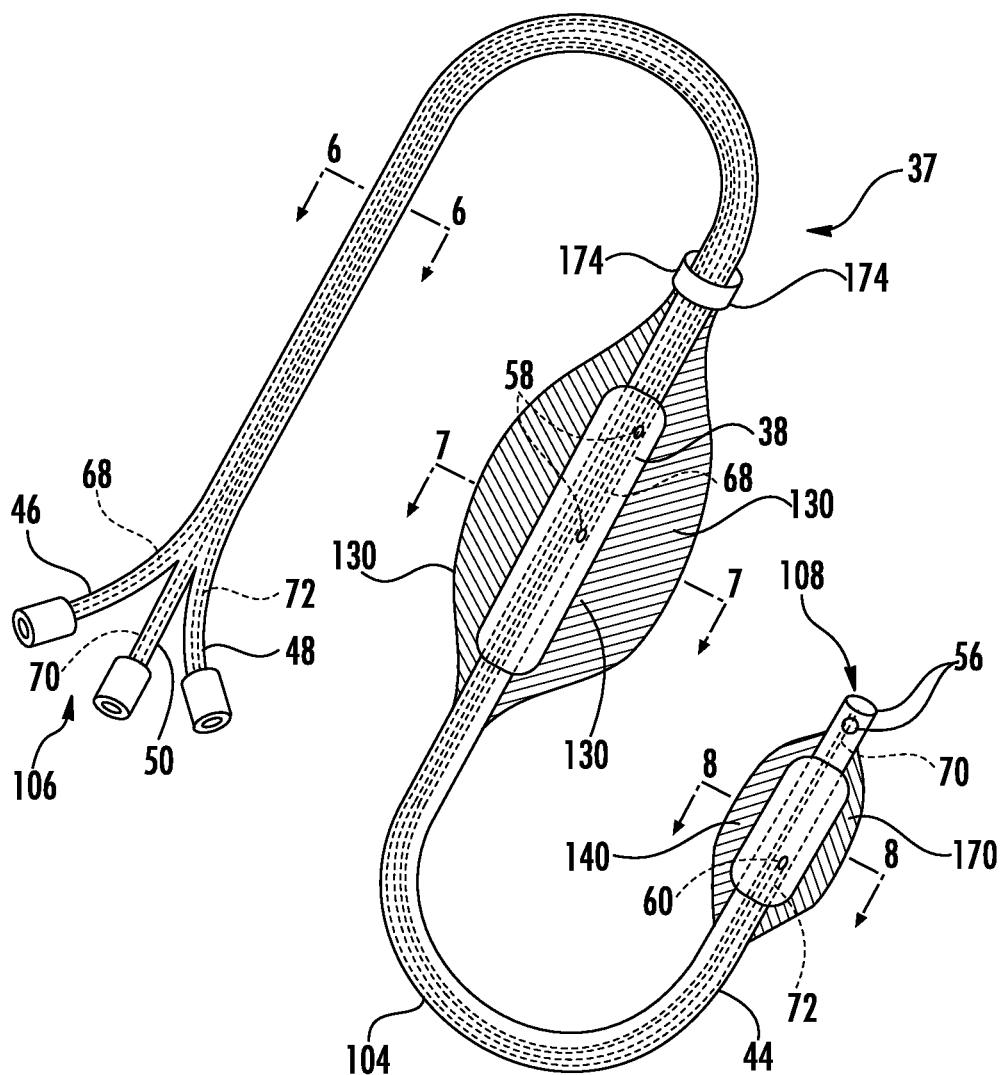
Figure 5C:
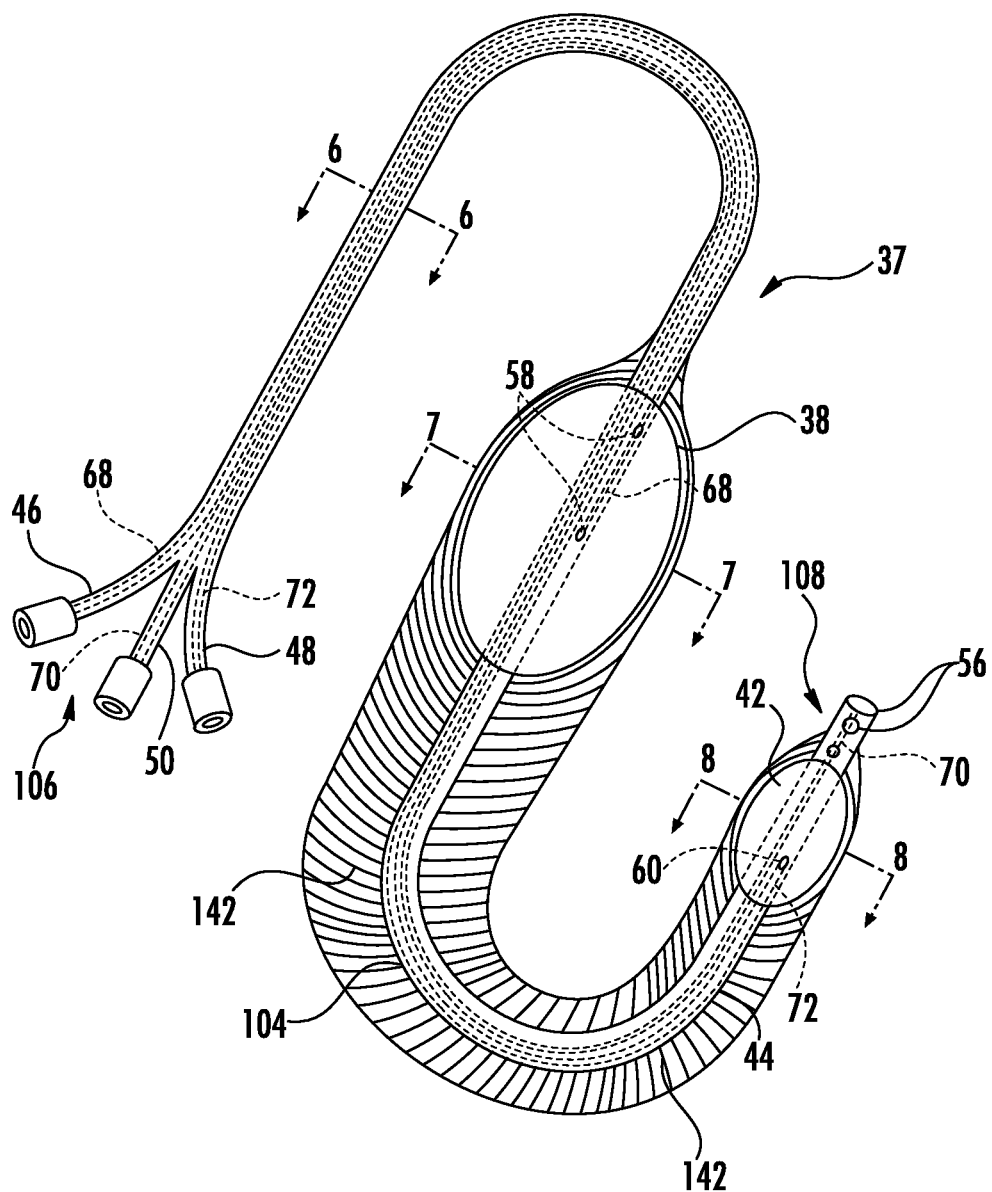
Figure 5D:
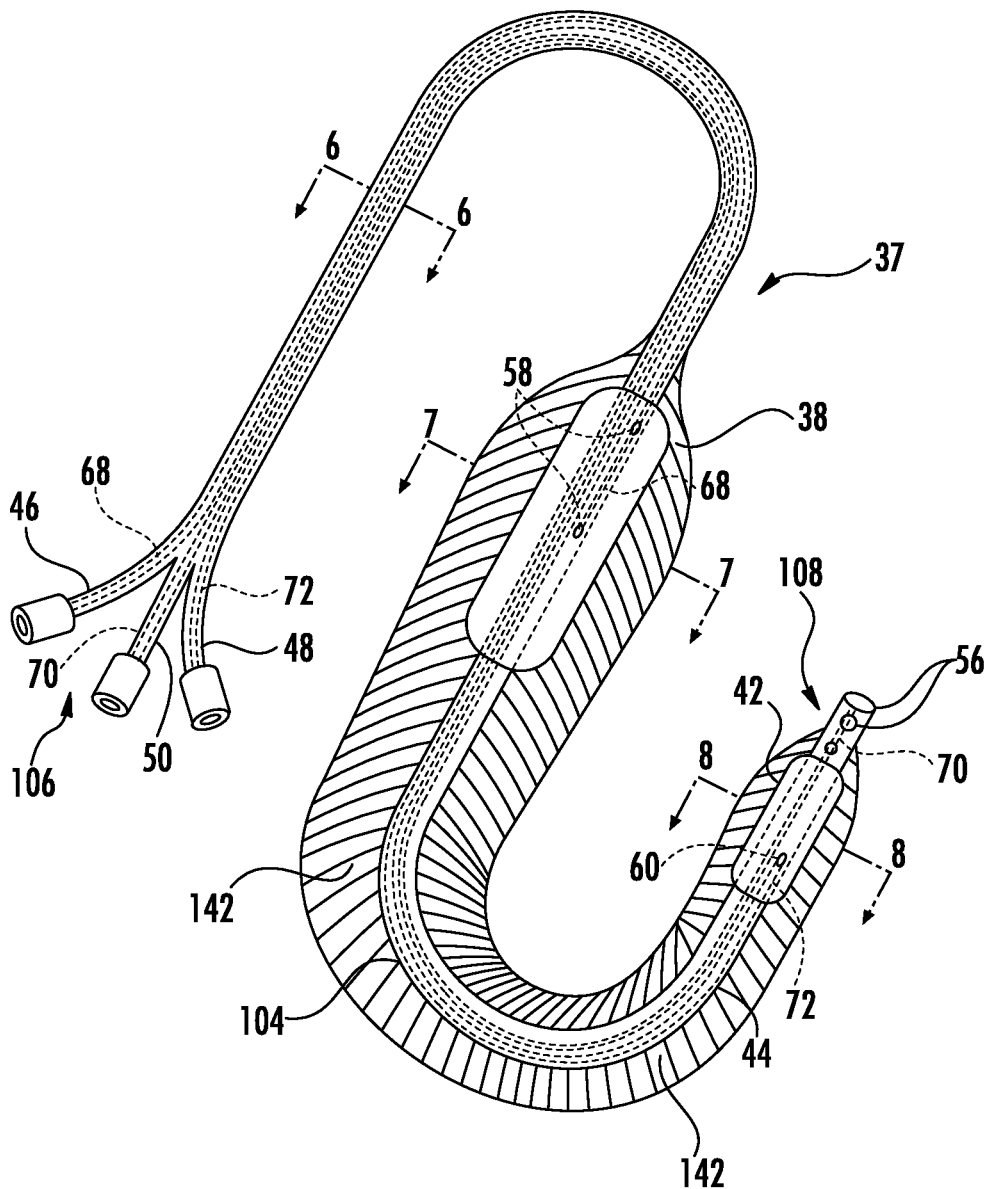

Once an adequate position of the distal occluding balloon 42 in the left carotid artery 26L is achieved it may be deflated. A normal arterial blood pressure waveform as recorded from the distal tip opening 56 should reappear to confirm adequate perfusion via the left carotid artery 26L. Once the balloon is deflated the mesh 140 may stay expanded or be singed and collapsed around the balloon by advancing an optional outer sheath 170 in the direction 176 over the catheter 37. Alternatively, both the balloon 42 and its expandable mesh cover 140 can be collapsed by pulling back the occluding catheter 37 into an optional sheath 170 in the direction 178 (FIGS. 5, 5-G, 5-H and 5-I). This process may be facilitated by using a collapsible material and folding configuration using premade longitudinal folds along the tissue of the balloon and of its outer mesh.

Correct placement of the distal occluding balloon 42 and the filtering mesh 140 within the left carotid artery 26L may result in correct placement of the proximal occluding balloon 38 and its filtering mesh 130 within the innominate artery 41. This is achieved by choosing an occluding catheter 37 with the longitudinal length of segment 44 between proximal and distal occluding balloons 38, 42 to be slightly larger than the distance between the left carotid artery 26L and innominate artery 41 as estimated by preoperative CT scan. According to some measurements, an optimal length of segment 44 should be 2-6 cm longer than the distance between the innominate artery 41 and the left carotid artery 26L to allow for a smooth turn of the inter-balloon portion of the occluding catheter 37 within the aortic arch 22. Considering the fact that the average distance between the orifices of the innominate artery 41 and left carotid artery 26L in the normal aortic arch 22 configuration is from 0.5-4.0 cm, the length of segment 44 between the distal and proximal occluding balloons 38 and 42 should lie within the range between 3 and 8 cm. Therefore, in practice several different sizes of the occluding catheter 37 can be constructed where the length of the segment 44 between the proximal 38 and distal 42 occluding balloons vary from 3 to 18 cm. The diameter, volume and length of the occluding balloons 38, 42 may also vary according to the patient's anatomy with the proximal occluding balloon 38 being 50-100% longer and larger than its distal 42 counterpart. Similarly, the diameter, volume and length of mesh 130,140 may also vary accordingly and may exceed the corresponding parameters of the balloons 38, 42. In addition both the balloons 38, 42 and mesh 130, 140 may have a certain degree of stretchability in the range of 0-50% in some embodiments when pressurized and/or subjected to an axial traction, bending and rotation. In other embodiments, however, the degree of stretchability may exceed 50%.

The length of segment 44 may be selected so that the proximal occluding balloon 38 and its mesh 130 is located within the innominate artery 41 at the same time that the distal occluding balloon 42 and its mesh 140 is located within the left carotid artery 26L.

The next step in the method of using the occluding catheter 37 may be the inflation of the proximal occluding balloon 38 in the lumen of the innominate artery 41 with an expansion of mesh 130 and recording of post-occlusion pressure in the distal innominate artery 41. This pressure may be recorded via an opening 54 of the shaft 104 located downstream from the proximal occluding balloon 38, yet inside the mesh 130 in the direction of arterial blood flow.

Figure 4A:
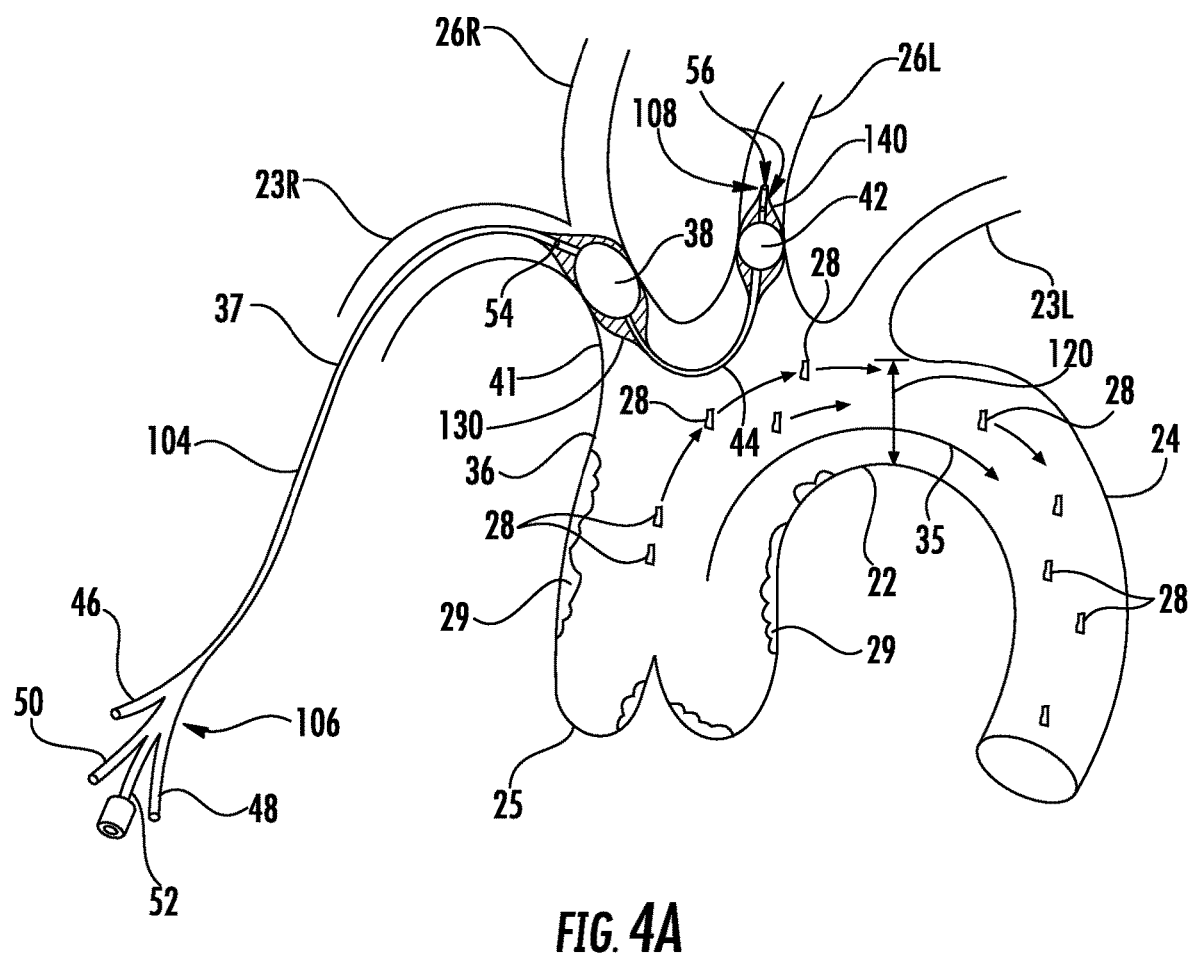
FIG. 4-A is a front view of the patient of FIG. 3 that shows the deflection of emboli into descending aorta, preventing their entry into carotid arteries when the occluding balloons are inflated.
Figure 4B:
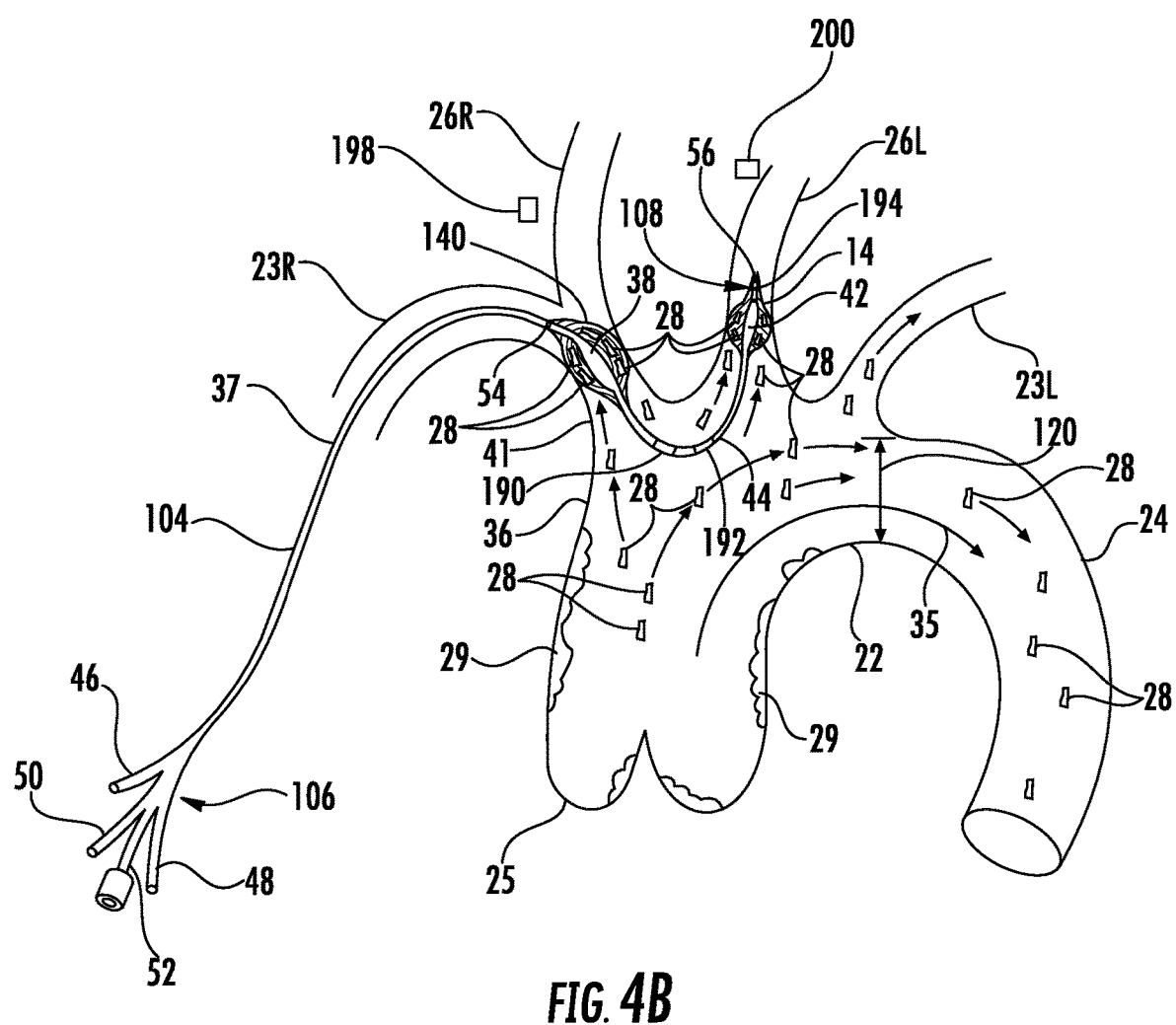

An intermediate pressure measurement and/or emboli aspiration channel 74 is in communication with the opening 54 and with an intermediate pressure measurement and/or aspiration port 52 at the proximal end 106. This port 52 can be used to confirm an adequate position of the proximal occluding balloon 38 by the appearance of the dampened waveform, plus—to aspirate the emboli 28 that are trapped inside the mesh 130. There may be a plurality of ports 52 connected to channel 74 to facilitate aspiration of emboli trapped inside the mesh 130 or simply passing through, when the balloon 38 is deflated. Channel 74 may serve for both pressure measurements and aspiration of the emboli 28. Once the pressure measurement indicates that the proximal occluding balloon 38 is properly positioned, the proximal occluding balloon 38 can be deflated and the occluding catheter 37 is considered ready for use. At this point mesh 130, 140 may be expanded to start the process of filtering the blood flowing to the carotid and, if needed, the vertebral arteries. The degree of interruption of carotid flow or pulse, as well as the changes in the lumen of the vessel and the number of embolic particles passing through may be assessed by Doppler ultrasound probes 198, 200 or 190, 192, 194 (FIGS. 1, 2, 4-B, 5, 5-A, 9-A,B). Ultrasound vascular probes 198, 200 may be located outside the carotid artery 26 on the neck surface (FIG. 1, 4-B), while intravascular probes 190, 192, 194 are located inside the artery 26, 41, or 23 mounted on the catheter 37 (FIGS. 2, 4-B, 5, 5-A, 9-A and 9-B). Probes 194 may be located on the distal segment of the catheter 37, while probes 190 and 192 may be located on the proximal and intermediate segments of the catheter 37 respectively (FIGS. 2, 4-B, 5, 5-A, 9-A and 9-B). The vascular probes may vary in their ultrasonic characteristics in terms of the frequencies, wavelengths, angles of insonation and ultrasound modes, creating a possibility of obtaining simultaneously a variety of real time data, comprising blood velocity, B-mode images, embolic signals (high intensity transient signals) etc., i.e.—a plurality of parameters reflecting the vessel blood flow, condition of the arterial wall and its lumen, the appearance of embolic particles, their number, composition and size, directional movement and the potential for cerebral embolization. This catheter arrangement will provide a unique combination of data that will allow to both detect the appearance of emboli 28 in a bloodstream, and to assure an immediate protection from their entry into the head vessels 23, 26 by virtue of either deflection of such emboli by the inflated balloon or filtering and trapping of emboli by expanded mesh when the balloon is completely, or partially deflated. In addition said probes may be preset for sequential registering of the path, speed and direction of propagation of the particles in relation to the shaft of the catheter and surrounding arterial structures by virtue of synchronous assessment of ultrasonic signals obtained simultaneously from Doppler probes 190, 192, 194, located throughout the occluding catheter. A processing software may be used to assess the direction of embolic particles 28 as to whether they are moving towards the head arteries 41, 26, 23, or away from said arteries and into the distal aortic arch 22 and the descending aorta, thus providing an important information regarding a potential embolic insult to the brain. Such information may be directly transferred to the processing and alarm center 114 in order to signal the incoming embolic threat and optionally trigger the process of balloon occlusion or filtration of the blood flow to the head vessels 41, 26, 23.

In addition, the degree of arterial compression and the amount of residual cerebral flow can be measured by the arterial pressure and waveform patterns distal to the level of occlusion in accordance with certain exemplary embodiments.

Figure 3A:
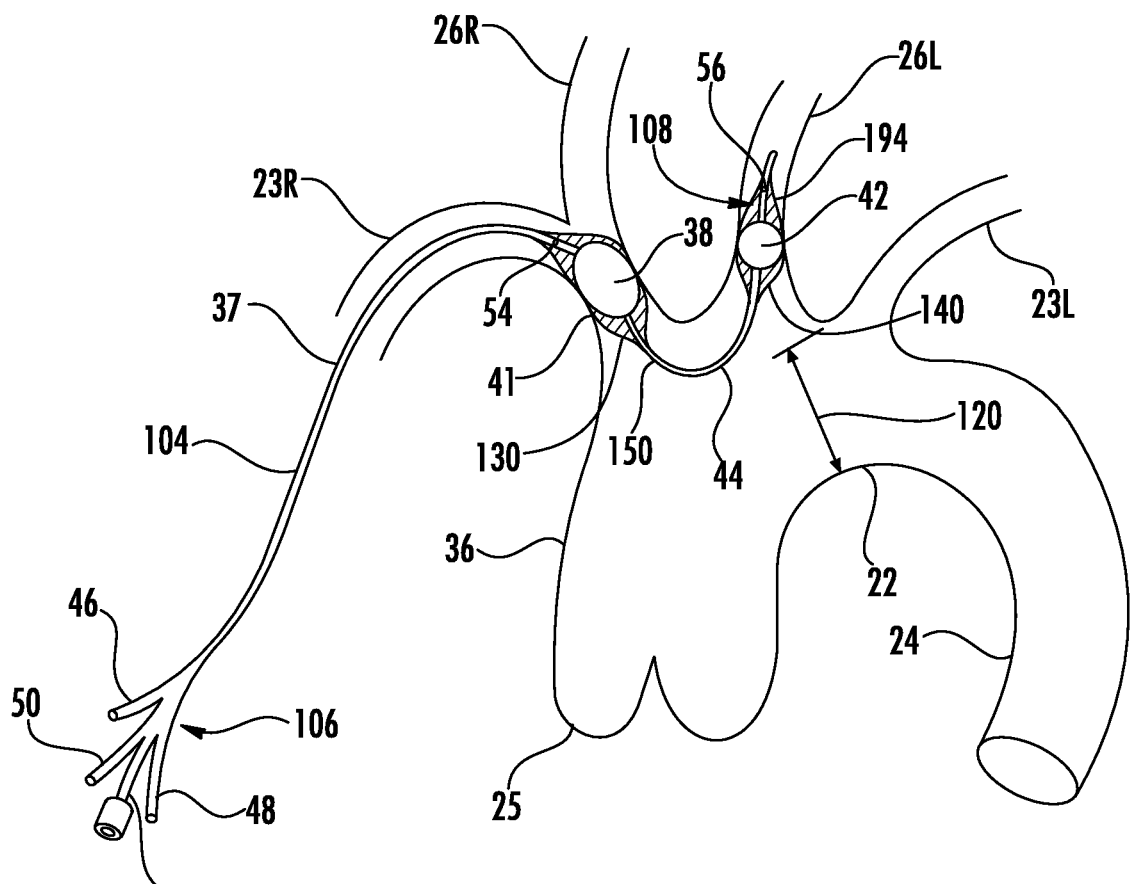
FIG. 3-A is a front view of the patient of FIG. 2 with the occluding catheter in an inflated state.
Figure 3B:
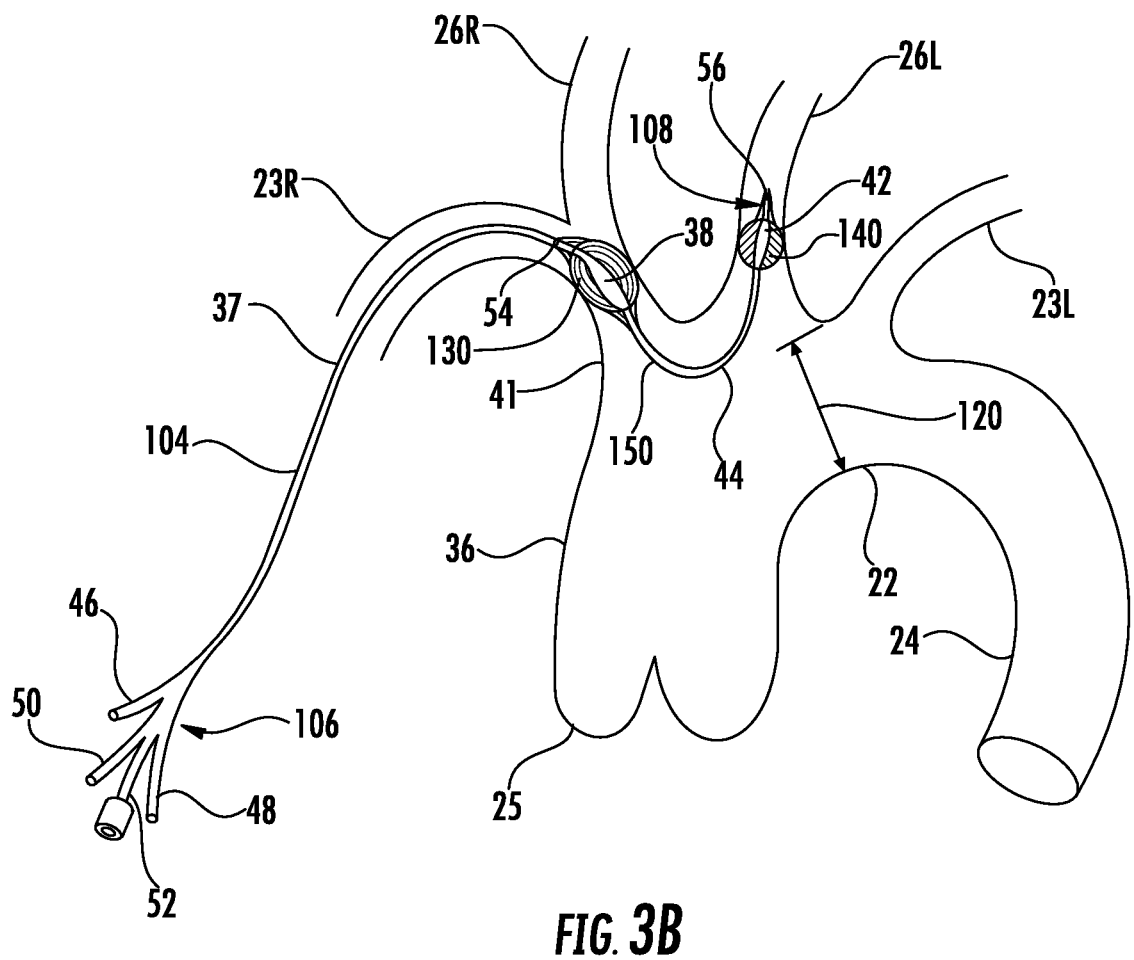

The proximal and distal occluding balloons 38, 42 may be inflated such that they are both inflated at the same time as shown with reference to FIG. 3-A. Simultaneous inflation may lead to temporary interruption of the carotid arterial flow, preventing all potential emboli 28, released due to manipulations on atherosclerotic calcified plaques 29 of the ascending aorta 36 (or from other such emboligenic events) from entering the cerebral circulation, and diverging them downstream from the cerebral circulation into the descending aorta 24, thus protecting the patient from embolic stroke. The occluding balloons 38, 42 may be inflated to such a pressure and be of such a resiliency that they completely block any blood flow past them and through the particular artery or arteries into which they are positioned. A complete occlusion of the head vessels, however, cannot last for a long time as it may induce brain ischemia due to interruption of a blood supply. This problem can be avoided by partial or complete deflation of the balloons 38, 42 while leaving the filtering mesh 130, 140 still expanded in the lumen of the innominate and carotid arteries as it is presented in FIG. 3-B. In this case a plurality of arrangements is are possible where a desired amount of blood flow may be allowed past the deflated proximal occluding balloon 38 and/or the deflated distal occluding balloon 42, while achieving a filtering, trapping and deflecting effect of the expanded mesh 130 and 140 (FIGS. 4-A and 4-B).

For example, FIG. 4-A illustrates the flow of blood in the circulatory system upon inflation of the proximal and distal occluding balloons 38 and 42 with the full expansion of proximal and distal filtering mesh 130 and 140. Temporary interruption of flow at the level of the proximal carotid arteries 26R, 26L leads to divergence of blood flow 35 carrying all potential cerebral emboli 28 into the descending aorta 24. Emboli 28, diverted from cerebral circulation move through the descending aorta 24. The proximal occluding balloon 38 may completely block the innominate artery 41 so that no blood flow or emboli 28 may be transferred to the right carotid artery 26L and the right subclavian artery 23R. The position of the proximal occluding balloon 38 can be made so that it is right at the bifurcation of the innominate artery 41 in order to completely occlude the orifice of the right carotid 26R and right subclavian 23R arteries at the same time. Both distal and proximal occluding balloons 38, 42 are inflated just before proceeding with the part of the procedure prone to generate cerebral emboli 27. This may be the placement or removal of an aortic cross clamp, implantation of valves, endovascular grafts and stents, or other procedures outlined above.

Inflation of the occluding balloons 38, 42 can be such that they are inflated to a pressure exceeding the patient's systemic pressure by 10-50 mm Hg or more just before proceeding with the emboligenic part of the procedure. Insertion of the occluding catheter 37 through the right side and inflation of the proximal occluding balloon 38 at the level of the innominate artery 41 may preclude entrance of emboli 28 into the right subclavian artery 23R and right vertebral arterial system. Insertion of the occluding catheter 37 through the left side of the patient may cause the proximal occluding balloon 38 to be at the level of the left subclavian artery 23L to preclude entrance of emboli into the left subclavian artery 23L and vertebral arteries, further reducing the risk of emboli entrance and stroke. The distal and proximal occluding balloons 38, 42 may be inflated for an approximate period of 15-180 seconds after the emboligenic part of the procedure is performed to achieve complete washout of all potential emboli 28 into the descending aorta 24 and distal vasculature, while avoiding migration of emboli 28 into the carotid arteries 26R and 26L.

Then, however, the distal and proximal occluding balloons 38, 42 may have to be deflated in order to reinstitute an adequate blood flow to the brain and to avoid an ischemic brain injury. This problem, however, can be resolved by leaving the filtering mesh 130 and 140 in the expanded state inside the lumen of the innominate and carotid arteries. In this embodiment the deflation of the balloons 38, 42 will create an adequate space for the blood to flow around the balloons and through the filtering mesh, leaving the potential cerebral emboli 28 either trapped or deflected by the mesh 130, 140 (FIG. 4-B). Such mesh cover, as depicted in FIGS. 4-B, 9-C, 10-C, 12-B, 13-B, 13-C, 14-A, 14-B and 15, has a proximal segment, an intermediate segment and a distal segment, comprising a cranial side 154 of the mesh facing the craniad area 156 of the aortic arch 22, containing the orifices of the head vessels 41, 26, 23;

a cardiac side 152 of the mesh facing the heart 21, ascending aorta 36 and the opposite (caudad i.e. opposite to the area 156) side of the aortic arch 22; and an intermediate side 158 of the mesh facing the vessel structures that are not faced by the cranial 154 and the cardiac 152 sides of the mesh.

Figure 12A:
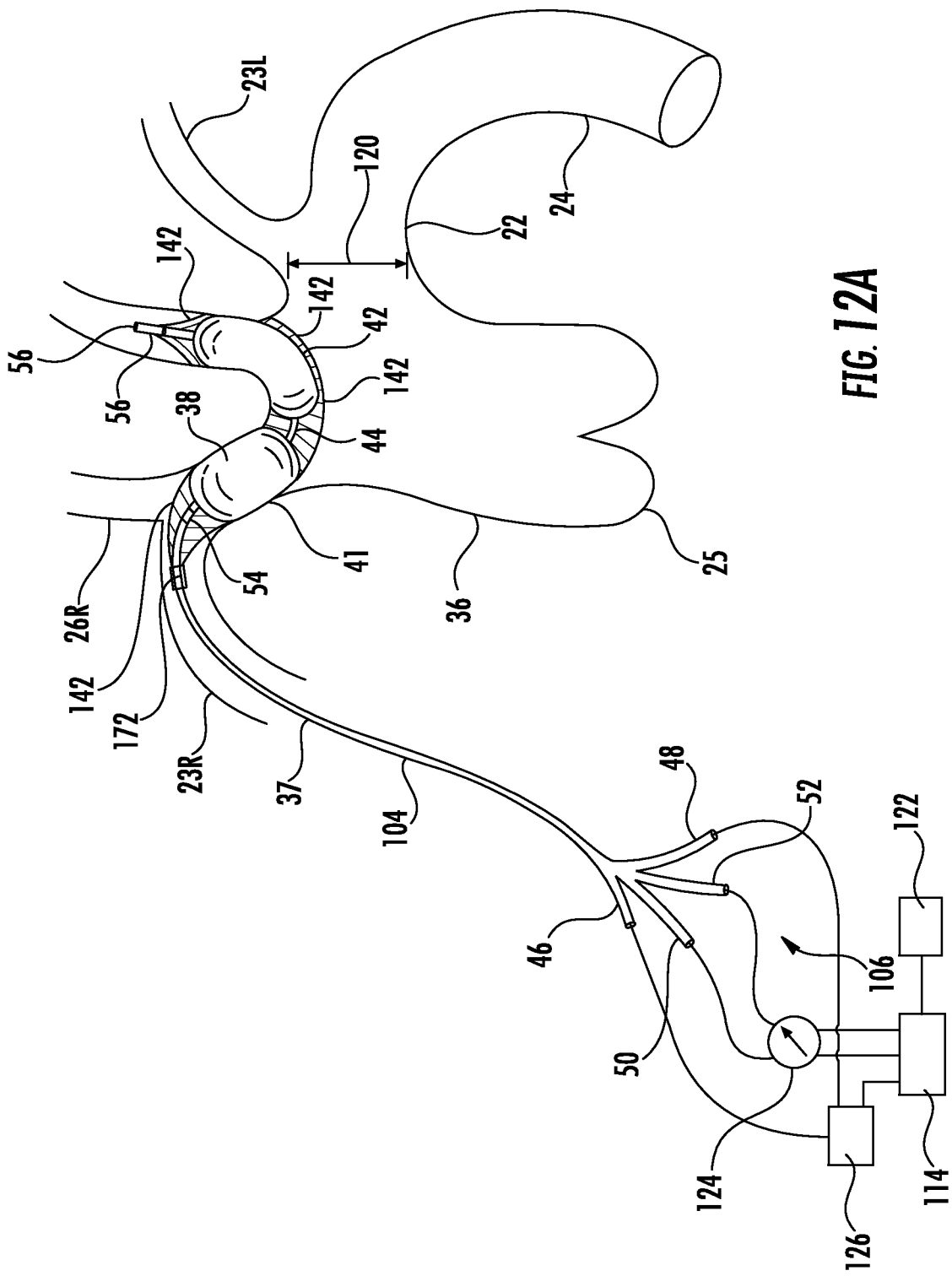
FIG. 12-A is a front view of the patient with an inflated occluding catheter and of FIG. 11-A and an alarm system in accordance with a further exemplary embodiment.
Figure 12B:
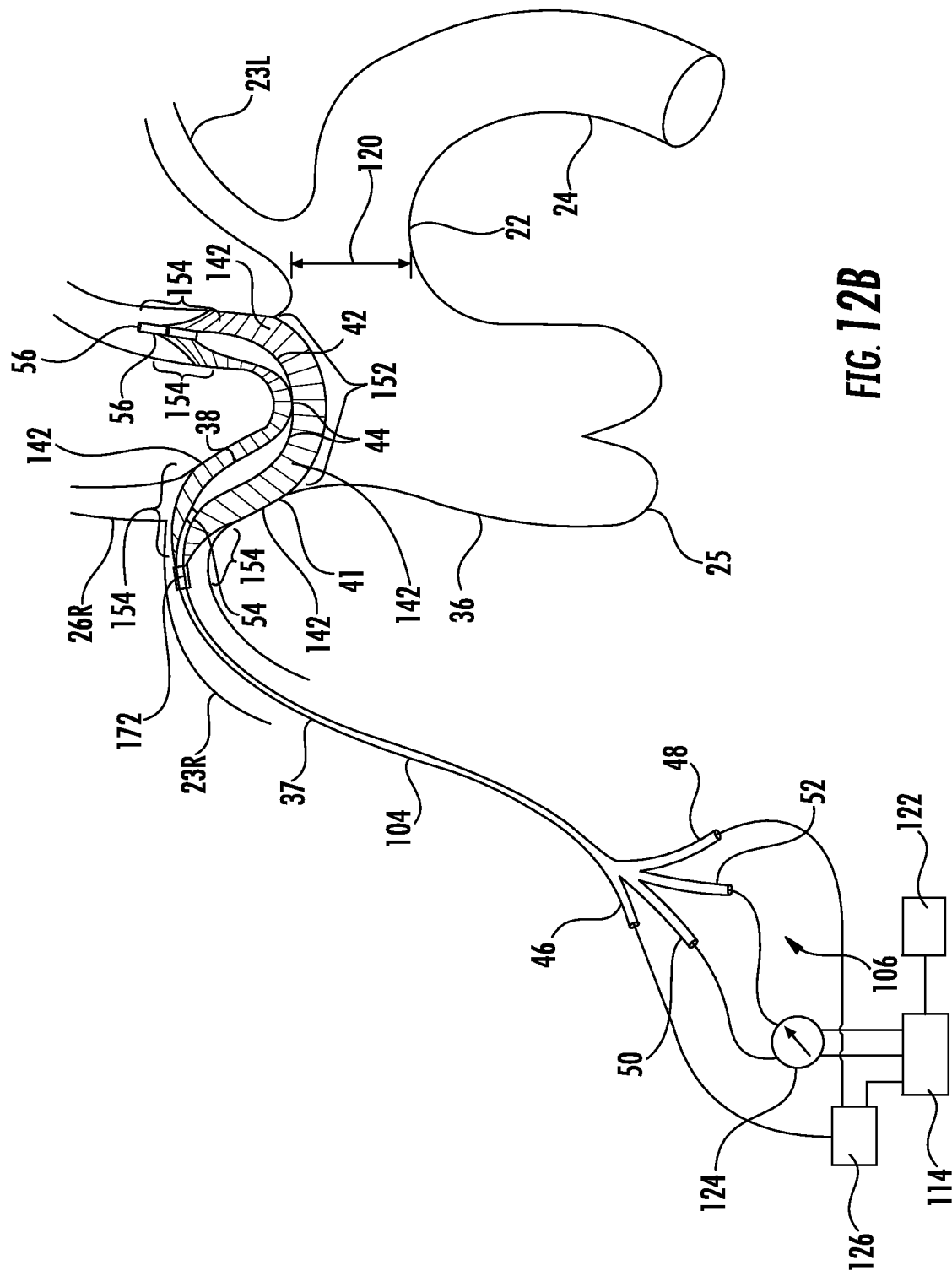

As shown on FIGS. 9-C and 10-C the cranial area 154 of the mesh 142 may have a proximal end (154-P), a distal end (154-D) and an intermediate end (154-M). Similar arrangement may exist for mesh 130, 140 and 150. The proximal part 154-P of the mesh when actuated by inflation and subsequent deflation of the proximal occluding balloon 38, will cover the lumen of the innominate artery 41 and protect the orifices of the right subclavian artery 23R and right carotid artery 26R (FIG. 12-A,B; 14-A,B). Similarly, the distal part 154-D of the mesh when positioned in the orifice 92 of the left carotid artery 26L (FIGS. 3, 4 and 12) or in the orifice of the left subclavian artery 23L (FIGS. 13, 14) after its expansion by inflation the balloon 42 (FIGS. 3, 4) or balloon 38 (FIGS. 13, 14) and after subsequent deflation of said balloons, will cover the orifice 92 or both orifices 92 and 98 (depending on the particular embodiment) and protect the arteries 26L and 23L from possible emboli.

As shown in FIG. 4-B, the emboli 28, entering the innominate and left carotid arteries 41, 26L will face first the area 152 and/or area 158 of the filtering mesh. The mesh is configured in such a way that while the area 152 is acting as a $1^{st}$ barrier on the way of emboli to the brain, facing the incoming arterial flow carrying emboli 28 from the heart and aorta, the area 154 of the mesh is located on the opposite side of the mesh, facing the head vessels 23, 26 and 41 and acting as a $2^{nd}$ barrier on the way of emboli, receiving the flow of blood that has already passed through the area 152. In some embodiments there also may be an intermediate area 158 of mesh 130, 140, 142 and 150. As the result, the incoming blood entering the mesh through the area 152 and carrying potential cerebral emboli 28 will have to exit the mesh through the area 154 before reaching the arteries 23, 26 and entering the brain circulation.

In addition, in some embodiments the size of pores in the areas 152, 154 and 158 may be unequal in such a way that the pores 180 of the "cardiac" mesh area 152 are larger pores ranging from 150 to 500 in the relaxed state of the mesh, while the pores 182 of the "cranial" mesh area 154 may be smaller in the range of 50-250 micron and the pores 184 of the mesh area 158 are of intermediate size in the range between 150 and 350 micron. The pore size of each area may vary depending on the embodiment and the procedure performed and represents the initial size of pores at the relaxed (i.e. neutral) state of the mesh, when no forces are applied to the mesh. However, in some embodiments, the pore size may be changed within the same embodiment by being adjusted using the structural features of the catheter 37, an extra guidewire and/or the outer sheath 170 attachable to the filtering mesh 130, 140, 142 and 150 by virtue of a locking mechanism 172-174 such as Luer-Lock, screw-in connection, wedging, tight coaxial connection etc. Such features allow for the mesh to be actuated i.e. expanded, elongated, stretched, twisted, torqued, bent and/or undergo any combination of these maneuvers in order to affect the size of the pores filtering the incoming (area 152) and outflowing (area 154) blood. Such changes may allow to selectively adjust the filtering capacity of the areas 152, 154 and 158 of the mesh and to modify the filtering capacity of the mesh as a whole.

Figure 17A:
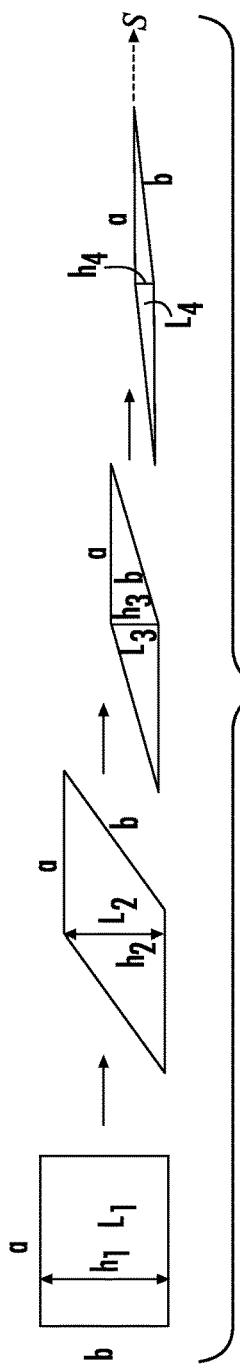
FIG. 17-A is a front view of a lumen of a pore of a filtering mesh in accordance with another exemplary embodiment starting with a neutral position $L_1$ subsequently diminishing the lumen of a filtering pore after applying an axial traction along the side "a".
Figure 17B:
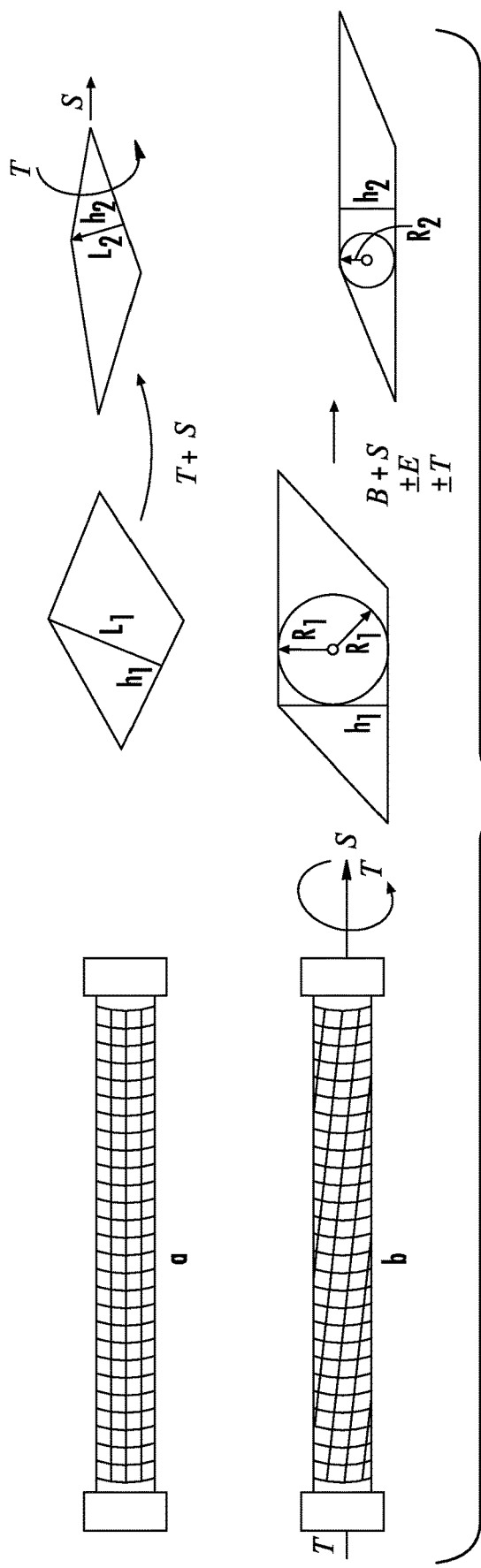
Figure 18:
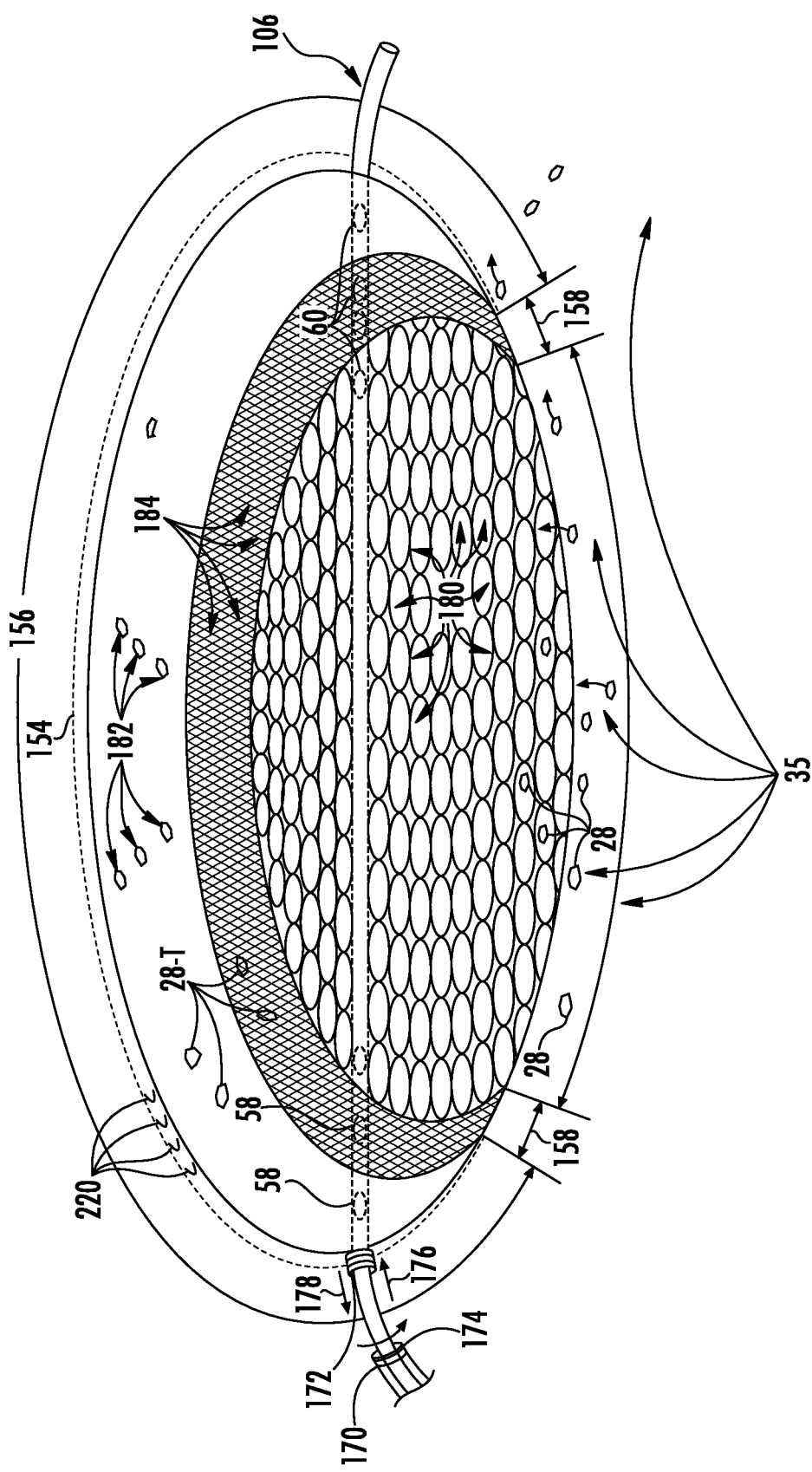
FIG. 18 is a front view of another embodiment of a filtering mesh in an expanded configuration after the occluding balloon has been deflated showing the areas of filtering pores of a variable size with the emboli partially deflected and partially trapped inside the mesh.

As shown in FIGS. 16 and 17, the size and shape of pores in the mesh may be adjusted before and during the procedure depending on the degree of their expansion, elongation E, compression C, traction, stretching (S), bending B and torqueing (T). These processes while applied separately, or in combinations, will lead to certain deformation of the mesh pores leading to shortening or elongation of the minimal diagonal dimension $d_1$ or $d_3$ decreasing or increasing the pore size and radius R in relation to its initial dimension before any external forces are applied to the mesh (i.e. neutral or "relaxed" state of the mesh). The actuated state of the mesh leading to changing of the pore size and shape may be achieved by using the disclosed structural features of the occluding catheter 37 such as a different degree of the balloon expansion, outer sheath 170 advancement in the direction 176 or traction in the direction 178, with the mesh extension (E), elongation or compression, stretching (S), axial rotation (T) and bending (B) of the mesh by means of such actions applied to the outer sheath 170 and/or a catheter, or wire that may be releasably attached to the proximal segment of the mesh via a slidable ring 174 by the locking mechanism 172-174. For example, pulling back on the outer sheath 170 in the direction 178 once it is connected to the mesh via the locking mechanism 172-174 and while the catheter 37 is remaining in its initial position with the distal segment of the mesh attached to the distal segment of the catheter 37, may first elongate the mesh pore depicted in FIG. 16-A in a horizontal direction with the resultant elongation of the diagonal $d^1$ to $d^4$ and shortening of the diagonal $d^2$ to $d^3$ as depicted in FIG. 16-B. In this case, if the length of the sides "a" does not change, the mesh pore would elongate, but not stretch. However, if further traction on a sheath 170 in the same direction 178 is applied, it may lead to stretching S in the direction along the long axis of the catheter 37 as depicted in FIGS. 16-C and D with stretching of the side "a" and horizontal diagonal "d" in addition to previous elongation from $d^2$ to $d^4$. As a result, the horizontal (longitudinal) diagonal dimension will further elongate from $d^4$ to $d^6$ (FIG. 16-C) and from $d^6$ to $d^8$ (FIG. 16-D). These changes will be associated with the proportional shortening of the vertical diagonal dimension $d^2$ to $d^3$, $d^5$ and $d^7$ ($d^2<d^3<d^5<d^7$) and the radius R of the circle, inscribed in the rhombus (or parallelogram) depicted in FIGS. 16-A,B,C and D, leading to proportional increase in the pore filtering capacity ($R_1>R_2>R_3>R_4$). As a result, any particle with the radius smaller than the radius $R_1$ of a pore, depicted in FIG. 16-A, will be able to pass through the pore depicted on FIG. 16-A, while it will not be able to pass through the elongated or stretched pores of FIGS. 16-B, C and D, while the area of the pore may remain unaffected and, therefore the flow through such pore will not decrease. Similarly, a particle X with the diameter of the inscribed circle smaller than $d^3$, but larger than $d^5$ or $d^7$ (or: $R_4<R_3<R_x<R_2$) will not be able to pass through the pores shown on FIGS. 16-C and D, but will be able to pass through the pores of FIGS. 16-A and B. An example of a diminishing pore permeability for embolic particles after the traction force T that is applied along the top side "a" is demonstrated on FIG. 17-A, where in spite of a preserved area of the lumen L, the vertical dimension h of the pore is being diminished decreasing the ability of embolic particle to pass through ($h_1>h_2>h_3>h_4$). Considering the fact the blood flow through such pores will depend on the area of the lumen L that does not change in spite of a change of a vertical diameter ($L_1$ equals $L_2$, $L_3$, and $L_4$, i.e. $L_1=L_2=L_3=L_4$) such increase in a filtering capacity will not compromise the blood flow to the brain while providing the most efficient protection from incoming emboli. As shown on FIG. 17-B, an additional improvement in filtering capacity of the mesh may be achieved by a torqueing deformation T of the filtering mesh "a" along the arrow T leading to both elongation and stretching S of the filtering pores producing the appearance of the mesh "b" of FIG. 17-B with the resultant lumen $L_2$ that may become smaller than the lumen $L_1$. Such torqueing T and/or stretching S is produced by rotation T and outward traction force 178 applied to the outer sheath 170, guidewire or a catheter attached to the sliding ring 174 of the mesh cover via a locking mechanism 172-174 (FIG. 18). Said rotation and traction may be performed around the central longitudinal axis of the disclosed occluding catheter and the filtering mesh. The direction of the torqueing force T and/or stretching force S is shown by arrows T and S as depicted in FIG. 17-B. Such deformation of the mesh pore may be augmented by applying a bending force B and extension force E as depicted in the FIG. 17-B with the resultant decrease of the mesh pore height "h" ($h_1>h_2$) and the radius R of the inscribed circle ($R_1>R_2$)

On the other hand, if we assume, that the initial pore size and shape before any forces to the pore are applied (i.e. a "neutral" pore position and shape) is similar to the pore of FIG. 16-B, than such mesh may be compressed along the longitudinal axis $d_2$ resulting in increasing of its diagonal dimension $d^3$ to $d^2$ and shortening of the diagonal $d_4$ to $d_1$ with the resultant increase in the radius $R_2$ of the inscribed circle to $R_1$, as depicted on FIG. 16-A. As a result the diameter or the radius R of the particle being able to pass through the pore of FIG. 16-A will be bigger with a possibility of the flow increase through the same pore due to diminishing of the cavitation effect that may develop if the pore size is too small. Further compression and/or torqueing of the pore of FIG. 16-A along the same longitudinal axis $d_1$, however, will produce progressive shortening of $d_1$ with a subsequent increase in filtering capacity of the mesh.

These arrangements are important for the health care provider in order to either increase or decrease the filtering capacity of the disclosed mesh depending on the degree of the embolic load and the need to augment the blood flow through the mesh as any filtering of blood flow to the brain is invariably associated with a proportional decrease in the blood flow to the brain, thus increasing the risk of brain hypoperfusion and ischemic injury. For example, in case when the expected or detected embolic load is high the mesh pore size can be minimized by the maneuvers, mentioned above, whereas when the embolic threat is minimal, the pore size can be augmented in order to proportionally increase the flow of blood to the brain. In some embodiments this process can be automated by coupling the information obtained from the vascular probes 190, 192, 194, 198 and 200 with the device attached to the outer portion of the catheter 37, guidewire and/or sheath 170 that would elongate, rotate, stretch, bend and/or mix and reverse these changes.

According to the laws of hydrodynamics, upon entering into the contact with the mesh the embolic particles will undergo scattering and turbulence, leading to a significant loss of their momentum and alteration of their trajectory that was initially directed to the brain. As a result, some of these particles may stay trapped inside the mesh, while others may get deflected and redirected into the descending aorta 35 and away from the cerebral circulation following direction of an arrow 44 (FIG. 4-B). The process of trapping of embolic particles 28 inside the mesh 130, 140 as well as the mesh 142, 150 and 160 is facilitated by the disclosed structural feature of a mesh with a variable pore size throughout the surface of the mesh, where the pores 180 are larger in the area 152 that is facing the arterial inflow from the heart and aorta, while the pores 182 in the areas 154 (facing the area 156 of the takeoff of the head vessels 41, 26, 23) are smaller and located on the opposite side of the mesh facing an area of arterial outflow (FIGS. 4-B, 13-C, 14-A, 15 and 18). In some mesh embodiments there may be an additional area 158 located in the intermediate zone of the mesh between areas 152 and 154. This area (an intermediate zone) is defined by pores 184 of intermediate size that are smaller than pores 180 and larger than pores 182. The emboli 28 ejected from the heart into the ascending aorta and aortic arch will first encounter the area 152 of the mesh ($1^{st}$ mesh barrier) and either would get deflected or enter the mesh through its larger pores 180. Next, emboli 28, while being propelled further with the blood flow through the mesh, will encounter the area 154, containing smaller pores 182 ($2^{nd}$ mesh barrier) that will provide further deflection and trapping of embolic particles. This disclosed feature provides for an additional deceleration, scattering, redirection and trapping of the embolic particles entering the mesh. Depending on the relative pore size of the mesh and the size of the emboli 28 such emboli, if they are smaller than pores 180, will either enter through the larger pores 180 and get trapped at the smaller pores 182 or will get deflected from the smaller pores 182 and intermediate pores 184 and leave the mesh through the pores 180 into the distal aortic arch and descending thoracic aorta to follow the direction of blood flow shown by arrow 44 (FIG. 4-B) i.e. away from the cerebral circulation. Even the very small emboli of a size smaller than the diameter of smallest mesh pores 182 (less than 50 micron) may not pass through the mesh as they will be trapped inside the mesh due to formation of turbulences and eddies and a loss of kinetic energy that would be necessary to propel the particle all the way to the brain through both $1^{st}$ (proximal) and $2^{nd}$ (distal) mesh barriers. As a result embolic particles 28 will either get trapped inside the mesh and to be subsequently retrieved using an outer sheath 17 advanced over the mesh and pulled out of the patient's artery, or will leave the mesh via the larger pores 180 of the area 152 or intermediate pores 184 of the area 158 and follow the direction of blood flow 44 away from the cerebral circulation and carotid arteries 23 (FIGS. 4-B, 18) thus decreasing the risk of cerebral embolization and stroke. These remaining embolic particles are usually harmless as they are prevented from entering cerebral circulation and their quantity (embolic load) and size are very small to induce an ischemic injury in any other organs located downstream.

The length of time while the filtering mesh needs to stay expanded may vary depending on the type and stage of the procedure. Once the occluding balloon is deflated and the filtering mesh remains in the expanded position, it may stay expanded to maintain its filtering function throughout the whole time of the procedure, or be temporarily or permanently removed, when necessary, or if the main emboligenic (i.e. generating emboli) part of the procedure is completed and the risk of additional emboli is negligible. In some embodiments, however, the mesh 130, 140, 142 or 150 may be disconnected from the occluding catheter and left expanded inside the aortic arch 22 and/or innominate and carotid arteries 41, 26 for a longer period of time (up to 2-4 weeks or longer) providing a long term protection from embolic particles that may be released hours or days after the procedure is completed. The process of fixation of the mesh inside the vessel is provided by several disclosed structural features such as a self-expanding feature of the mesh upon its release from the occluding catheter, hyperexpansion exceeding the diameter of the vessel by 5-30%, a helix, multi-helix, spiral and multi-spiral configuration of the mesh along its longitudinal and/or transverse axis, with an option of at least one, or in some embodiments—a plurality of compliant and optionally retractable fixation hooks 220 (FIG. 9-D and FIG. 18) on its surface located at the segment of the mesh that is in contact with at least one of the subclavian 23, carotid 26 or innominate 41 arteries. This mesh may be removed at a later date using a recapturing mechanism of the outer sheath 170 and the combination of the standard endovascular techniques including loops and forceps and trapping baskets.

In most of the embodiments the filtering mesh is made out of a compliant, yet able to recoil material such as metal (such as titanium, nitinol etc.), plastic or biopolymer (such as polyurethane, polypropylene, carbon fiber, fiberglass, polyester). In some embodiments, however, the mesh may be made out of a biodegradable material and may not require its removal as it will get naturally reabsorbed and gradually disappear.

The length of the complete or partial occlusion of the head vessels 41, 26, 23 achieved by the inflation of the balloons 38 and 42 may be either shortened or extended depending on multiple factors that comprise the timing of embolic events, their intensity and the degree of patient's tolerance to transient interruption of cerebral flow such as the degree of hypothermia and the condition of the collateral cerebral flow as measured by EEG, intravascular or carotid ultrasound using probes 190, 190, 194, 198, 200 with the detection of embolic particles, assessment of the vessel lumen and the blood flow, transcranial Doppler, echocardiography or other means.

The length of most manipulations associated with formation and transgression of cerebral emboli into cerebral circulation rarely exceed 1-2 minutes. Temporary interruption of the carotid flow for this period of time, plus 0.5-1.5 min to allow for complete washout of emboli 28 from the aorta 22 and upstream from the occluded arteries 41, 26, 23 is completely safe and feasible.

Partial deflation of said balloons may provide a necessary blood flow to the brain while still decreasing the degree of cerebral embolization. Once this brief period of time that is necessary for the washout of embolic debris is completed, both occluding balloons 38 and 42 may be fully deflated while the filtering mesh may stay expanded to assure a continuous perfusion of the brain while the residual embolic particles are deflected or trapped by the mesh. Said technology will allow to extend the length of cerebral protection from embolic stroke while assuring continuous cerebral perfusion.

Optionally, the whole process of cerebral protection may be repeated and conducted if desired once a 5-10 min period of cerebral reperfusion is reached. The procedure can be repeated at any time of surgery and on multiple occasions when the emboligenic intervention is anticipated. Upon completion of the main surgical procedure, the occluding catheter 37 can be completely removed or pulled back completely into the right subclavian artery 23R and/or the outer sheath 170 for later removal.

FIGS. 5 through 8 illustrate several exemplary embodiments of the occluding catheter 37 as being a 3-lumen, 2-balloon, 2-mesh; a 3-lumen, 2-balloon, 1-mesh and a 3-lumen, 2-balloon 1-mesh catheter 37. The occluding catheter 37 includes a shaft 104 that may have an outer circumference that is circular in cross-sectional shape. However, other cross-sectional shapes of the outer circumference are possible in accordance with other exemplary embodiments. Ports 46, 48 and 50 may have openings at their extreme proximal ends to allow for communication with their respective channels 68, 70, 72 and can have fittings configured to receive inflation syringes, pressure measurement and aspiration devices, guide wires or other components. Channels 68, 70, and 72 have circular cross-sectional shapes and are all the same diameter. However, in other arrangements the cross-sectional shapes may be different and their diameters can be variously sized such that they are not the same size as one another.

The channels 68, 70 and 72 are not in fluid communication with one another. The proximal and distal occluding balloons 38, 42 may be inflated separately from one another with the covering mesh expanded such that one is inflated before another one, or such that both inflate simultaneously with the respective expansion of the filtering mesh. Pressure of inflation supplied by a pressure supply 126 may be to a degree greater than the patient's systemic arterial pressure. The pressure inside the occluding balloons 38, 42 may exceed only minimally the patient's systemic and carotid arterial pressures with the goal to achieve partial or complete interruption of the antegrade carotid flow without undue trauma to these vessels (41, 26R, 26L) as reflected by the vascular ultrasound probes 190, 192, 194, 198 and/or 200.

Proximal occluding balloon inflation port 46 is in fluid communication with the proximal occluding balloon channel 68. The channel 68 may terminate at the proximal occluding balloon 38 and may not extend past the proximal occluding balloon 38 in the distal direction. One or more openings 58 may extend through the shaft 104 in order to place the channel 68 into fluid communication with the interior of the proximal occluding balloon 38. Fluid pressure supplied by a syringe or other source may be introduced through port 46, channel 68 and out of opening 58 in order to inflate the proximal occluding balloon 38 and its surrounding filtering mesh 130 to its inflated state.

The proximal occluding balloon 38 may be connected on its distal and proximal ends to the shaft 104 and inflation pressure will cause the proximal occluding balloon 38 and its outer mesh 130 to expand so as to have a circular cross-sectional shape. The proximal occluding balloon 38 may have other cross-sectional shapes in other exemplary embodiments such as oval, triangular, concave, convex, elliptical or a combination of thereof. Such balloon shapes, may provide the most appropriate shape for the outer mesh upon its expansion achieving the goal of the most congruent and coplanar approximation of the mesh with the inner surface of the vessel to be protected and or/its ostium at the level of the aortic arch 22, innominate artery 41, and ostia of the head vessels 41, 26 and 23.

The occluding balloon 38 and its surrounding filtering mesh 130 may be variously shaped and sized in accordance with different exemplary embodiments. The proximal occluding balloon 38 and the mesh 130 may be coaxial with the shaft 104. In accordance with various embodiments, the proximal occluding balloon 38 and mesh 130 may be coaxial with the channel 70, 72 or 68. In other embodiments the proximal occluding balloon 38 and mesh 130 are not coaxial with the shaft 104 or any of the channels 70, 72 or 68.

Figure 14A:
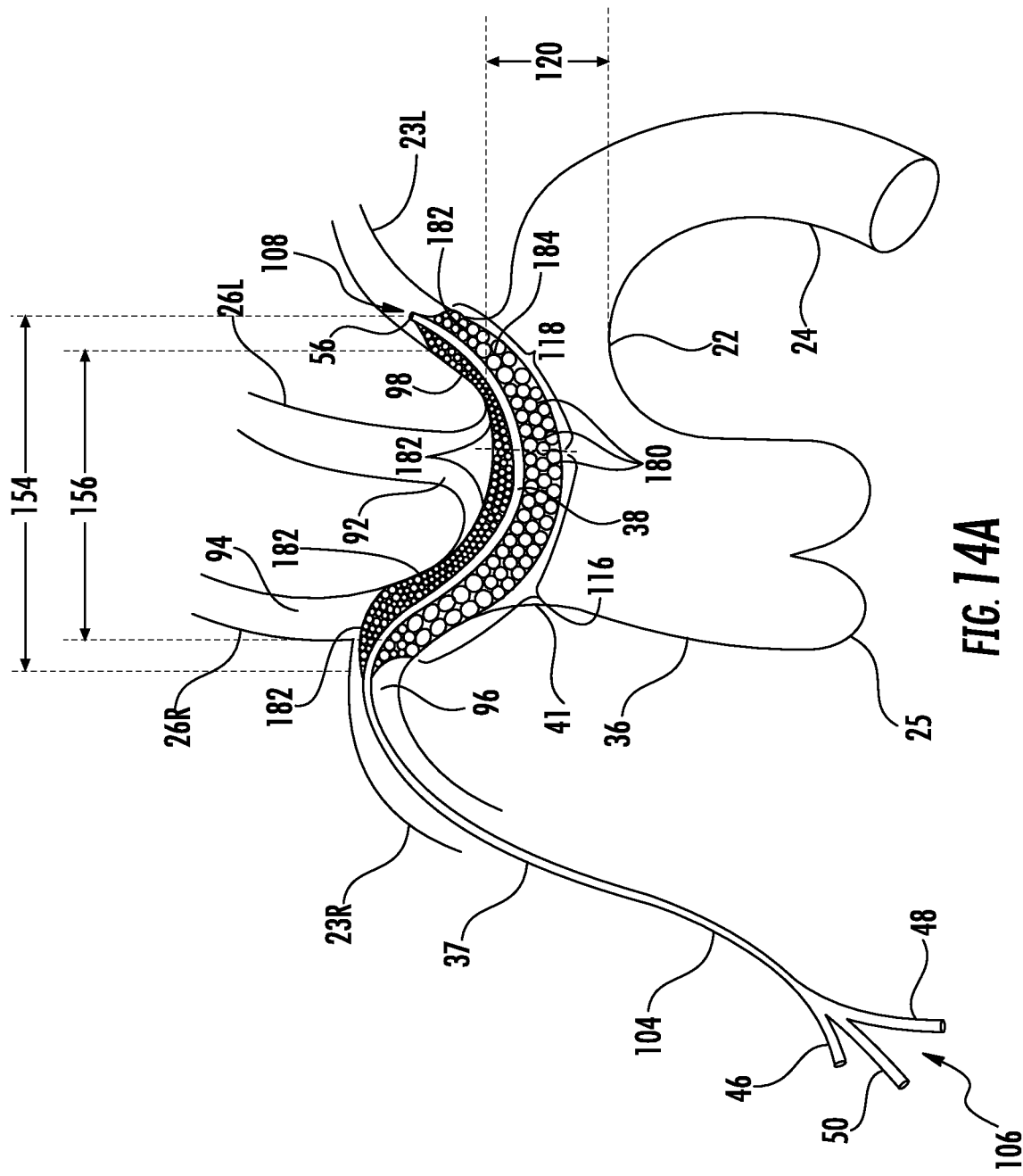
FIG. 14-A is a front view of the patient with the occluding catheter of FIGS. 13-B and 13-C in a semi-inflated state.
Figure 14B:
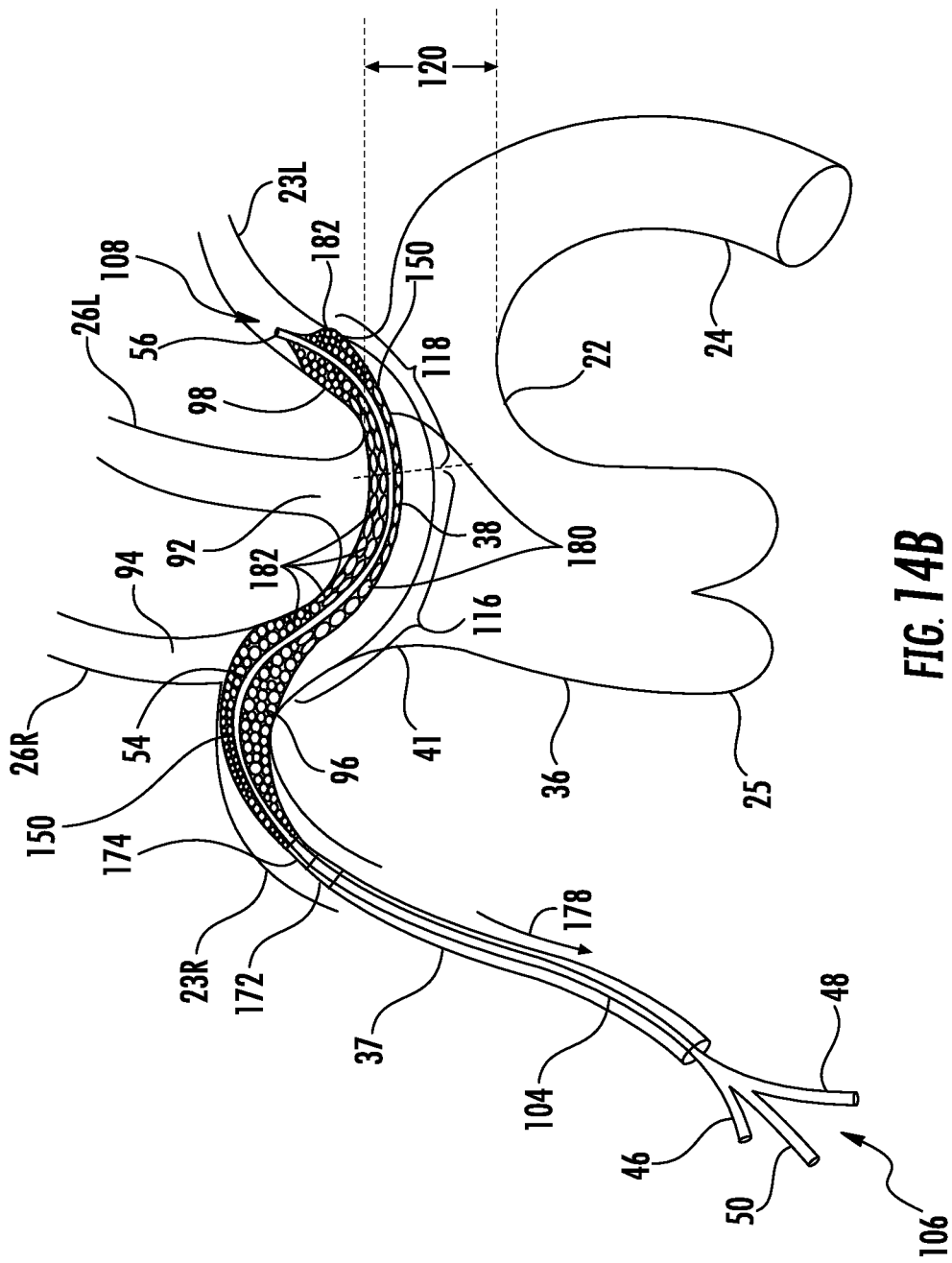
Figure 14C:
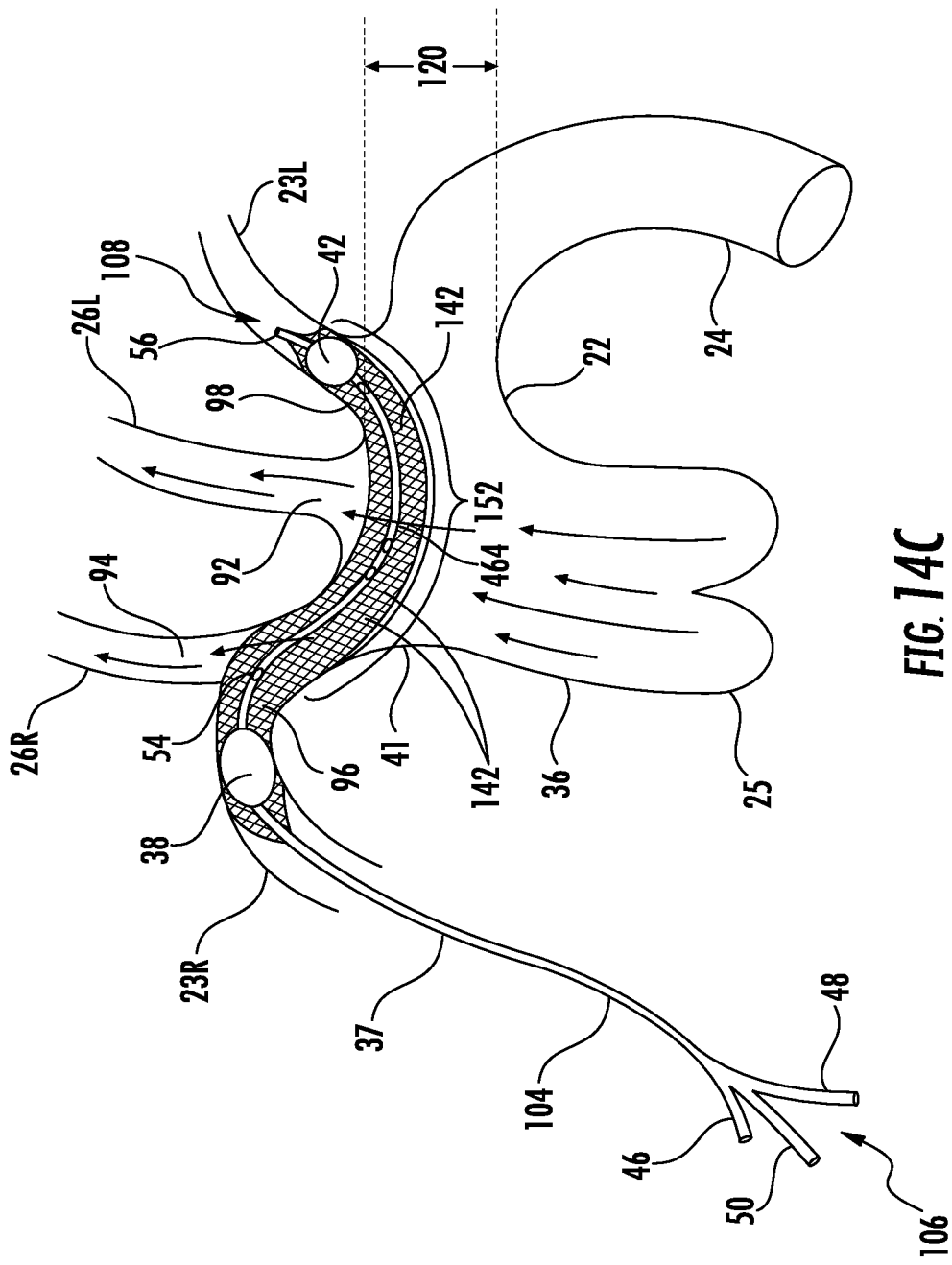

The shaft 104 continues in the distal direction past the proximal occluding balloon 38, but only channels 70 and 72 are present past the proximal occluding balloon 38. The distal occluding balloon 42 and its surrounding mesh 140 are located at the distal end 108 of the shaft such that a segment 44 of the shaft 104 is present between the occluding balloons 38, 42 to space them from one another. The outer mesh 130 may be separated from the outer mesh 140 by the segment 44 of the shaft 104, however in some embodiments it may extend to various degree towards each other with the distance between the distal end of mesh 130 and the proximal end of mesh 140 being shorter than the length of the segment 44 or completely absent. Moreover, in some embodiments both proximal balloon 38 and distal balloon 42 may be covered with a single common mesh 142 that extends from the proximal portion of the balloon 38 to the distal area of the balloon 42 bridging the gap between both balloons 38 and 42 (FIGS. 5-C and 5-D). This embodiment will achieve a goal of a more extensive filtering of blood with an improved trapping, deflection, deceleration and redirecting of potential emboli as the total area of the filtering mesh 142 may be significantly larger than the combined area of mesh 130 and 140. In some arrangements of this embodiment the one of the balloons may be positioned within the right subclavian artery, while the other balloon is positioned within the left subclavian artery, wherein neither of the balloons is in contact with the innominate (41), right carotid (23R) or left carotid (23L) arteries, yet when said balloons are expanded the bridging segment of the mesh will cover and protect the orifices of the arteries 41, 23R, and 23L without occluding flow to the right and left carotid arteries even when the balloons are inflated as the bridging mesh may be stretched and its shape will be stabilized between the inflated balloons 38 and 42 (FIG. 14-C). In some embodiments such mesh may be self-collapsible and may self-retract and collapse spontaneously around the catheter 37 for a facilitated removal with or without resorting to an outer sheath 170. Yet, in other embodiments the mesh may retain its shape after the balloons are deflated, as described above, and may be collapsed and retrieved by its recapturing using an outer sheath and/or by aspiration of its contents, its retraction, rotation, stretching and torqueing. Such processes may be facilitated using an optional locking mechanism 172-174 between the proximal mesh segment and its sliding ring and the outer sheath 170 or an optional guidewire. In the embodiments, where the occluding balloons 38, 42 are designed to occlude only the left and right subclavian arteries, these balloons may have a smaller length and diameter (optimally, between 1.5 and 3.5 cm), specifically designed to occlude both right and left subclavian arteries without touching or compromising the lumen of the innominate, right carotid and left carotid arteries. Such an arrangement will achieve the goal of positioning the filtering mesh upstream from both carotid arteries with the filtering of blood that is to enter the carotid arteries, yet without inducing a potential trauma to these vessels by the direct contact between the filtering hardware, the catheter and the balloons and the inner wall of the carotid arteries. The disclosed pore arrangements in this setting will provide an option of both filtering and deflection of the incoming emboli, features that may be varied and adjusted depending on the variable and adjustable pore size and configuration as a result of affecting the geometry of the mesh.

In addition, in other embodiments both balloons 38 and 42 may extend towards each other and/or outward due to their structural propensity for further longitudinal and/or radial expansion in relation to the central axis of the catheter 37 and or shaft 104 once a certain level of the intraluminal pressure inside the balloon is reached. This structural feature is designed to provide for a more extensive area of coverage of the inflow pathways toward the innominate, carotid and, if needed, subclavian arteries to assure a more complete anti-embolic protection of the brain. The surrounding mesh in these embodiments is designed to preserve its expanded configuration corresponding to the shape achieved by the underlying balloon during its expansion even after the underlying balloon is deflated, thus preserving an adequate flow to the brain, while providing a process of filtering of the blood flowing therethrough, once the balloon is deflated.

The distal occluding balloon channel 72 extends from the distal occluding balloon inflation port 48 and terminates at one or more openings 60 of shaft 104. The distal occluding balloon 42 surrounded by its mesh cover 140 is attached at its proximal and distal ends to the shaft 104 and is inflated via pressure supplied through port 48, channel 72 and out of opening 60. A single opening 60 may be present, or a plurality of openings 60 may be present through which pressure can be supplied to inflate the distal occluding balloon 42. The distal occluding balloon 42 and its filtering mesh 140 may have a circular cross-sectional shape, although other cross-sectional shapes are possible in other exemplary embodiments as discussed regarding balloon 38.

The longitudinal length and the volume of the distal occluding balloon 42 and its mesh 140 may be less than that of the proximal occluding balloon 38 and mesh 130. However, their longitudinal lengths and volumes may be the same in other arrangements, or in yet further designs the longitudinal length and volume of the proximal occluding balloon 38 and mesh 130 are less than the longitudinal length and volume of the distal occluding balloon 42 and its mesh 140. The distal occluding balloon 42 and mesh 140 may be coaxial with the shaft 104 in certain arrangements, and in other arrangements may be coaxial with channels 70 or 72. In yet other exemplary embodiments, the distal occluding balloon 42 and mesh 140 are not coaxial with shaft 104 and are not coaxial with channels 70 or 72.

The diameter 112 of the distal occluding balloon 42 approximates the diameter of mesh 140 or the distal segment of mesh 142 and is less than the diameter 110 of the proximal occluding balloon 38 and its mesh 130. In other exemplary embodiments diameter 110 may be less than diameter 112, or the diameters 110 and 112 may be equal to one another. The diameters 110 and 112 may be the same along the entire longitudinal lengths of the occluding balloons 38, 42 and their mesh 130, 140, 142 or the diameters 110 and 112 may be different at different points along the longitudinal lengths of the occluding balloons 110 and 112 and their mesh 130, 140, 142. The diameters 110 and 112 and cross-sectional shapes of the proximal and distal occluding balloons 38, 42 and their possible mesh covers 130, 140 and 142 are described when outside of the body of the patient.

The distal occluding balloon channel 72 may terminate proximal to the distal end of the distal occluding balloon 42. Only the end pressure measurement channel 70 may extend distally beyond the distal occluding balloon 42. The distal tip of the shaft 104 terminates at a distal tip opening 56 at its terminal distal end. The shaft 104 extends beyond the distal occluding balloon 42, but in other arrangements, the distal occluding balloon 42 in the inflated state may extend beyond the terminal distal end of the shaft 104 in the distal direction. The end pressure measurement port 50 can be in communication with the end pressure measurement channel 70 that in turn terminates at the distal tip opening 56, represented by the single opening or a plurality of openings 56. The channel 70 in other arrangements may be in fluid communication with one or both channels 68 and 72. Likewise, in yet other exemplary embodiments, channel 70 is not in fluid communication with channels 68 and 72, but channels 68 and 72 are in fluid communication with one another so that the proximal and distal occluding balloons 38, 42 inflate and deflate with one another. Distal tip opening 56 or a plurality of such openings 56 may be used for pressure measurements distal to the distal occluding balloon 42, yet proximal to the distal end of the mesh 140, 142. This configuration is designed in order to use the openings 56 and their corresponding pressure measurement channel for active aspiration of the emboli trapped in the distal segment of the mesh 140, 142 during the procedure. To facilitate such aspiration an outer sheath 170 may be provided that may be advanced over the catheter shaft 104 in order to cover and retrieve the mesh 130, 140 and/or 142. The process of the mesh retrieval using an outer sheath 170 is depicted in FIGS. 5-G through 5-I and also in FIG. 14-B, The outer sheath 170 is advanced over the catheter 37 until it encounters the deflated balloon 38 and the expanded mesh 130 (FIG. 5-G). Further advancement of the outer sheath 170 with a simultaneous aspiration through the proximal pressure port 52 and channel 74 connected to the mesh 130 via an opening 54 will facilitate a complete recapturing of the balloon catheter 37 with its expanded mesh (FIGS. 5-H and 5-I) and it may be pulled back into the subclavian artery 26 or removed completely.

As depicted in FIGS. 7, 8, 9 and 10 the different areas of the filtering mesh may have pores of a different size and configuration. Pores 180 are the largest pores located at the area 152 of the mesh. The area 152 of the mesh is named a "cranial" or craniad area as it is designed to face the orifices of the head vessels 41, 26, 23 of the aortic arch 22. Pores 182 may be the smallest pores of the mesh, located in the area 154 of the mesh. The area 154 is located on the opposite side of the mesh in relation to area 152 and is named a "cardiac" or caudad area 154, as it faces the heart 21, aortic valve 25, ascending aorta 36 and the aortic arch 22 i.e. the parts of the circulatory system that generate and eject emboli 28. In some embodiments there may be an intermediate area 158, carrying the pores 184 of intermediate size. Area 158 is the one that does not face or only partially faces the structures that are faced by the areas 152 and 154.

FIGS. 9 and 10 illustrate an alternative exemplary embodiment of the occluding catheter 37 that is a four-channel version of the occluding catheter 37. Intermediate pressure measurement channel 74 extends from an intermediate pressure measurement port 52 to an opening 54 or multiple openings 54 of the shaft 104. Opening 54 or a plurality of openings 54 is/are located proximal to the proximal occluding balloon 38, yet inside the area, covered by the mesh 130 and/or mesh 142. The intermediate pressure measurement channel 74 is not in fluid communication with the other channels 68, 70 and 72 of the occluding catheter 37. The intermediate pressure measurement channel 74 may terminate proximal to the proximal occluding balloon 38, but inside the area of the mesh 130 and 142. The other components of the occluding catheter 37 are the same as described above and their description need not be repeated. A manometer may be connected to the intermediate pressure measurement port 52 to allow recording of blood pressure from the opening 54. If the proximal occluding balloon 38 is located within the innominate artery 41, the opening 54 may be used to detect the dampening of the arterial pressure in the innominate 41 and right carotid artery 26R, after proximal occluding balloon 38 inflation, confirming adequacy of the flow interruption to the right carotid 26R and subclavian arteries 23R. In addition the openings 54 may be used for aspiration of embolic particles from the mesh 130, 142 while the balloon 38 is deflated.

Figure 5E:
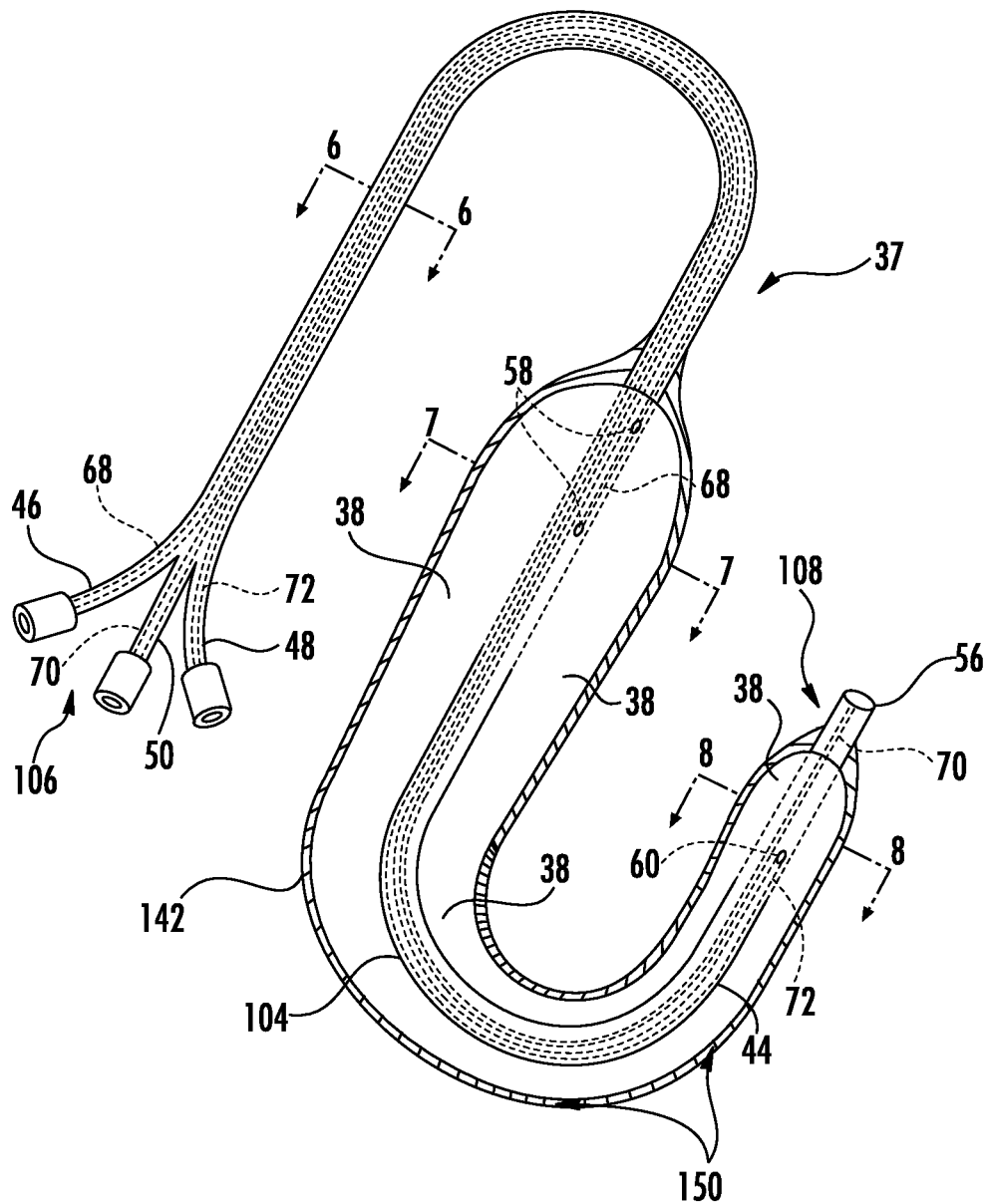
Figure 5F:
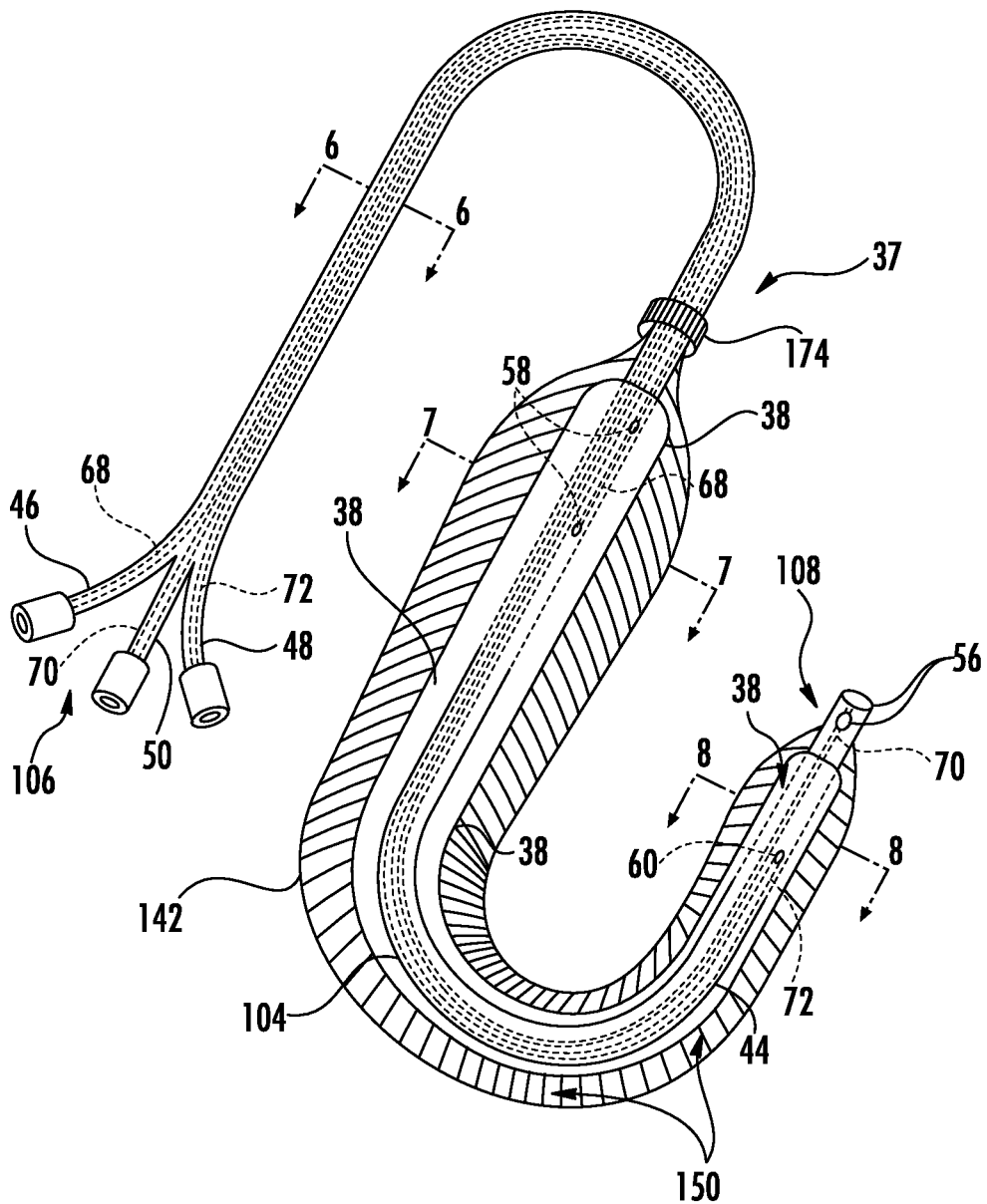
Figure 5G:
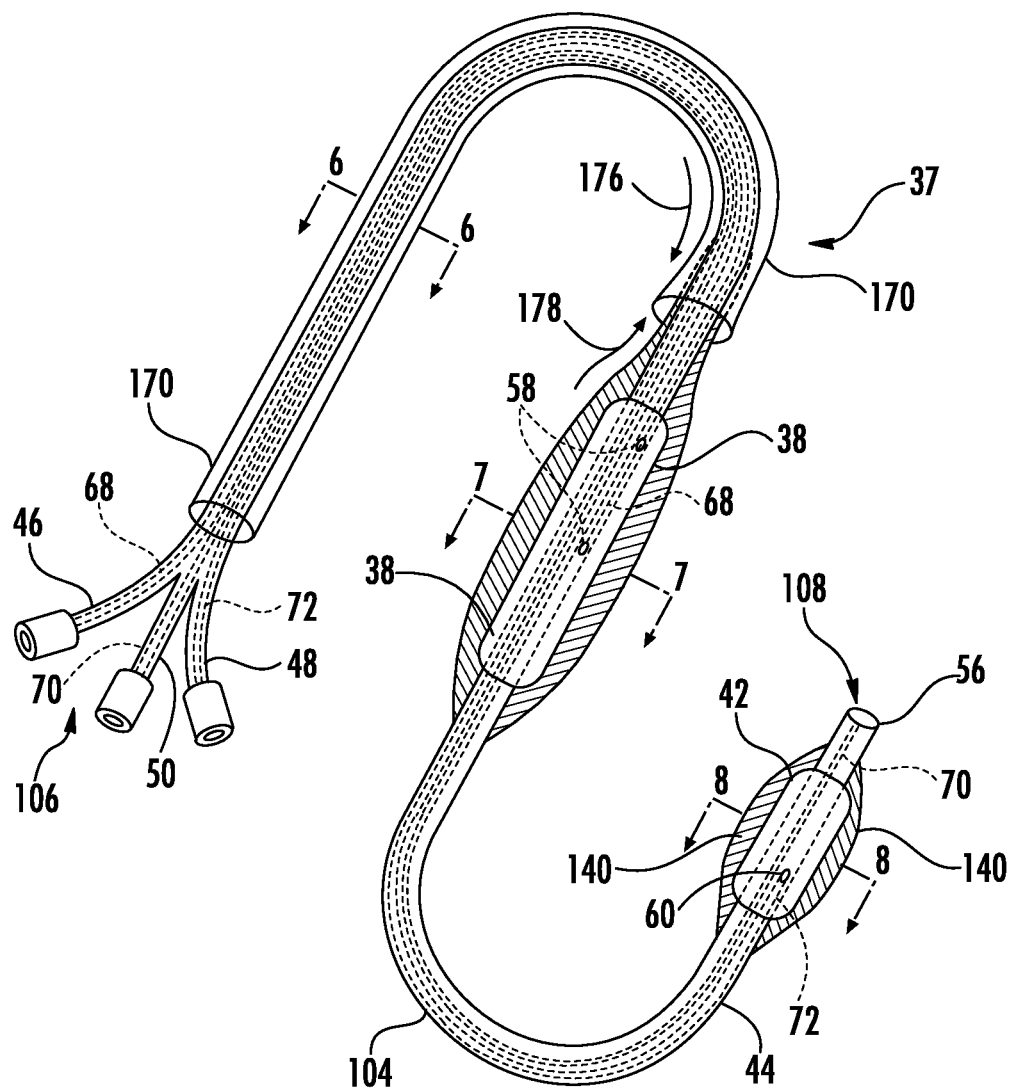
Figure 5H:
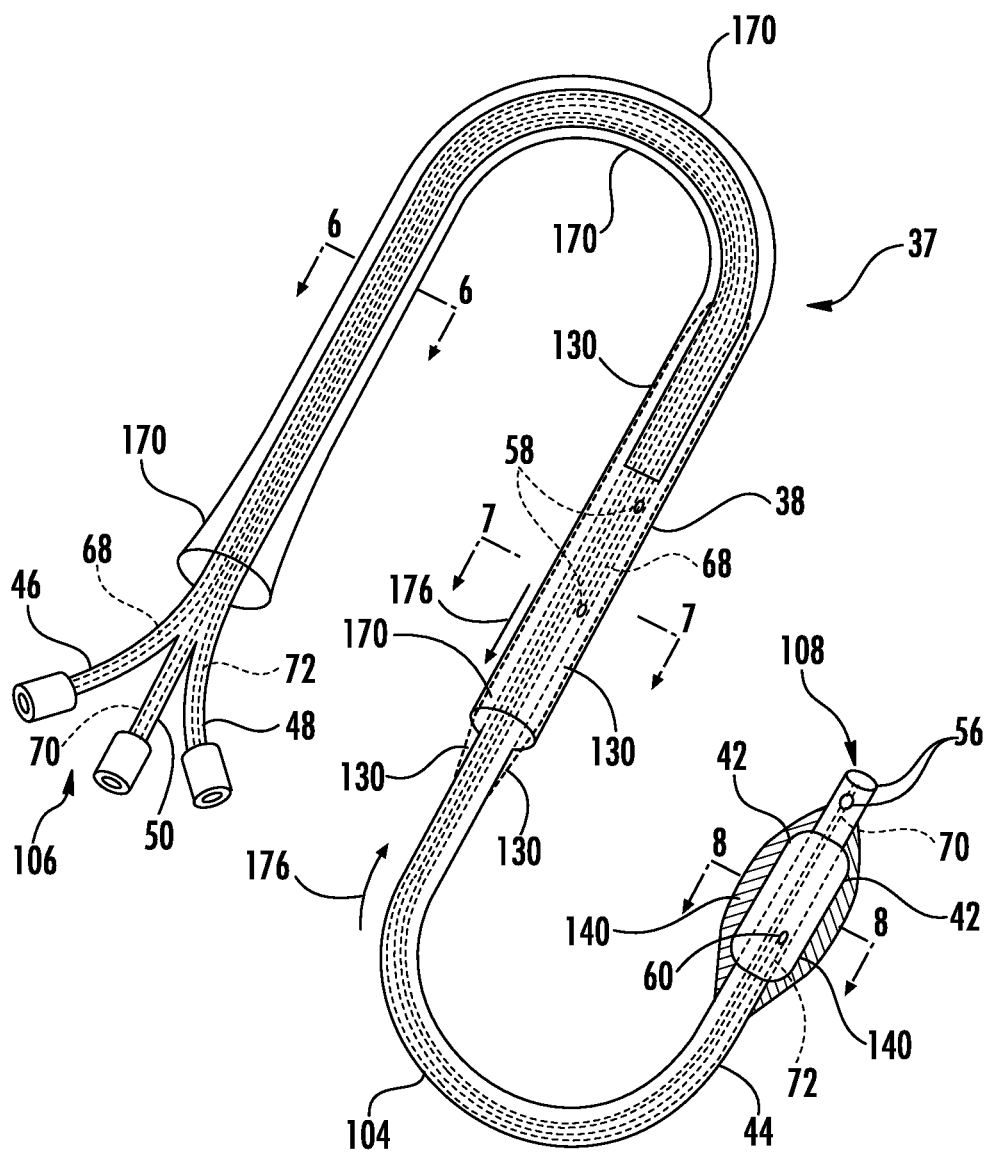
Figure 5I:
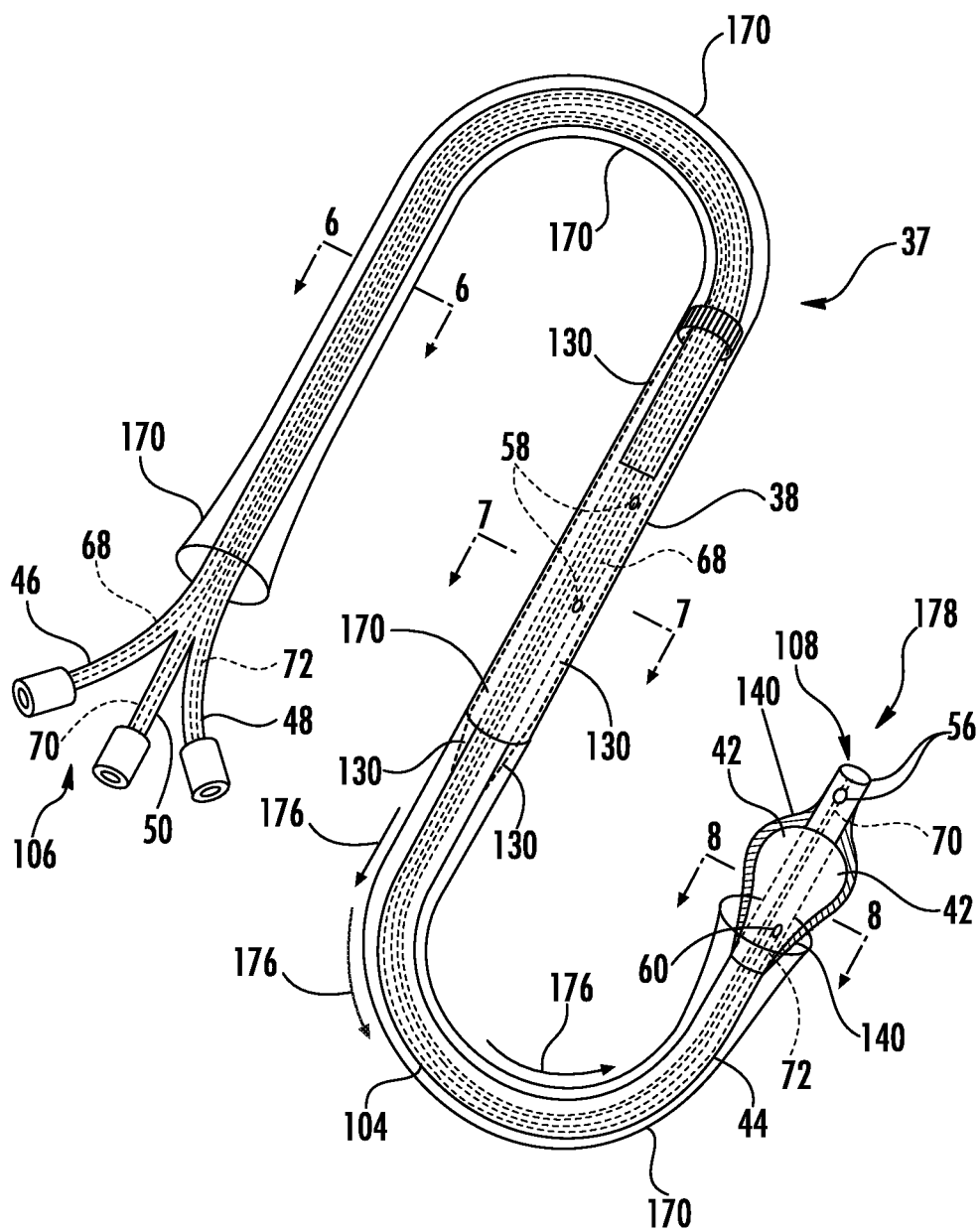
Figure 6:
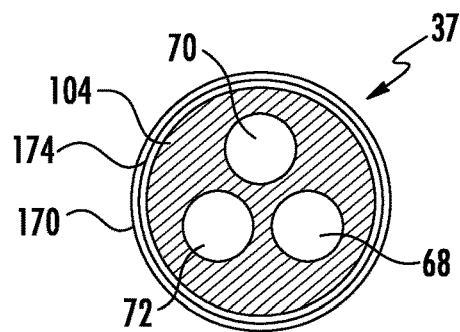
FIG. 6 is a cross-sectional view taken along line 6-6 of FIG. 5.
Figure 7:
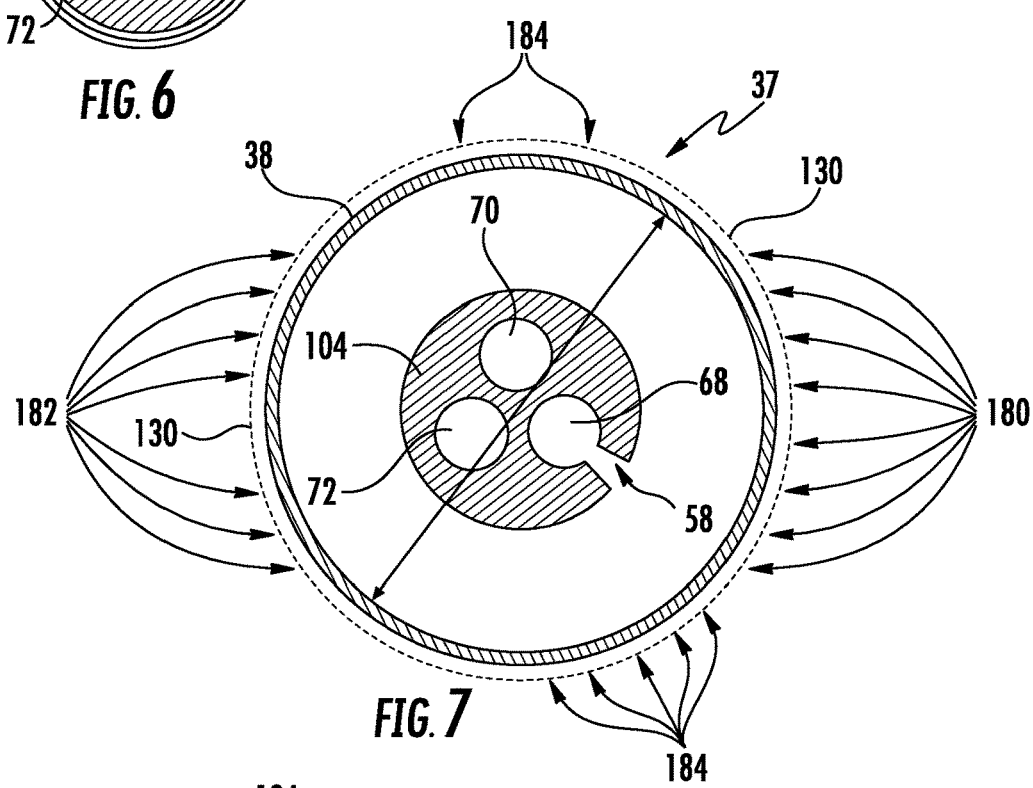
FIG. 7 is a cross-sectional view taken along line 7-7 of FIG. 5.
Figure 8:
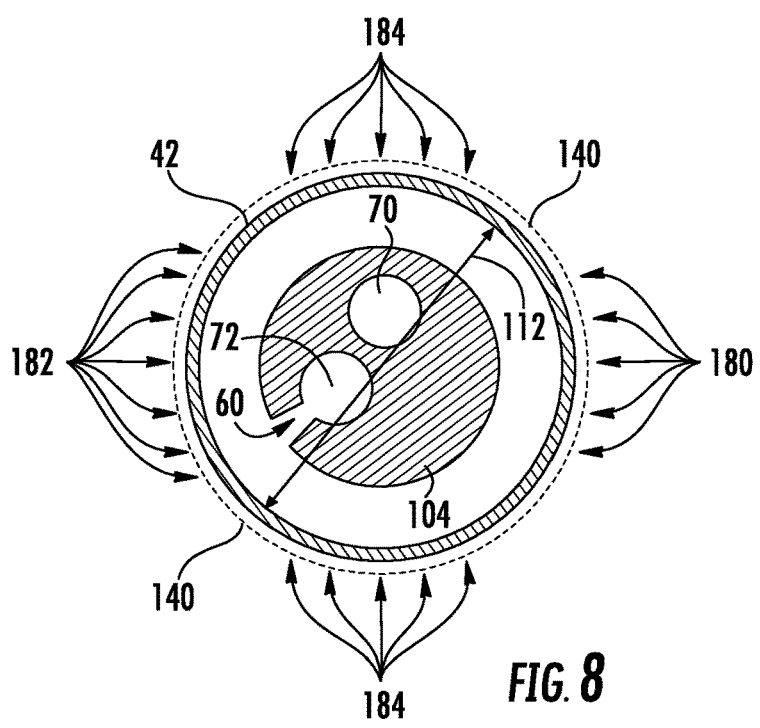
FIG. 8 is a cross-sectional view taken along line 8-8 of FIG. 5.
Figure 9A:
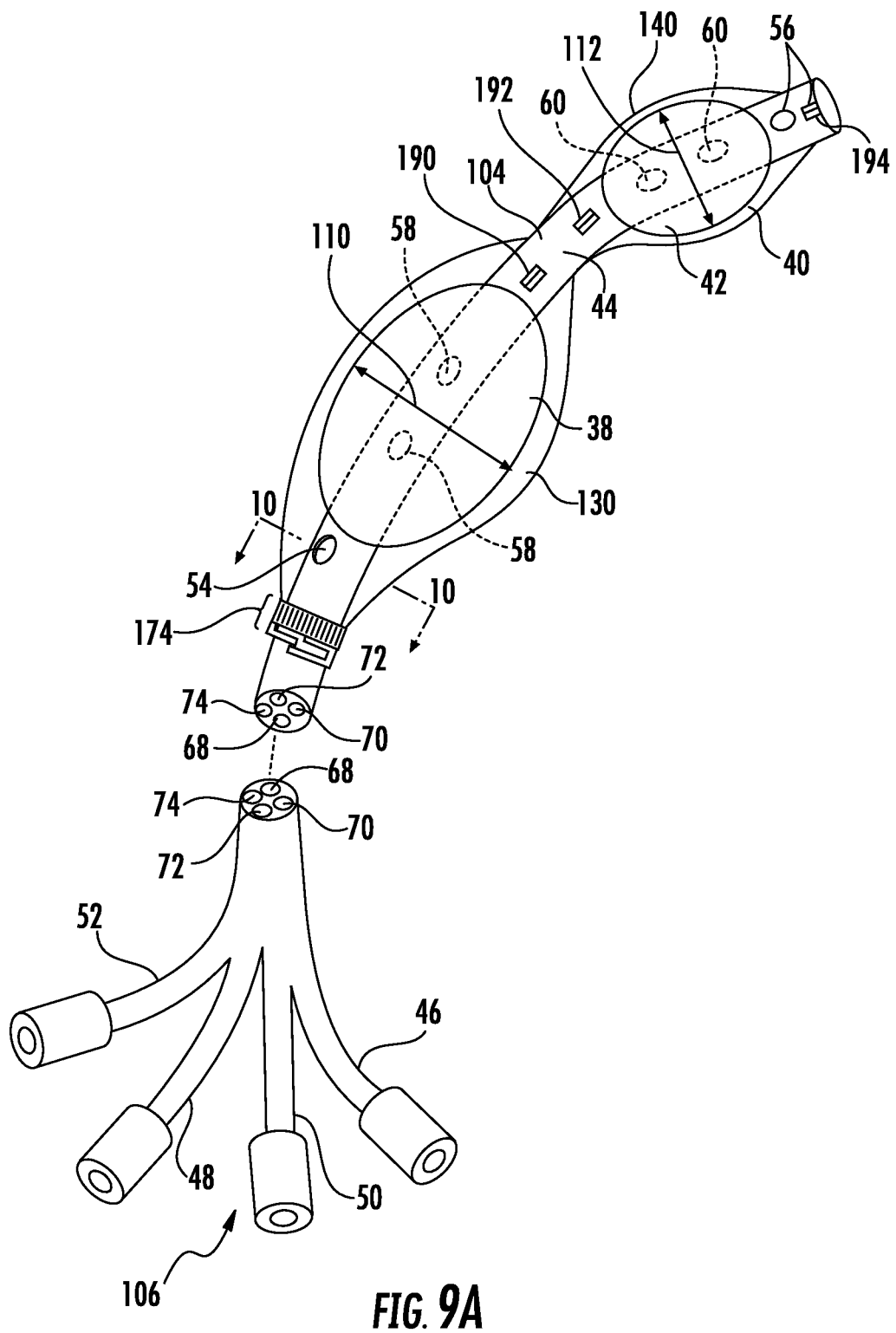
FIG. 9-A is a perspective view of the occluding catheter of FIG. 2 in an inflated state and with a section cut away to view interior portions.
FIG. 9D is a perspective view of the occluding catheter of FIG. 5-C in an inflated state showing different sizes of the mesh pores in relation to the opposite sides of the occluding catheter FIG. 10-A is a cross-sectional view taken along line 10-10 of FIG. 2.
Figure 9B:
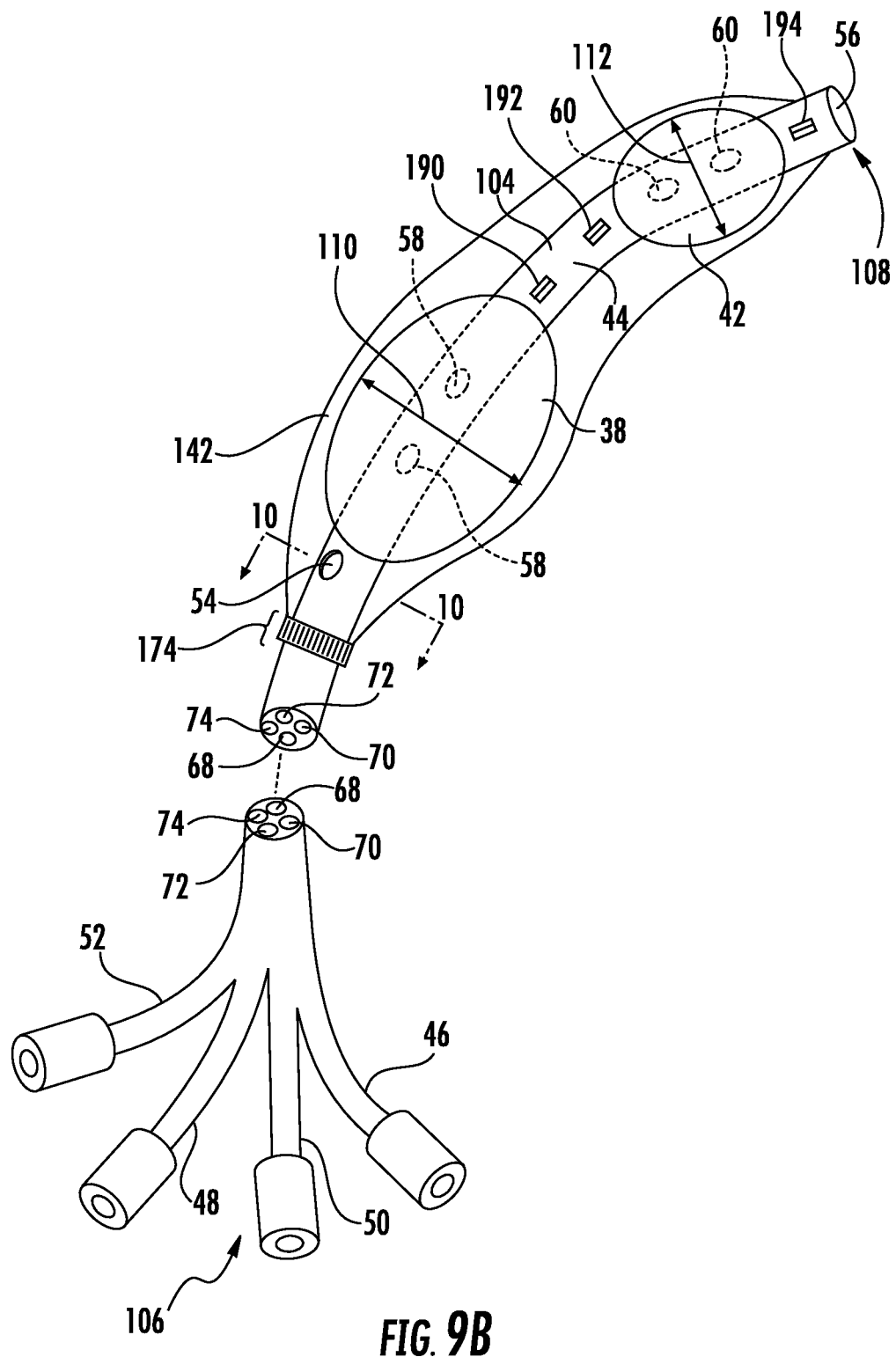
Figure 9C:
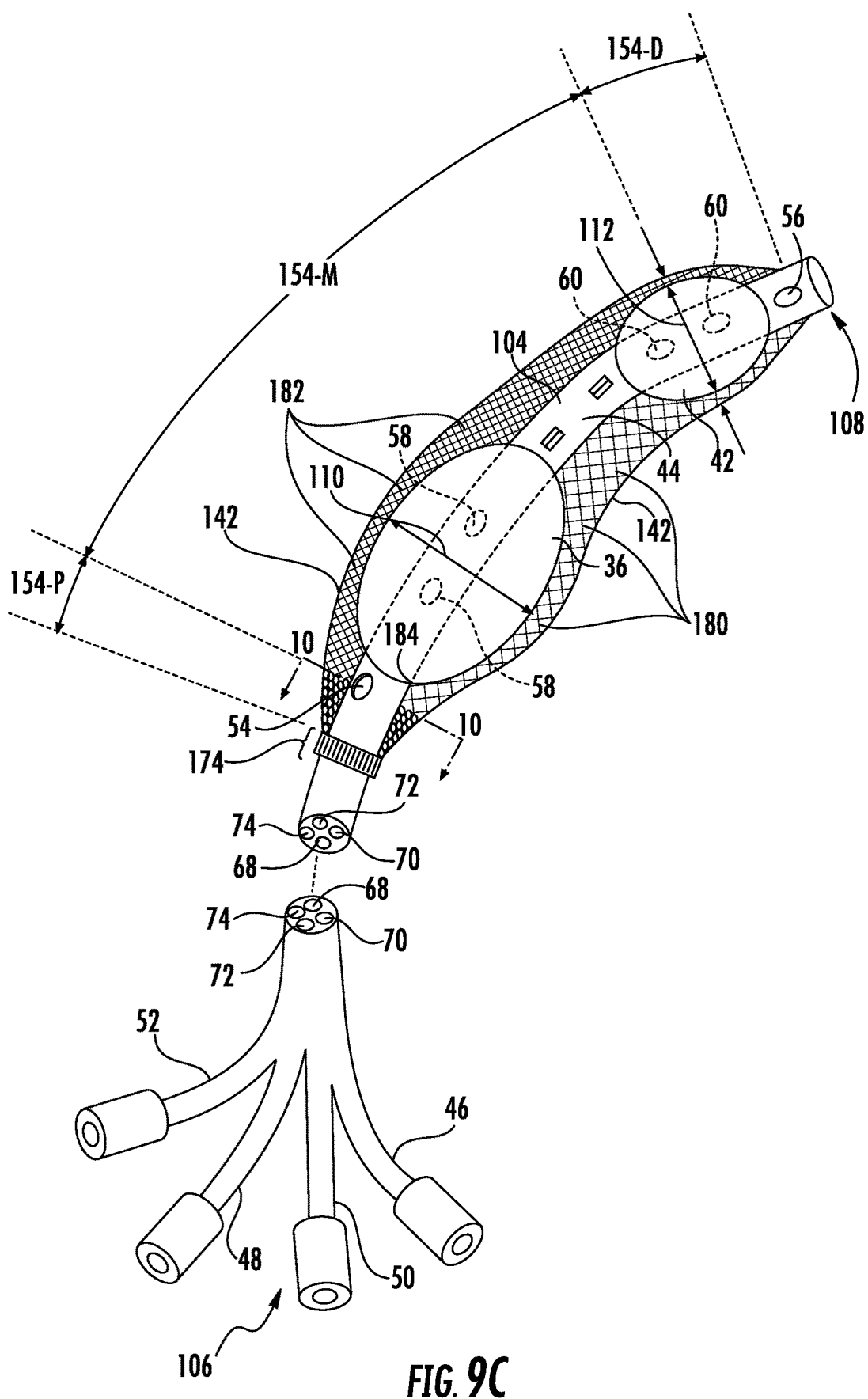
Figure 9D:
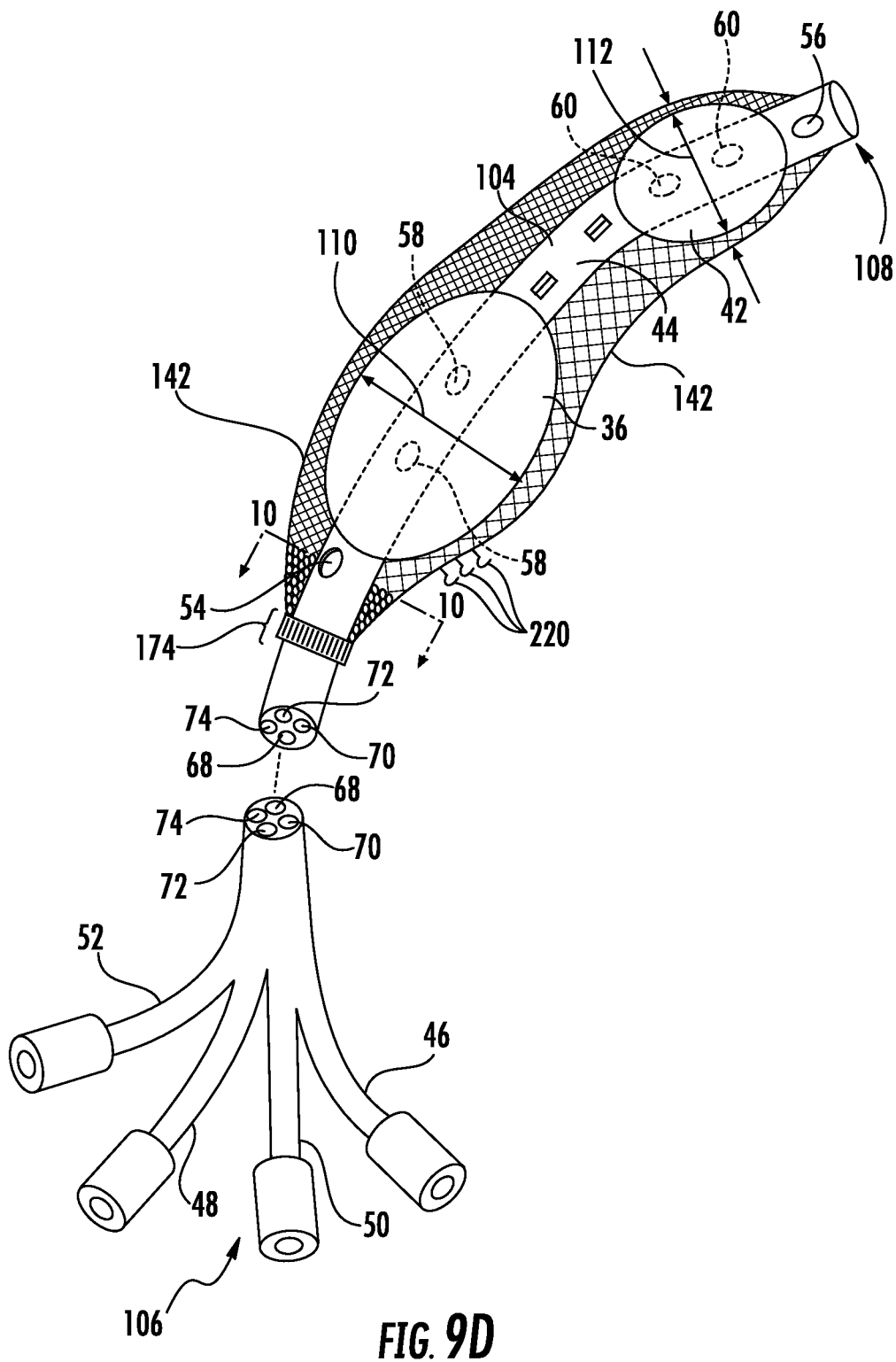
Figure 10A:
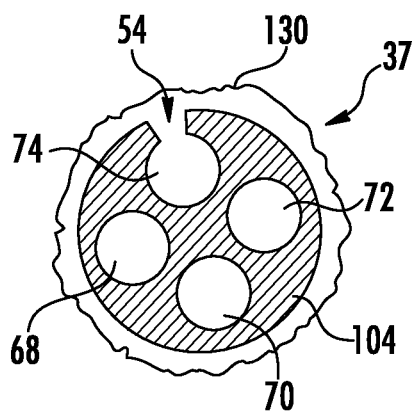
FIG. 10-B is a cross-sectional view taken along line 10-10 of FIG. 5-C.
Figure 10B:
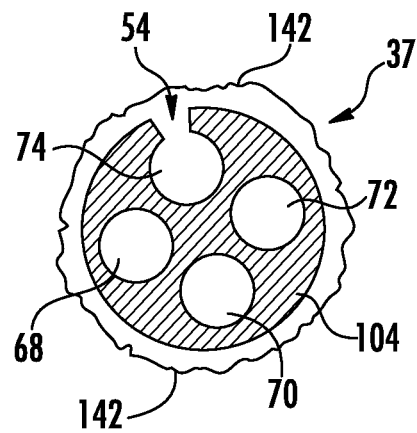
Figure 10C:
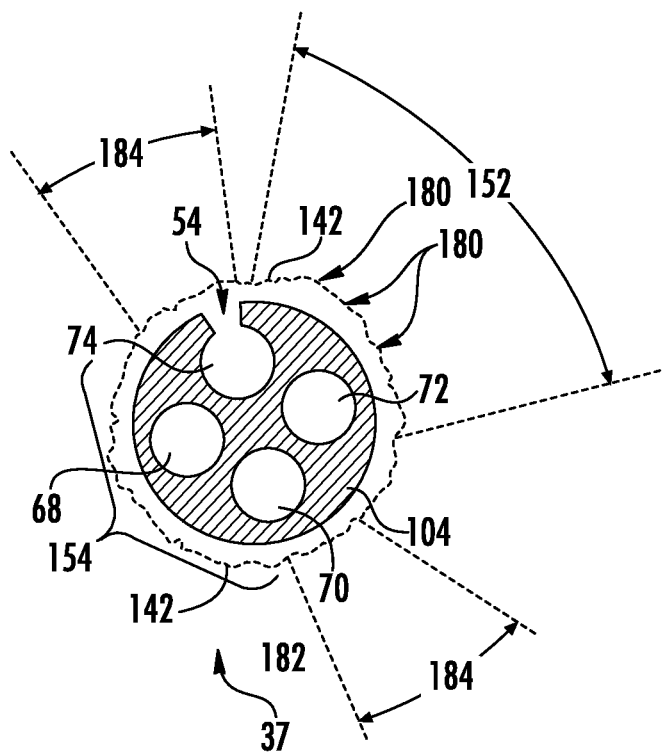
Figure 10D:
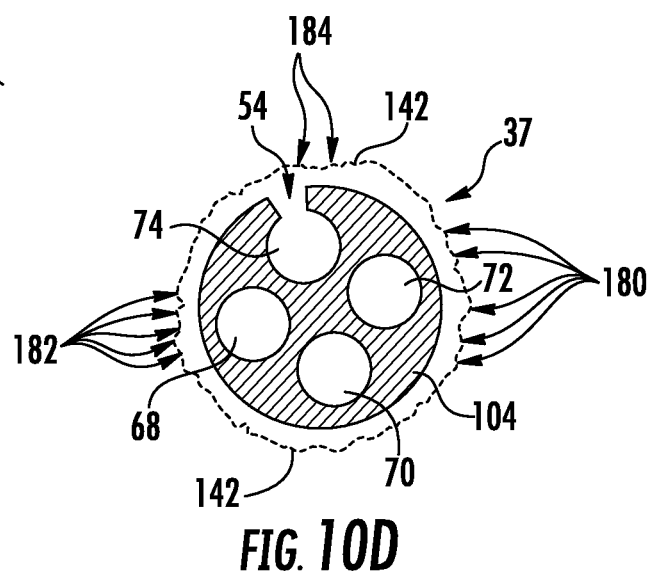
Figure 11A:
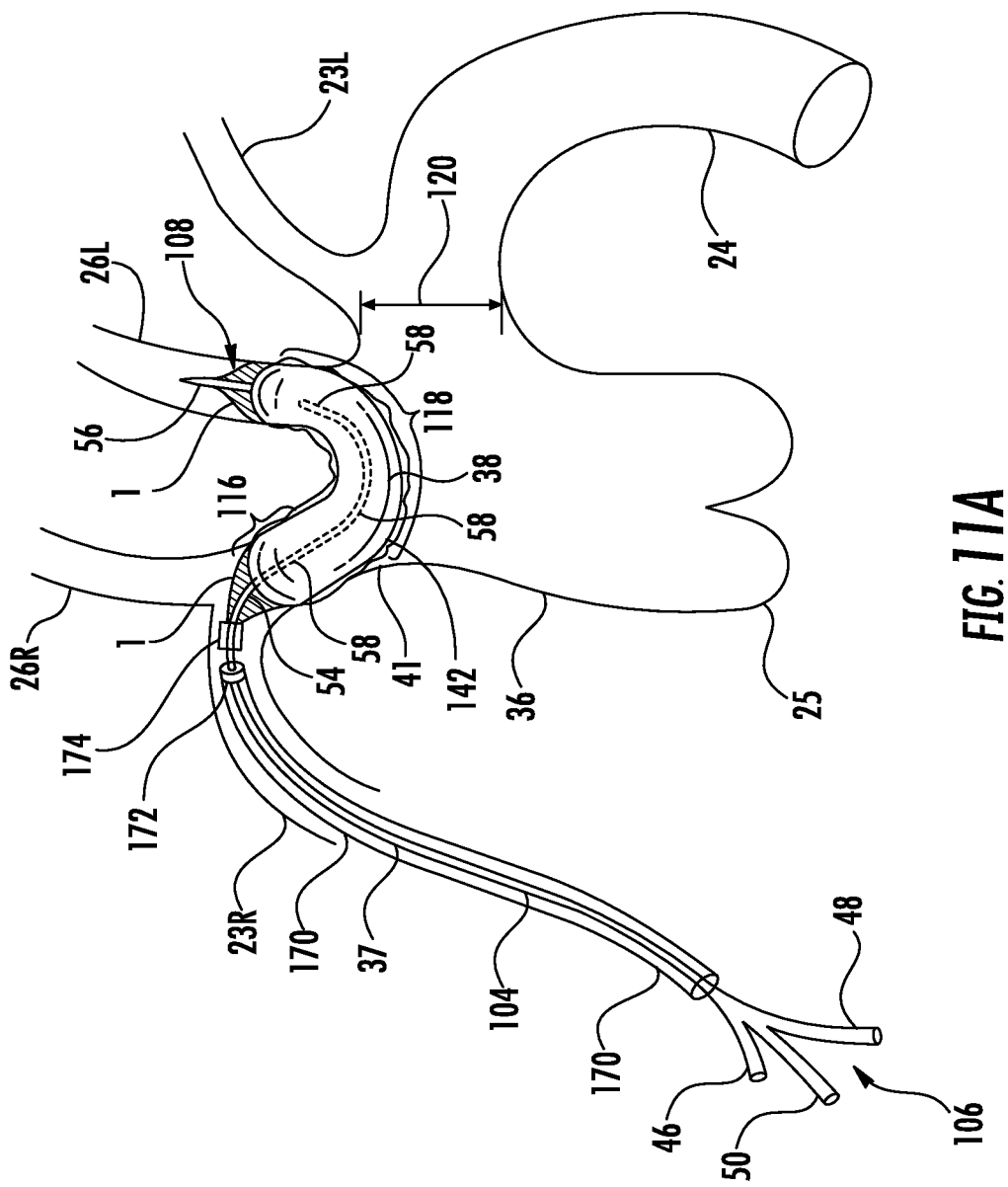
FIG. 11-A is a front view of the patient with an inflated occluding catheter with the filtering mesh expanded in accordance with another exemplary embodiment.
Figure 11B:
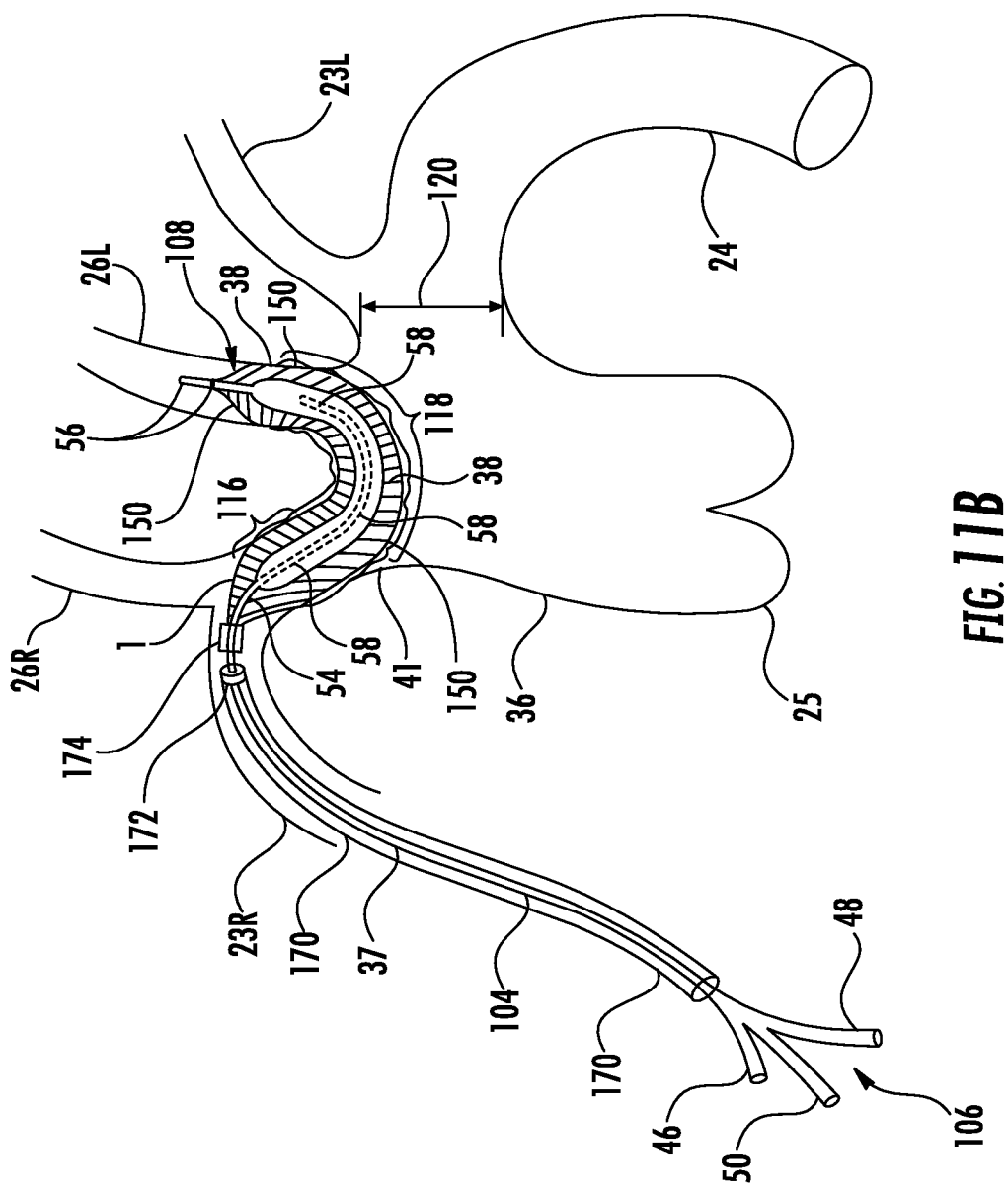

In another embodiment bilateral carotid 23R and 23L flow interruption can be achieved by creating a single occluding balloon 38. FIG. 11 shows one exemplary embodiment with a single occluding balloon 38, covered by a single filtering mesh 150 as depicted in FIGS. 5E, 5F, 11-A, 11-B, 13, 14 and 15. The occluding balloon 38 and its mesh 150 may extend throughout the whole distance between the bifurcation of the innominate artery 41 and the main trunk of the left carotid artery 26L. The single occluding balloon 38 may be longer than both the proximal occluding balloon 38 and distal occluding balloon 42 combined (as described in previous exemplary embodiments), with its length being in the range between 6 and 24 cm. Similarly, mesh 150, surrounding the balloon 38 and expandable according to the each particular shape and maximal dimensions of a said balloon may match or slightly exceed the length of 6-24 cm.

When described as a single occluding balloon 38 surrounded by the single mesh 150, it is to be understood that complete blockage or filtering of flow to the right and left carotid arteries 26R and 26L may be achieved by the single occluding balloon 38-mesh 150 arrangement without the use of any other occluding balloon-mesh arrangements, or without even the presence of another occluding balloon-mesh arrangements carried by the occluding catheter 37.

The occluding balloon 38-mesh 150 arrangement may be constructed so that it has a proximal portion 116, designated to occlude and/or filter the blood flow entering the innominate artery 41, which is larger than a distal portion 118 of the occluding balloon 38-mesh 150 arrangement to assure adequate occlusion of the innominate artery 41. Generally, the innominate artery 41 is at least twice as large as the left carotid artery 26L or the left subclavian artery 23. The single occluding balloon 38-mesh 150 arrangement may thus have a proximal portion 118 with a larger diameter than the diameter of the distal portion 118 of the single occluding balloon 38. These differences in diameters/sizes would be present when the single occluding balloon 38-mesh 150 is inflated without being inside of the patient. The other option involves the single occluding balloon 38 being a large volume, highly compliant occluding balloon supplied with an outer mesh 150 of an appropriate compliance that does not have any disparity in the diameters/size of the proximal portion 116 and distal portion 118 when inflated and not inside of the patient, plus—may elongate and become larger once a certain amount of intra-balloon pressure is reached. Once inflated inside of the patient and presented with arteries of different sizes, the proximal and distal portions 116, 118 of the highly compliant occluding balloon 38-mesh 150 configuration expand as necessary for complete approximation with the walls of arteries 41 and 26L at minimal pressures and without significant compression of the arterial walls 41, 26L. The single occluding balloon 38-mesh 150 configuration thus expands as necessary to fill the space required for occlusion and subsequent filtering, capturing, deflection and elimination of the embolic particles as it is composed of very flexible members in construction. After the balloon 38 is deflated, the mesh 150 remains expanded while approximating an intravascular shape, configuration and dimensions of the previously inflated balloon 38 with a resultant coverage of the innominate, carotid and, if needed, subclavian arteries 41, 26, 23. This feature is achieved in some embodiments due to the mesh being constructed using of a material carrying some recoil, shape memory, memory recoil and expansion features providing for the mesh to open and maintain its shape upon deflation of the balloon or when actuated and allowing for the mesh 150 to stay expanded in spite of deflation of the balloon 38. In some embodiments these features may be used to achieve full mesh expansion in spite of only minimal balloon inflation, or without using and inflating balloon at all. In this case the mesh can be expanded efficiently by inserting it inside an outer sheath 170 with the deploying mechanism comprising a guidewire attached to the mesh, such attachment being ether releasable or permanent.

Figure 13A:
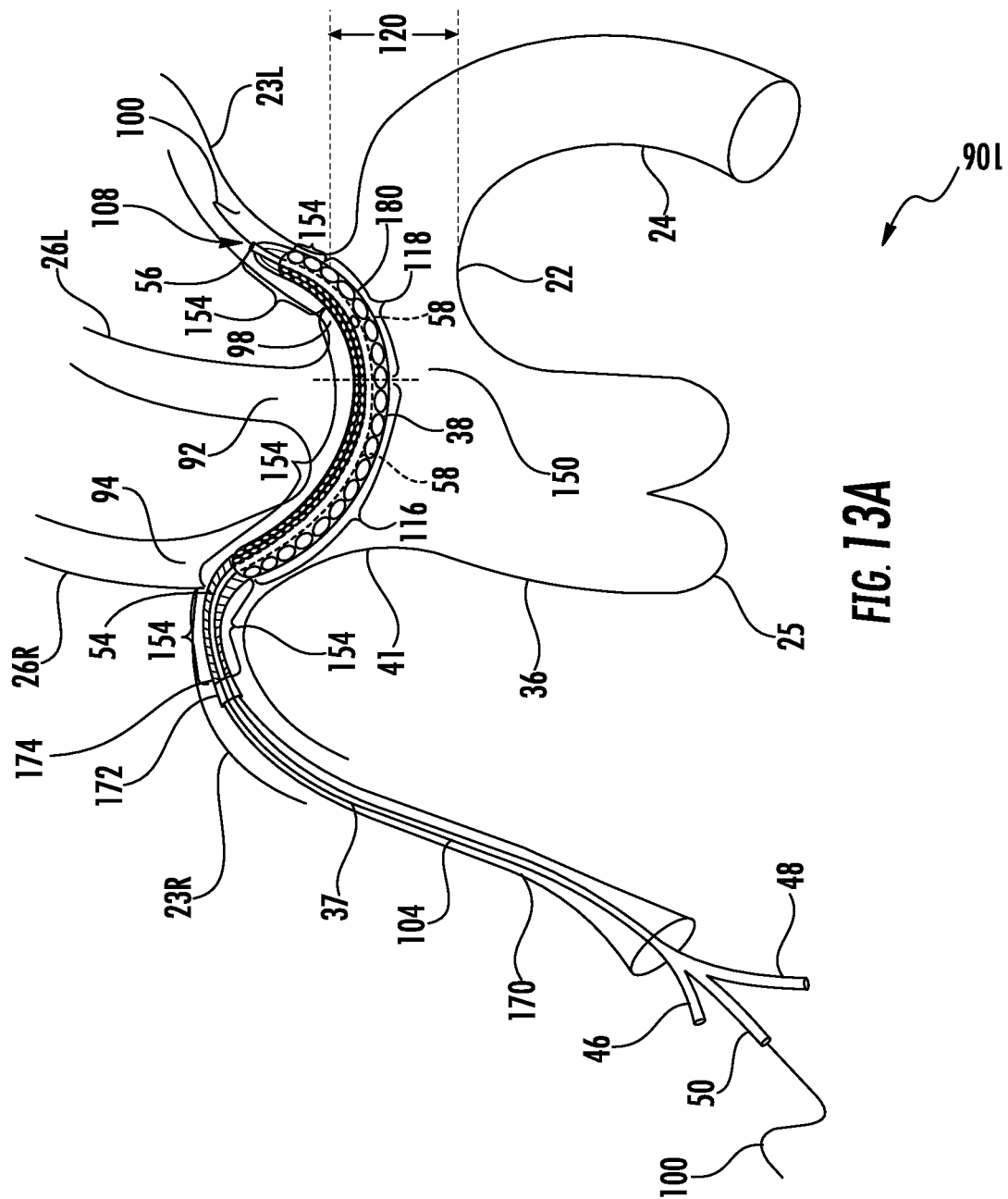
FIG. 13-A is a front view of the patient with a deflated occluding catheter introduced through a right subclavian artery in accordance with another exemplary embodiment.
Figure 13B:
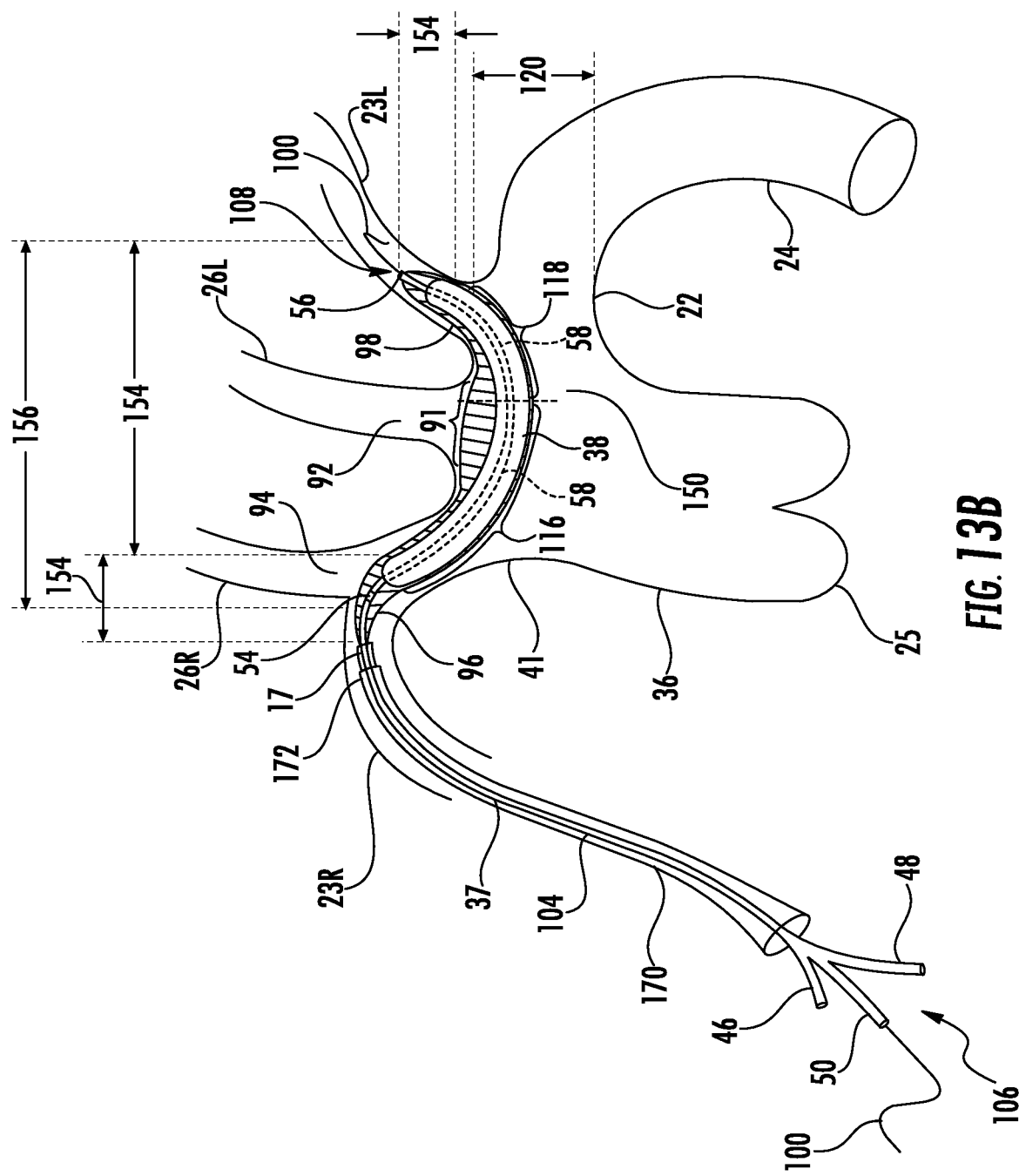
Figure 13C:
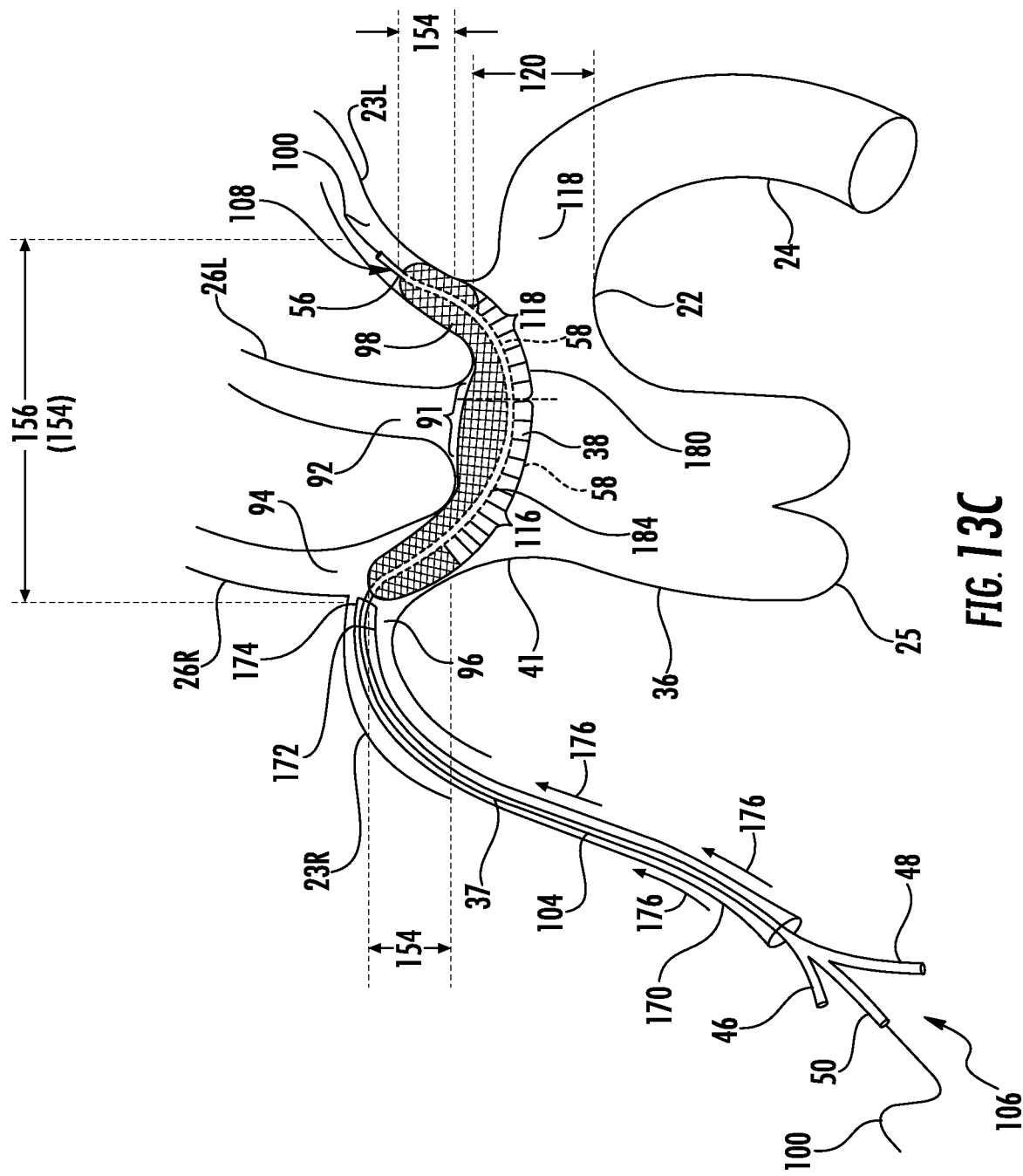
Figure 15:
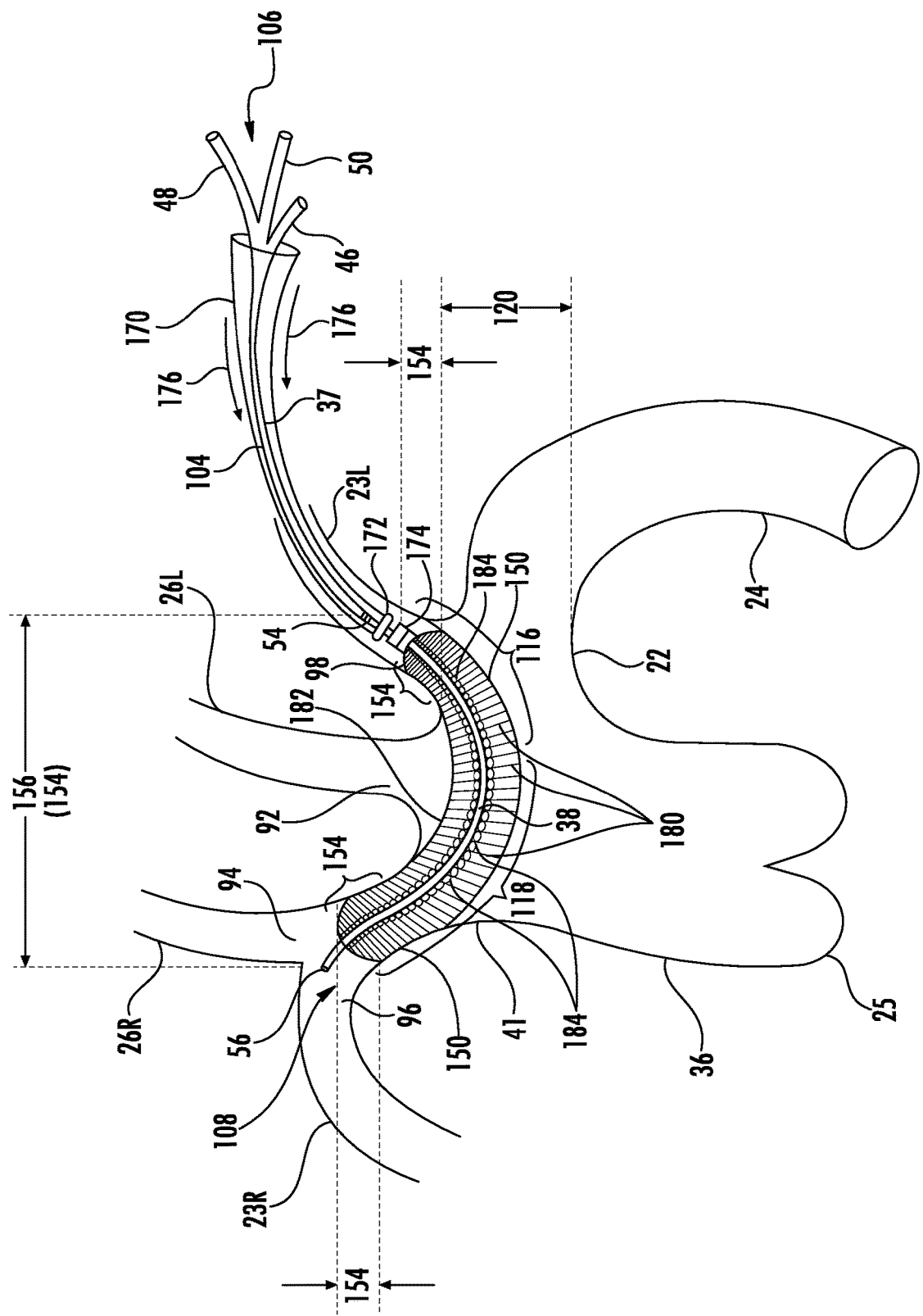
FIG. 15 is a front view of the patient with the occluding catheter of FIGS. 13-A and 13-B in an inflated state and with a filtering mesh expanded but introduced instead through a left subclavian artery in accordance with a still further exemplary embodiment.

As described previously, the proximal occluding balloon 38 may have other cross-sectional shapes in other exemplary embodiments such as oval, triangular, concave, convex, elliptical or a combination of thereof. Such balloon shapes, especially in a single balloon-single mesh arrangement as depicted in FIGS. 13, 14, and 15, may provide the most appropriate shape for the outer mesh upon its expansion achieving the goal of the most congruent and coplanar approximation of the mesh with the inner surface of the aortic arch 22, especially at the aortic arch area 156 comprising the ostia of the head vessels 41, 26 and 23. Moreover, as shown in FIGS. 13-B and C, there may be a protrusion or herniation in the shape of the filtering mesh 150 such as protrusion 91, protruding into the orifice of the left carotid artery 92. Such protrusions that may be positioned throughout the mesh will achieve a goal of a better approximation between the filtering mesh and the orifice of the artery with an improvement of a filtering capacity due to accumulation and trapping of emboli within the dome of such protrusions.

Similar protrusions in the filtering mesh may be created in other portions of the mesh to effectively cover the orifice of the innominate artery 41, the orifice of the right subclavian artery 96, the orifice of the right carotid artery 94, and the orifice of the left subclavian artery 98 which are primary and secondary branches of the aortic arch carrying blood to the brain.

In other embodiments such protrusions may be created at other areas and segments of the mesh that are away from the ostia of the head vessels. For example, a protrusion may be created at the very distal portion of the mesh 150 that may be expanded within the left subclavian artery 23 (FIG. 13-B) or distal aortic arch 22 and proximal descending aorta to create an area of a maximal accumulation of the trapped emboli downstream and away from the innominate and carotid arteries 41, 23. Such an area may have a shape of a pouch for accumulation and temporary storage of emboli and acting as a sink for trapped emboli. To achieve a formation of a protrusion on the surface of the mesh the underlying expanding balloon must contain a protrusion that would create an appropriate shape on the outer mesh. In other embodiments some parts of the mesh itself may be made out of a very smooth, thin, compliant, floating material that would protrude into the orifices of the head arteries 41, 26, 23 upon the expansion and/or as a result of the forward blood flow entering the orifice of the head artery and pushing this portion of the mesh into the orifice of the artery (such as orifice 92 of the artery 26L of FIGS. 13-B and C).

As a result, a more congruent and coplanar coverage of the inner aspect of the inner aortic arch 22 and its head branches 41, 26, and/or 23 is achieved providing for a much more effective clearance of the embolic particles.

In order to facilitate the advancement of the occluding catheter 37 in patients with difficult anatomy, a guide wire 100 may be used in one of the channels 70 or 74. With reference to FIGS. 12-A and 12-B, the guide wire 100 need not be used. Here, the shaft 104 is highly compliant and there is a narrow waist that makes up segment 44. The occluding catheter 37 includes a pair of occluding balloons 38, 42 and segment 44 in the middle of these occluding balloons 38, 42 improves flexibility of the occluding catheter 37. Both balloons 38, 42 and a segment 44 are covered by a single "bridging" mesh 142 that is made out of a compliant material that will preserve its shape and configuration once expanded while bridging the gap between the balloons 38 and 42 (FIGS. 5-C, D, E, F; FIGS. 11, 12, 13, 14, 15). Such material, as it was described for other embodiments, may be compliant, able to recoil, may have shape memory, memory recoil and expansion features. Such materials may comprise a combination of metal (such as titanium, nitinol etc.), plastic or biopolymer (such as polyurethane, monofilament polypropylene, carbon fiber, fiberglass, polyester).

As previously described, separate occluding balloon channels 68 and 72 can be used for separate inflation of the proximal and distal occluding balloons 38 and 42. This allows for selective control of the occlusion of the left carotid artery 26L and innominate arteries 41.

The pair of occluding balloons 38, 42 in FIGS. 12-A and 12-B may be rearranged so that they are only a single occluding balloon 38, covered by mesh 150. In this regard, the single occluding balloon 38-mesh 150 arrangement will have a proximal portion 116 and a distal portion 118 separated by segment 44 that is not capable of being inflated. A single occluding balloon channel 68 can be used to inflate both the proximal and distal portions 116, 118. Although a single occluding balloon 38 is present, it is divided into two or more portions via uninflated segments such as segment 44 or by various other bands or waists that effect division. Segment 44, when effecting separation of proximal and distal portions 116, 118, achieves better flexibility of the occluding catheter 37 at the level between the two portions 116, 118. This option may allow for an easier passage of the catheter 37 in case of a sharp angle between the innominate artery 41 and left carotid artery 26L or left subclavian artery 23. If a pair of occluding balloons 38, 42 is employed, the same goal may be achieved by the segment 44. Measurement of arterial pressure and assessing the pressure waveform via the openings 54, 56 before and after inflation will allow confirmation of the adequacy of the flow interruption in the carotid arteries 26L and 26R. In addition, after a full expansion of the mesh 150 and deflation of balloons 38, 42, the openings 54, 56 may serve for aspiration of emboli that are trapped inside the mesh 150 or are passing through. An additional plurality of openings 54, 56 may be provided to assure more efficient clearance of said emboli with the openings 54, 56 located within the area, covered by the mesh 150.

A manometer 124 may be in communication with the end pressure measurement port 50 and the intermediate pressure measurement port 52 to measure pressures at the opening of the shaft 54 (downstream from the proximal occluding balloon 38, yet within the area of coverage by the filtering mesh in the innominate artery 41 or right subclavian artery 23R) and at the distal tip opening of the shaft 56 (downstream from the distal occluding balloon 42, yet within the area of coverage by the filtering mesh in the left carotid artery 26L). Said openings also may serve for aspiration and removal of emboli from the filtering mesh throughout the course of the procedure. A pressure supply 126 is in communication with the proximal occluding balloon inflation port 46 and the distal occluding balloon inflation port 48 to provide inflation pressure for the occluding catheter 37. An alarm system 114 is in communication with the pressure supply 126, manometer 124, and Doppler probes 190, 192, 194, 198, 200. Should the physician or physician's assistant forget to deflate the occluding balloons 38, 42 in a timely fashion, an alarm would go off and the occluding balloons 38, 42 would deflate spontaneously to avoid undue interruption of the cerebral flow. The alarm could be also triggered by the occurrence of emboli 27 detected by carotid Doppler via ultrasound probes 198, 200 at the depths and frequencies on insonation commensurate with the parameters for detection of the high intensity transient signals, analogous to such signals obtained via transcranial Doppler 122 (also in communication with the alarm system 114). In addition, emboli 27 and 28 can be detected by intravascular Doppler probes 190, 192, 194 placed throughout the course of the catheter shaft exposed to the bloodstream and corresponding to the anatomic areas of the aortic arch 22, innominate artery 41 and carotid arteries 26 (FIGS. 1, 2, 4-B, 5, 5-A, 9-A, 9-B). Such probes 190, 192, 194 can be positioned either inside or outside the filtering mesh and may include ultrasound probes with different frequencies, depths and modes of insonation to obtain a full range of data from arteries 22, 41, 23 comprising embolic signals, blood velocity and B-mode imaging real time. In addition to monitoring the important parameters of blood flow and anatomy of the arteries during the procedure, such system will be able to signal an urgent need for an occlusion or filtering of the blood flow to innominate, carotid and/or vertebral arteries any time when emboli appear in the blood stream. Here, the alarm system 114 will cause inflation of the occluding balloons 38, 42 as soon as the emboli are detected by at least one of the ultrasound probes 190-194 and/or 198-200. The alarm system 114 along with deflation or inflation of the occluding balloons 38, 42 and expansion of the filtering mesh 130, 140, 142 or 150 could be overridden by the physician when clinically indicated.

B-Mode imaging is the display of a two-dimensional ultrasound image made up of bright dots that are representative of ultrasound echoes. The amplitude of the reflected echo is representative of the brightness of each displayed dot. This imaging technology may be used to view portions of a patient's anatomy such as carotid arteries, aorta, innominate artery, and subclavian arteries.

Another exemplary embodiment of the occluding catheter 37 surrounded by the filtering mesh cover 150 is shown in FIGS. 13-A,B,C and 14-A,B. This embodiment achieves both interruption and filtering of cerebral arterial inflow without placing the occluding catheter 37 into carotid arteries 26L and 26R by creating a single occluding balloon 38 extending throughout the distance between the bifurcation of the innominate artery 41 and the orifice 98 of a left subclavian artery 23L. The single occluding balloon 38 and its outer mesh 150 may be provided so that no other occluding balloons and mesh filters, and in some instances no other balloons at all, are present on the occluding catheter 37.

When inflated, the occluding balloon 38 surrounded with the filtering mesh 150 will effectively cover the orifice of the right subclavian artery 96, the orifice of the right carotid artery 94, the orifice of the left carotid artery 92, and the orifice of the left subclavian artery 98 which are all primary or secondary branches of the aortic arch 22. This inflation will achieve a goal of expanding the filtering mesh and blocking the flow to the brain by blocking flow to the right and left carotid arteries 26R and 26L and to both the right subclavian and left subclavian arteries 23R and 23L and, therefore, both right and left vertebral arteries (FIG. 13-B), whereas a subsequent deflation of the balloon 38 leaving the filtering mesh 150 expanded (FIG. 13-C) will restore the blood flow to the brain while still preventing the emboli from entering the carotid 26R and 26L, subclavian 23 and vertebral arteries. Said emboli will be either deflected or trapped by the mesh 150 that will be left expanded after the deflation of the balloon 38.

The occluding catheter 37-mesh 150 combination in this arrangement achieves complete avoidance of any manipulations on the carotid arteries 26R and 26L, thus eliminating the risk of induced injury or emboli 28, leading to stroke, problems that are known to occur in the prior art devices. As shown, the occluding balloon 38-mesh 150 device is not located within the right or left carotid arteries 26R, 26L when inflated or deflated. The occluding balloon 38 and its mesh 150 may also not be located within the right subclavian artery 23R or left subclavian artery 23L when inflated in some embodiments.

The occluding catheter 37 may be inserted via the peripheral artery of the right or left arm. FIGS. 13 and 14 show introduction through the right arm for vascular access. A guide wire 100 may first be passed via the brachial artery and advanced first into the innominate artery 41, then the aortic arch 22, and finally into the left subclavian artery 23L. The occluding catheter 37 with an optional outer sheath 170 will be next advanced over the guide wire 100 and consequently first into the innominate artery 41, then the aortic arch 22 and finally into the left subclavian artery 23L. In other embodiments, however, a wireless insertion is possible by designing the distal segment of the catheter 37 with the distal segment of the balloon 38 and mesh 150 made of a flexible, light and easily floating material with an optional curved distal end. This arrangement will achieve a goal of a correct positioning of the catheter of FIGS. 13-A, B, C and 14-A, B without the use of the guidewire 100, thus decreasing the amount of instrumentation in the areas of the aorta and the areas of the takeoff of the carotid and vertebral arteries. The occluding balloon 38 and its filtering mesh 150 extend from the level of the innominate artery 41 to the level of the left subclavian artery 23L.

The left arm is used for insertion as shown in FIG. 15. The occluding catheter 37 is first advanced into the left subclavian artery 23L, then the aortic arch 22, and then into the innominate artery 41 and right subclavian artery 23R. The occluding balloon 38 extends through the whole distance between the left and right subclavian arteries 23L, 23R. Inflation of the occluding balloon 38 occludes the orifices 96, 94, 92, and 98 to completely prevent the emboli 28 from entering cerebral circulation via all potential ways of arterial inflow. Pressure in the right subclavian artery 23R may be measured using the distal tip opening 56, and opening of the shaft 54 can be used to measure blood pressure in the left subclavian artery 23L. Openings 56 and 54, when located within the filtering mesh 150, may be used for aspiration of embolic particles trapped within the mesh and/or passing through.

Although the occluding balloon 38 is a single occluding balloon supplied by a single filtering mesh 150 introduced through the left arm of the patient in FIG. 15, should the occluding catheter 37 include proximal and distal occluding balloons 38, 42 and be desired for insertion through the left arm the relative occluding balloon 38, 42 and their corresponding mesh 130, 140, 142 sizes may be varied. For example, the distal occluding balloon 42 and its mesh 140 may be larger in diameter 112 than the diameter 110 of the proximal occluding balloon 38 and its mesh 130. The distal occluding balloon 42 with the mesh 130, when inflated, may block flow through the innominate artery 41, and the proximal occluding balloon 38-mesh 140 would block flow to the left carotid artery 26L by virtue of covering, its orifice on the inner surface of the aortic arch 22. Deflating the balloons 42 and 38 in this configuration while leaving their corresponding meshes 140 and 130 expanded will provide filtering of blood and protection from emboli 28 entering the head vessels 41, 23 and 26. The segment 44 would be between the balloons 38, 42 and would be located in the aortic arch 22. The proximal portion of the occluding catheter 37 and its mesh 130 may be located within the left subclavian artery 23L, thus providing protection from emboli entering left vertebral artery (branch of the left subclavian artery). Placement may be effected by first inflating the distal occluding balloon 42 to allow arterial blood flow to naturally pull it into the innominate artery 41. The distal occluding balloon 42 may be deflated to allow for determination of the positioning of the occluding catheter 37. The proximal occluding balloon 38 may be inflated to determine its positioning as it may block flow through both the left carotid artery 26L and the left subclavian artery 23L. Deflating balloons 38 and 42 after their meshes 130 and 140 were expanded will provide for a continuous filtering, elimination, deflection and redirection of incoming emboli throughout the course of the procedure.

Although described as blocking and/or filtering flow through both of the carotid arteries 26R and 26L, it is to be understood that only one of the carotid arteries 26R or 26L may be blocked and/or filtered in certain arrangements and uses of the occluding catheter 37.

The size and shape of the occluding balloon 38 and its mesh 130 or 150 can vary depending on the patient's anatomy and the size of the arteries discussed herein. For this purpose it may be the case that low pressure, highly compliant occluding balloons 38 and their respective meshes of conical and ovoid shape are used with larger and optionally flattened central segments corresponding to the patient's innominate artery 41, aortic arch 22, and aortic arch area 156 and the narrower peripheral segments corresponding to the level of right and left subclavian arteries 23R and 23L. The large segment of the occluding balloon 38 should be large enough to occlude the innominate artery 41 and the orifice 92 of the left carotid artery 23L, but not too large to compromise the lumen 120 of the aortic arch 22. In some embodiments the "large" segment of the balloon 38 is rather wide, concave, and congruent to the inner aspect of the craniad portion of the aortic arch 22 providing wide coverage (more than 30% of the perimeter of the inner surface of the arterial wall of the aortic arch 22) of the aortic arch area 156, corresponding to the orifices of the head vessels 41, 26, 23. It may be made sufficiently compliant, as well as the corresponding portion of the mesh, to assure slight herniation into the orifices of the innominate 41, left carotid 26L and left subclavian 23L arteries during inflation with the persistent herniation of the expanded mesh after the balloon is deflated. In other embodiments the filtering mesh may be made sufficiently compliant to herniate further into the orifices 96, 94, 92 and 98 after deflation. Thus in some arrangements, the occluding balloon 38 and its outer mesh 130 or 150 may extend into any one of or all of the arteries 23R, 26R, 26L and 23L.

The diameter 120 of the aortic arch 22 needs to be larger than the diameter 110 of the occluding balloon 38 when the occluding balloon 38 is inside of aortic arch 22 and is inflated. This arrangement will block blood flow to the carotid arteries 26R, 26L but will allow for divergence of blood flow carrying the emboli 28 into the distal aorta 24 and away from the cerebral circulation. The maximal diameter 110 of this segment of the occluding balloon 38 within the aortic arch 22 may not exceed 60-70% of the diameter 120 of the aortic arch 22. In other arrangements, the diameter 110 within the aortic arch 22 may be up to 25%, up to 35%, 50%, or up to 60% of the diameter 120. The corresponding diameter of mesh 150 expanded by the balloon 38 generally approximates the diameter 110 of the segment of the balloon 38 within the aortic arch 22, however in some embodiments it may approximate or even exceed by 20-30% the inner diameter 120 of the aortic arch 22 due to creation of a hyperexpansile, and optionally self-expanding filtering mesh that may be deployed within an aortic arch using a catheter 37 and filter the blood coming through, yet would not obstruct the flow through the aortic arch 22 and its branches 41, 26, 23. In some embodiments this mesh may be made detachable from the catheter 37 and have self-retaining features such as hyperexpansion, shape memory, recoil and/or external attachment hooks 220 (FIG. 9-D, FIG. 18) to stay within the aortic arch and protect head vessels from emboli for a longer period of time way beyond the length of the procedure. Such mesh can be later removed using standard endovascular techniques or made biodegradable to get dissolved or reabsorbed in the future.

Although described as preventing emboli 28 from flowing to the carotid arteries 26R, 26L, the occluding catheter 37 may also be used to prevent emboli 28 from flowing through the right subclavian artery 23R and/or the left subclavian artery 23L and, therefore, to right and/or left vertebral arteries, carrying blood to the posterior brain. This prevention may be in addition to or alternatively to prevention of flow through the carotid arteries 26R and/or 26L.

The filtering mesh 150 may be made out of metal, plastic or a biopolymer wire in a single or multiple spiral, concentric, grid, interwinding and other configurations amenable to compression C, extension E, stretching S, torqueing T and bending B as shown in FIGS. 13-17.

The size of filtering pores of the mesh 150 may vary from 50 to 500 micron depending on a particular embodiment and on an optional adjustment mechanism achieving the goal of changing the dimensions of filtering pores during the procedure by extending E, stretching S, torqueing T, bending B the mesh 150 using an outer sheath 170, catheter or a guidewire releasably connected to mesh 150 via a locking mechanism 172-174. Said outer sheath 170, catheter and a guidewire once connected and locked to the slidable ring 174 of the proximal part of the mesh may be pulled back, pushed forward and rotated around their long axis to induce a respective extension and/or stretching, compression and torqueing of the mesh 150 leading to deformation of the pores 180, 182, 184 of the mesh with a resultant 0.30-6.50-fold increase or decrease of at least one of their dimensions d, h or radius R (FIGS. 16, 17, 18). In addition, applying forward pressure on the proximal portion of the catheter 37 with the distal portion of the catheter locked and/or immobilized in one of the left or right subclavian arteries will lead to bending B of the part of the mesh 150 with the resultant deformation of pores 180, 180, 184 as described above. Such deformation may affect differently the pores 180 vs. pores 182 located on the opposite sites of the circumference of the mesh 150 in relation to the head vessels (FIGS. 9-B, C, D and 10-B, C, D; FIGS. 15, 16, 17) and may selectively increase the size of pores 180 of the cardiac area of the mesh ($1^{st}$ barrier), yet—to decrease the size of the pores 182, located on the opposite (cranial) side of the mesh ($2^{nd}$ barrier) and facing the orifices of the head arteries 41, 26, 23. For example, as shown on FIG. 15, bending the catheter 37 along its central longitudinal axis may produce a horizontal and internal bend on the most of the area 154 of the mesh facing the area 156 of the aortic arch 22 comprising the orifices of the head vessels 41, 26, 23 and an opposite bend on the opposite side of the mesh corresponding to the area 152 that is facing the incoming flow from the heart, ascending aorta and the aortic arch. As a result, the pores 182, located in the area 154 of the mesh 150 subjected to the internal-horizontal bend, will undergo compression along the longitudinal central axis of the catheter 37, while the opposite pores 180, located in the area 152 of the mesh, will be subjected to the external-horizontal bend with a resultant extension and stretching along the longitudinal axis of the catheter 37. In this arrangement, depending on the "neutral" i.e. initial pore geometry and configuration as depicted in FIG. 16-A vs. 16-B, further compression along the axis $d^1$ due to bending will lead to increasing of filtering capacity for the pore of FIG. 16-A, yet similar compression along the axis $d^4$ during bending will lead to decreasing the filtering capacity of the pore of FIG. 16-B. Conversely, an extension secondary to bending and stretching along the axis $d_1$ of the pore of FIG.-A may increase its filtering capacity, whereas similar forces applied to the similar axis $d_4$ of the pore of FIG. 16-B may lead to an opposite effect. These features per se and in combination with the different initial pore sizes of pores 180 (large), 182 (small), 184 (intermediate) located in their respective areas 152 (facing the incoming flow from the heart and the aorta), 154 (facing the ostia of the innominate and carotid arteries) and 158 (intermediate) of the mesh assure a plurality of processes and options aimed to achieve a goal of an optimal and selective filtering of the blood coming to the brain. For example, in one embodiment the area 152 of the outer surface of the mesh 130, 140, 142 or 150 facing the incoming flow from the heart and aorta may contain larger pores 180, ranging in size from 150 to 500 micron, whereas the area 154 facing with its outer surface the ostia of the head vessels 42, 23, 26 may contain smaller pores 182 ranging in size between 50 and 250 micron. There may also be an intermediate area 158, containing pores ranging from 150 to 350 microns. Said pores may be designed in such a way that the large pores 180 will have a shape of the pore of FIG. 16-B or 16-C and are placed in the area 152 ($1^{st}$ barrier on the way of emboli to the brain), whereas the pores of shape of FIG. 16-A are the small pores 182 placed in the area 154 ($2^{nd}$ barrier on the way of emboli to the brain). Assuming that the initial or "neutral" (i.e. before any traction, stretching, torqueing or bending is applied) radius R of pores 180 of a fully expanded mesh 150 before applying any external forces is 200 microns, whereas the initial (neutral) radius R of pores 182 of the same mesh in its relaxed state is 100 microns, these parameters may be changed as necessary by applying traction, stretching, compression, torqueing or bending to the mesh during the procedure as described herein. For example, if a significant embolic load is expected or recorded via an automated alarm system described above, the size of pores can be quickly diminished by pulling back the outer sheath 170 or a similar catheter or guidewire connected to the proximal sliding ring 174 of the mesh 150. As a result, the mesh 150 may elongate and, at certain traction threshold, stretch with a proportional decrease in size R of pores 180 and 182 of the respective mesh areas 152 and 154 with the resultant increase of the mesh filtering capacity. Conversely, if the emboligenic part of the procedure is completed and the risk of emboli is minimal, the pores of the mesh may be returned to its neutral position by relaxing the tension, stretching and/or torqueing applied to the mesh with the increase in the radius of pores R to its initial dimension and restoring the baseline perfusion to the brain through the unobstructed field.

The disclosed feature of uneven, variable and adjustable pore size allows to achieve multiple goals of the most effective, efficient and safest clearance of emboli by virtue of several clearance mechanisms comprising deflection, scattering, trapping, accumulation and re-direction of cerebral emboli with an option of adjusting the degree and the relative contribution of each mechanism to the process of clearance. As depicted in FIG. 18, the emboli 28 are propelled by the forward blood flow from the heart and the aorta towards the area 152 ($1^{st}$ barrier) and, possibly 158, of the mesh 150, containing the large and intermediate pores 180, 184. As a result, the emboli larger than the size of pores 180, 184 will be deflected downstream and away from the head vessels. The emboli 28 that are smaller than the pores 180, 184 may enter the space inside the mesh 150 where they will encounter the smaller pores 182 of the mesh area 154 ($2^{nd}$ barrier) facing the area 156 of the aortic arch 22 overlapping the ostia of the head vessels 41, 26, 23 (FIGS. 15,18). The majority of these emboli, even if they are smaller than the size of pores 182, will get deflected, redirected and/or trapped inside the mesh due to their scattering, loss of their kinetic energy and initial trajectory directed to the brain, and loss of the momentum created by the $1^{st}$ barrier. These effects will be also augmented by the blood turbulences developing as a result of blood entering the mesh and accumulation of embolic particles at the $2^{nd}$ barrier further increasing its filtering capacity. If the intravascular or external ultrasound probes 190, 192, 194, 198, 200 or transcranial Doppler probes detect cerebral emboli passing through the $2^{nd}$ mesh barrier (area 154) the size of pores 180, 182 and 184 may be effectively decreased by applying the extension, stretching, torqueing and bending forces as described above. Such decrease in the mesh pore may be performed automatically if synchronized with the alarm system 114.

Considering the fact that most of the embolic particles have a complex tri-dimensional and/or spheroid configuration, such deformation of the filtering pores with the decrease of at least one of the dimensions d, h or radius R of the pore size will prevent such embolic particles from passing through and thus increasing dramatically the filtering capacity of the mesh (FIG. 17-A, B). It is to be understood, however, that in some of the embodiments the resultant change of the mesh dimensions may be less than 0.3 or more than 6.5 times than the initial mesh size.

To facilitate the positioning of the catheter 37 and orientation of its mesh 130, 140, 142, 150 in order to achieve approximation of the mesh area 152 with the aortic arch area 156 and the orifices of the head vessels 41, 26, 23 one may use radiopaque markers on the catheter 137 and its mesh, defining the area 152, and optionally the areas 92, 94 and 96 and 156 of the aortic arch 22.

It is to be understood that the ways the disclosed art is applied may vary within the scope of the features disclosed and are not limited to the embodiments presented herein.

There may be different combinations of the features described within the different embodiments that may be combined in a different way and applied to other embodiments, thus creating a new embodiment by virtue of new combination of the features disclosed. For example, the pores of the mesh may be equal throughout its course and made of different materials. The initial size of pores in a relaxed state of the mesh may vary in different embodiments. Likewise, the range of pore deformation and size change may be different in different embodiments depending on their geometry, mechanics and the type of the external force applied. The feature of the mesh retrieval into the outer sheath 170 may be combined with the locking and unlocking mechanism 172-174, which in turn may comprise a sliding ring 174 or 172. An outer sheath 170 may be supplemented or substituted by a similar catheter or a guidewire able to carry a similar function of connecting to the mesh, and achieving its traction, extension, stretching, torqueing, compression and bending. Any of the mesh 130, 140, 142 and 150 can be fashioned to be detachable, self-expanding, self-collapsible, and/or self-retaining in at least one of the aortic arch 22, innominate artery 41, carotid arteries 26 and subclavian arteries 23. It may be detached from the catheter 37 and left in vessels 22, 41, 26, 23 for a defined period of time for a period of several hours or days or longer with a subsequent endovascular retrieval or biodegradation (if the mesh is made from a biodegradable material).

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

The invention claimed is:

1. A catheter for preventing stroke, comprising:
a shaft that has a proximal end and a distal end;
an occluding balloon carried by the shaft, wherein the occluding balloon is inflated to occlude blood flow to at least one of the right carotid artery and the left carotid artery, wherein the occluding balloon is coaxial with the shaft;
a filtering mesh that assumes an expanded configuration when the occluding balloon is expanded and maintains the expanded configuration when the occluding balloon is deflated, wherein the filtering mesh is coaxial with the shaft, wherein expansion of the occluding balloon causes expansion of the filtering mesh;
wherein blood flows through pores of the filtering mesh when the occluding balloon is deflated, wherein blood flows through the pores of the filtering mesh when the occluding balloon is partially inflated; and
wherein the blood does not flow through the pores of the filtering mesh that are formed by the portions of the filtering mesh that are in contact with the occluding balloon when, the occluding balloon is fully inflated;
wherein the filtering mesh is carried by the shaft such that the pores of the filtering mesh are located proximal to the occluding balloon extend across the occluding balloon and are located distal to the occluding balloon.

2. A catheter for preventing stroke, comprising:
a shaft that has a proximal end and a distal end;
an occluding balloon carried by the shaft, wherein the occluding balloon is inflated to occlude blood flow to at least one of the right carotid artery and the left carotid artery;

a filtering mesh that assumes an expanded configuration when the occluding balloon is expanded and maintains the expanded configuration when the occluding balloon is deflated;
wherein blood flows through pores of the filtering mesh when the occluding balloon is deflated, wherein blood flows through the pores of the filtering mesh when the occluding balloon is partially inflated; and
wherein the blood does not flow through the pores of the filtering mesh that are formed by the portions of the filtering mesh that are in contact with the occluding balloon when the occluding balloon is fully inflated;
wherein the occluding balloon is a proximal occluding balloon and further comprising a distal occluding balloon that is surrounded by the filtering mesh;
wherein the proximal occluding balloon is inflated to occlude blood flow and expand the filtering mesh to filter blood flow to the right carotid artery or the left carotid artery;
wherein the distal occluding balloon is inflated to occlude blood flow and to expand the filtering mesh to filter blood flow to the other one of the right carotid artery or the left carotid artery not occluded and filtered by the proximal occluding balloon;
wherein both the proximal and distal occluding balloons when deflated allow blood flow through the filtering mesh and to the right and left carotid arteries, wherein when the proximal and distal occluding balloons are fully inflated blood flow through the pores of the filtering mesh is prevented adjacent the proximal and distal occluding balloons;
wherein the shaft has a segment that is located between the proximal occluding balloon and the distal occluding balloon.

3. The catheter as set forth in claim 2, wherein the proximal occluding balloon when fully inflated has a greater diameter than the distal occluding balloon when fully inflated, wherein the filtering mesh around the proximal occluding balloon when expanded has a greater diameter than the expanded filtering mesh around the distal occluding balloon when both the proximal and distal occluding balloons are fully inflated.

4. The catheter as set forth in claim 2, wherein the filtering mesh is discontinuous between the proximal occluding balloon and the distal occluding balloon such that the filtering mesh does not filter the blood flow all the way from the proximal occluding balloon to the distal occluding balloon.

5. The catheter as set forth in claim 2, wherein the shaft has a proximal balloon channel that extends from the proximal occluding balloon to a proximal balloon inflation port located at a proximal end of the shaft;
wherein the shaft has a distal balloon channel that extends from the distal occluding balloon to a distal balloon inflation port located at the proximal end of the shaft, wherein the distal balloon channel and the proximal balloon channel are not in fluid communication with one another;
wherein the shaft has a pressure measurement and blood aspiration channel that extends from a distal tip opening of the shaft located at the distal end of the shaft to an end pressure measurement port located at the proximal end of the shaft, wherein the distal tip opening is located within the filtering mesh and is distal from the distal occluding balloon, wherein the distal tip opening aspirates trapped particles from a space inside the filtering mesh.

6. The catheter as set forth in claim 2, wherein the shaft has a pressure measurement and blood aspiration channel that extends from a distal tip opening of the shaft located at the distal end of the shaft to an end pressure measurement port located at the proximal end of the shaft, wherein the distal tip opening is located distal from the distal occluding balloon and distal from the filtering mesh, wherein the distal tip opening is located outside of the filtering mesh when the filtering mesh is expanded.

7. A catheter for preventing stroke, comprising:
a shaft that has a proximal end and a distal end;
an occluding balloon carried by the shaft, wherein the occluding balloon is inflated to occlude blood flow to at least one of the right carotid artery and the left carotid artery;
a filtering mesh that assumes an expanded configuration when the occluding balloon is expanded and maintains the expanded configuration when the occluding balloon is deflated;
wherein blood flows through pores of the filtering mesh when the occluding balloon is deflated, wherein blood flows through the pores of the filtering mesh when the occluding balloon is partially inflated; and
wherein the blood does not flow through the pores of the filtering mesh that are formed by the portions of the filtering mesh that are in contact with the occluding balloon when the occluding balloon is fully inflated;
wherein the occluding balloon is a proximal occluding balloon and further comprising a distal occluding balloon that is surrounded by the filtering mesh;
wherein the proximal occluding balloon is inflated to occlude blood flow and expand the filtering mesh to filter blood flow to the right carotid artery or the left carotid artery;
wherein the distal occluding balloon is inflated to occlude blood flow and to expand the filtering mesh to filter blood flow to the other one of the right carotid artery or the left carotid artery not occluded and filtered by the proximal occluding balloon;
wherein both the proximal and distal occluding balloons when deflated allow blood flow through the filtering mesh and to the right and left carotid arteries, wherein when the proximal and distal occluding balloons are fully inflated blood flow through the pores of the filtering mesh is prevented adjacent the proximal and distal occluding balloons;
wherein the shaft has a segment that is located between the proximal occluding balloon and the distal occluding balloon;
wherein the shaft has an intermediate pressure measurement and blood aspiration channel that extends from an intermediate pressure measurement and blood aspiration channel opening of the shaft located proximal to the proximal occluding balloon, wherein the intermediate pressure measurement and blood aspiration channel extends to an intermediate pressure measurement and aspiration port located at the proximal end of the shaft;
and wherein the intermediate pressure measurement and blood aspiration channel opening is located inside the filtering mesh and aspirates trapped particles from the space inside the filtering mesh when the filtering mesh is in the expanded configuration.

8. A catheter for preventing stroke, comprising:
a shaft that has a proximal end and a distal end;

an occluding balloon carried by the shaft, wherein the occluding balloon is inflated to occlude blood flow to at least one of the right carotid artery and the left carotid artery;

a filtering mesh that assumes an expanded configuration when the occluding balloon is expanded and maintains the expanded configuration when the occluding balloon is deflated;

wherein blood flows through pores of the filtering mesh when the occluding balloon is deflated, wherein blood flows through the pores of the filtering mesh when the occluding balloon is partially inflated; and wherein the blood does not flow through the pores of the filtering mesh that are formed by the portions of the filtering mesh that are in contact with the occluding balloon when the occluding balloon is fully inflated;

wherein the shaft has an intermediate pressure measurement and blood aspiration channel that extends from an intermediate pressure measurement and blood aspiration channel opening of the shaft located proximal to the occluding balloon, wherein the intermediate pressure measurement and blood aspiration channel extends to an intermediate pressure measurement and aspiration port located at the proximal end of the shaft;

and wherein the intermediate pressure measurement and blood aspiration channel opening is located outside of the filtering mesh when the filtering mesh is in the expanded configuration;

wherein the filtering mesh is carried by the shaft such that the pores of the filtering mesh are located proximal to the occluding balloon extend across the occluding balloon and are located distal to the occluding balloon.

9. A catheter for preventing stroke, comprising:
a shaft that has a proximal end and a distal end;
an occluding balloon carried by the shaft, wherein the occluding balloon is inflated to occlude blood flow to at least one of the right carotid artery and the left carotid, artery;
a filtering mesh that assumes an expanded configuration when the occluding balloon is expanded and maintains the expanded configuration when the occluding balloon is deflated;
wherein blood flows through pores of the filtering mesh when the occluding balloon is deflated, wherein blood flows through the pores of the filtering mesh when the occluding balloon is partially inflated; and
wherein the blood does not flow through the pores of the filtering mesh that are formed by the portions of the filtering mesh that, are in contact with the occluding balloon when the occluding balloon is fully inflated;
ultrasound Doppler probes mounted along the shaft, wherein the probes detect:
real time embolic signals,
paths of emboli,
intensity and direction of propagation of the emboli in relation to an aortic arch and head vessels,
blood velocity and B-mode images of an aorta, innominate artery,
and left and right carotid arteries,
an alarm system that activates a pressure supply to the occluding balloon to cause inflation and the filtering mesh expansion when embolic signals, complete or partial occlusion of the carotid arteries, or increased or decreased systolic velocity and abnormal flow patterns are detected by the ultrasound probes;
wherein the alarm system deflates the occluding balloon when the occluding balloon remains inflated for a cut-off period of time, and wherein the alarm system has a manual override to prevent inflation and deflation by the alarm system.

10. A catheter for preventing stroke, comprising:
a shaft that has a proximal end and a distal end, wherein the shaft has a blood aspiration channel that extends from a blood aspiration channel opening of the shaft, wherein particles are aspirated through the blood aspiration channel opening of the shaft;
an occluding balloon carried by the shaft, wherein the occluding balloon is inflated to occlude blood flow to at least one of the right carotid artery and the left carotid artery, wherein the occluding balloon engages the shaft; and
a filtering mesh that assumes an expanded configuration when the occluding balloon is expanded, wherein blood flows through pores of the filtering mesh when the occluding balloon is partially inflated, wherein the filtering mesh engages the shaft at a location proximal to the occluding balloon and the blood aspiration channel opening, and wherein the filtering mesh engages the shaft at a location distal to the occluding balloon and the blood aspiration channel opening;
wherein the blood aspiration channel opening is configured for aspirating emboli from inside of the filtering mesh.

11. The catheter as set forth in claim 10, wherein the occluding balloon is located within an aortic arch, a left subclavian artery, and an innominate artery of the patient, and wherein the occluding balloon is not located within the left carotid artery of the patient, and wherein blood flow to at least one of the carotid and vertebral arteries is occluded when the occluding balloon is fully inflated, and not occluded but filtered when the occluding balloon is deflated and the filtering mesh is in the expanded configuration, and partially occluded and filtered when the occluding balloon is partially expanded and the filtering mesh is at least partially expanded.

12. The catheter as set forth in claim 10, wherein the occluding balloon performs partial occlusion, wherein the filtering mesh is in the expanded configuration such that only filtered blood flows past the partially inflated occluding balloon while being filtered through the filtering mesh to both the right carotid artery and the left carotid artery.

13. The catheter as set forth in claim 10, wherein the blood flows through the space between the occluding balloon when deflated and the filtering mesh in the expanded configuration and is filtered in relation to the size of the pores;
wherein the size of the pores of the mesh varies between 50 and 500 micron, allowing for the flow of blood therethrough when the occluding balloon is at least partially deflated, wherein the catheter has an occluding mode, a filtering mode and a partial occluding-partial filtering intermediate mode that have different degrees of expansion of the filtering mesh and the concomitant expansion of the occluding balloon allowing for variable ratios of filtering versus deflection of the embolic particles with the concomitant proportional interdependent degree of flow reduction versus flow preservation through cerebral vessels.

14. The catheter as set forth in claim 10, wherein the filtering mesh has a cylindrical shape, conic shape, pear shape, pouch shape, or a spherical shape,
wherein the filtering mesh comprising herniations configured to face one or more orifices of the head vessels, the cranial area of the aortic arch, or the descending aorta to, provide for a congruent and coplanar approximation of filtering mesh surface to body anatomy.

15. A catheter for preventing stroke, comprising:
a shaft that has a proximal end and a distal end, wherein the shaft has a blood aspiration channel that extends from a blood aspiration channel opening of the shaft, wherein particles are aspirated through the blood aspiration channel opening of the shaft;
an occluding balloon carried by the shaft, wherein the occluding balloon is inflated to occlude blood flow to at least one of the right carotid artery and the left carotid artery, wherein the occluding balloon engages the shaft; and
a filtering mesh that assumes an expanded configuration when the occluding balloon is expanded, wherein blood flows through pores of the filtering mesh when the occluding balloon is partially inflated, wherein the filtering mesh, engages the shaft at a location proximal to the occluding balloon and wherein the filtering mesh engages the shaft at a location distal to the occluding balloon;
wherein the blood aspiration channel is an intermediate pressure measurement and blood aspiration channel, and wherein the blood aspiration channel opening is an intermediate pressure measurement and blood aspiration channel opening;
wherein the shaft has an occluding balloon channel that extends from the occluding balloon to an occluding balloon inflation port located at the proximal end of the shaft, wherein the shaft has an end pressure measurement-aspiration channel that extends from a distal tip opening of the shaft located at the distal end of the shaft to an end pressure measurement-aspiration port located at the proximal end of the shaft,
wherein the intermediate pressure measurement and blood aspiration channel opening is located proximal to both the occluding balloon and the distal tip opening to an intermediate pressure measurement and blood aspiration port located at the proximal end of the shaft, and
wherein at least one of the intermediate pressure measurement and blood aspiration channel opening or the distal tip opening opens into the space between the occluding balloon and the filtering mesh and aspirates emboli from the space inside of the filtering mesh and from the blood passing through.

16. A catheter for preventing stroke, comprising:
a shaft that has a proximal end and a distal end, wherein the shaft has a blood aspiration channel that extends from a blood aspiration channel opening of the shaft, wherein particles are aspirated through the blood aspiration channel opening of the shaft;
an occluding balloon carried by the shaft, wherein the occluding balloon is inflated to occlude blood flow to at least one of the right carotid artery and the left carotid artery; and
a filtering mesh that assumes an expanded configuration when the occluding balloon is expanded, wherein blood flows through pores of the filtering mesh when the occluding balloon is partially inflated;
wherein the occluding balloon has a proximal portion and a distal portion in which the proximal portion is larger than the distal portion, wherein the proximal portion is located within an innominate artery of the patient and completely occludes blood flow to the right carotid artery and to a right subclavian artery of the patient when inflated, wherein the distal portion is located within the left carotid artery and when inflated completely occludes blood flow to the left carotid artery;
wherein the blood is allowed to flow through the pores when the balloon is deflated, but not allowed to flow through the pores when the balloon is completely inflated, and wherein partial inflation of the occluding balloon leads to a partial restriction of the blood flow through the filtering mesh.

17. A catheter for preventing stroke, comprising:
a shaft that has a proximal end and a distal end, wherein the shaft has a blood aspiration channel that extends from a blood aspiration channel opening of the shaft, wherein particles are aspirated through the blood aspiration channel opening of the shaft;
an occluding balloon carried by the shaft, wherein the occluding balloon is inflated to occlude blood flow to at least one of the right carotid artery and the left carotid artery; and
a filtering mesh that assumes an expanded configuration when the occluding balloon is expanded, wherein blood flows through pores of the filtering mesh when the occluding balloon is partially inflated;
wherein the occluding balloon has a first occluding balloon and a second occluding balloon, wherein the first occluding balloon is located within a right subclavian artery, but not within an innominate or right carotid artery,
wherein the second occluding balloon is located within the left subclavian artery, but not within the left carotid artery,
wherein the filtering mesh covering both occluding balloons is expanded and stretched between the two occluding balloons, when the two occluding balloons cover an area of an aortic arch containing orifices of the innominate, carotid and subclavian arteries,
wherein the filtering mesh stays expanded after the occluding balloons are deflated,
wherein the filtering mesh collapses around the shaft after the two occluding balloons are deflated, and
wherein the process of collapsing the filtering mesh around the shaft is performed by a mechanism selected from the group consisting of spontaneous recoil, aspiration, retraction process, torqueing process, or rotational process.

18. A catheter for preventing stroke, comprising:
a shaft that has a proximal end and a distal end;
an occluding balloon carried by the shaft, wherein the occluding balloon is inflated to occlude blood flow to at least one of the right carotid artery and the left carotid artery;
a filtering mesh that assumes an expanded configuration when the occluding balloon is expanded, wherein blood flows through pores of the filtering mesh when the occluding balloon is partially inflated; and
an adjustment mechanism that adjusts pore sizes of the pores of the filtering mesh.

19. The catheter as set forth in claim 18, wherein the adjustment mechanism comprising a sliding ring slidable along the shaft, wherein the sliding ring is attached to a proximal end of the filtering mesh and moves the filtering mesh in proximal and distal directions along the shaft to compress and extend the filtering mesh, wherein the sliding ring rotates around a central longitudinal axis of the shaft to torque the filtering mesh.

20. The catheter as set forth in claim 18, the adjustment mechanism further comprising:

a slideable outer sheath that moves over the shaft and the filtering mesh;
a locking mechanism carried by the slideable outer sheath and attachable to the sliding ring.

21. The catheter as set forth in claim 18, wherein the pores of the filtering mesh have a relaxed state when no extension, stretching, compression or bending forces are applied to the filtering mesh, and an actuated state when the application of such forces leads to deformation of the pores and changes filtering capacity of the pores;
wherein a cranial side of the filtering mesh faces head vessels of the patient, wherein a cardiac side of the filtering mesh faces the heart of the patient, and wherein an intermediate side of the filtering mesh faces vessel structures of the patient that are not faced by the cranial side or the cardiac side of the filtering mesh;
wherein in the relaxed state of the filtering mesh, the size of the pores at the cranial side of the filtering mesh is smaller than the size of the pores at the cardiac side of the filtering mesh, and wherein the size of the pores at the intermediate side of the filtering mesh is an intermediate size compared to the pores of the cardiac and the cranial sides of the filtering mesh;
and wherein in the relaxed state of the mesh the pore size of the cranial side of the mesh is 50-250 micron, the pore size of the cardiac side of the mesh is 150-500 micron and the pore size of the intermediate side of the mesh is 150-350 micron.

22. The catheter as set forth in claim 18, wherein the occluding balloon and the filtering mesh have an amount of flexibility and mobility to be advanced with a forward blood flow into branches of an aortic arch selected from the group consisting of the left carotid artery, the right carotid artery, a left subclavian artery, a right subclavian artery, and an innominate artery of the patient to allow for wireless catheterization, occlusion and filtering of emboli of the arteries.

23. The catheter as set forth in claim 18, further comprising a slidable outer sheath connectable to a proximal part of the filtering mesh by a locking-and-unlocking mechanism actuated by wedging or axial rotation of connecting parts;
wherein the filtering mesh is tensioned by pulling back the outer sheath connected to a distal part of the filtering mesh cover or relaxed by advancing the outer sheath in relation to an initial neutral position of the catheter shaft and the filtering mesh;
wherein the pores have shapes that are at least one of circular, parallelogram, square, rhombus, pentagon, hexagon;
wherein the tensioning of the filtering mesh by pulling back an outer sheath connected to the proximal end of the filtering mesh in relation to the neutral position and relaxed configuration of the pores leads to elongation of a longitudinal dimension and shortening of a transverse dimension by a factor of 2-5 thus proportionally increasing filtering power of the filtering mesh upon tensioning;
wherein relaxation of the filtering mesh causes shortening of the filtering mesh with widening of the pores and return of pore size to neutral configuration thus proportionally altering the filtering power of the filtering mesh; and wherein the filtering mesh has a degree of stretchability when stretched by pulling back the outer sheath attached to the proximal portion of the mesh cover, ranging from 0 to 50% in relation to the relaxed state, allowing for better compliance and retractability of the filtering mesh and variability of the pore.

24. The catheter as set forth in claim 18, wherein:
the filtering mesh is detachable from the shaft and is rigid enough to provide a self-retaining capacity inside a blood vessel;
wherein an outer surface of the filtering mesh has a plurality of fixation hooks to facilitate fixation and stabilization of the filtering mesh inside the blood vessel;
wherein the dimensions of the filtering mesh in the expanded configuration exceeds the inner dimensions of the aortic arch and branches of the aortic arch, and wherein a self expanding and retraction mechanism of the filtering mesh has a spiral spring-like folding and unfolding of the filtering mesh inside the blood vessel.

25. The catheter as set forth in claim 18, wherein the occluding balloon has a first occluding balloon and a second occluding balloon, wherein the first occluding balloon is located within a right subclavian artery, but not within an innominate or right carotid artery, and
wherein the second occluding balloon is located within a left subclavian artery, but not within the left carotid artery, and
wherein the filtering mesh covers both the first and second occluding balloons and is expanded when the balloons are actuated achieving coverage of an area of an aortic arch containing orifices of the innominate, carotid and subclavian arteries.

26. A catheter for preventing stroke, comprising:
a shaft that has a proximal end and a distal end;
an occluding balloon carried by the shaft, wherein the occluding balloon is inflated to occlude blood flow to at least one of the right carotid artery and the left carotid artery, wherein the occluding balloon engages the shaft; and
a filtering mesh that assumes an expanded configuration when the occluding balloon is expanded, wherein blood flows through pores of the filtering mesh when the occluding balloon is partially inflated, wherein the filtering mesh engages the shaft at a location proximal to the occluding balloon and wherein the filtering mesh engages the shaft at a location distal to the occluding balloon;
wherein the filtering mesh is carried by the shaft such that the pores of the filtering mesh are located proximal to the occluding balloon extend across the occluding balloon and are located distal to the occluding balloon;
wherein the mesh has an area configured for facing arterial inflow of blood, and wherein the mesh has an area configured for facing arterial outflow of blood that is located opposite in a radial direction from the area configured for facing arterial inflow of blood, wherein the pares in the area of the mesh configured for facing arterial inflow of blood are larger in size than the pores in the area of the mesh configured for facing arterial outflow of blood.

* * * * *